United States Patent
Kim et al.

(10) Patent No.: US 8,252,893 B2
(45) Date of Patent: Aug. 28, 2012

(54) CD8 T CELL EPITOPES IN HPV 16 E6 AND E7 PROTEINS AND USES THEREOF

(75) Inventors: Kevin H. Kim, Little Rock, AR (US); Mayumi Nakagawa, Little Rock, AR (US); Anna-Barbara Moscicki, San Francisco, CA (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 631 days.

(21) Appl. No.: 11/343,606

(22) Filed: Jan. 31, 2006

(65) Prior Publication Data

US 2006/0182763 A1  Aug. 17, 2006

Related U.S. Application Data

(60) Provisional application No. 60/648,496, filed on Jan. 31, 2005.

(51) Int. Cl.
*A61K 38/00* (2006.01)
*C07K 2/00* (2006.01)
*C07K 4/00* (2006.01)
*C07K 5/00* (2006.01)
*C07K 7/00* (2006.01)
*C07K 14/00* (2006.01)
*C07K 16/00* (2006.01)
*C07K 17/00* (2006.01)
*A01N 37/18* (2006.01)
*A61P 31/12* (2006.01)

(52) U.S. Cl. .................... 530/300; 514/3.7
(58) Field of Classification Search .................. None
See application file for complete search history.

(56) References Cited

U.S. PATENT DOCUMENTS 6,676,935 B2 * 1/2004 Henderson et al. .......... 424/93.2
7,026,443 B1 * 4/2006 Sette et al. .................. 530/300

FOREIGN PATENT DOCUMENTS

WO    WO 9322338 A1 * 11/1993
WO    WO 0200242 A2 * 1/2002
WO    WO 03008649 A1 * 1/2003

OTHER PUBLICATIONS

Schadeck et al., 1999, Virus Research, vol. 65: 75-86.*
Fisher et al., 1996, Gyn. Oncol. vol. 61: 73-78.*
Muller et al., 1990, J. Gen. virol. vol. 71: 2709-2717.*

* cited by examiner

*Primary Examiner* — Amy Juedes
(74) *Attorney, Agent, or Firm* — Benjamin Aaron Adler

(57) ABSTRACT

The present invention is directed to the examination of the pattern of immunodominant CD8 T cell epitopes in the E6 and E7 protein of Human Papillomavirus (HPV) and its further characterization in terms of its amino acid sequence and HLA restriction. These epitopes are identified based on their ability to induce strong CD8 T cell response and therefore, are important as sources of antigens for dendritic cell immunotherapy to treat cervical cancer. The present invention contemplates identifying a number of similar epitopes restricted by a wide variety of HLA types so that they can be used in concert to develop a preventative vaccine, which can be used for general population.

4 Claims, 22 Drawing Sheets

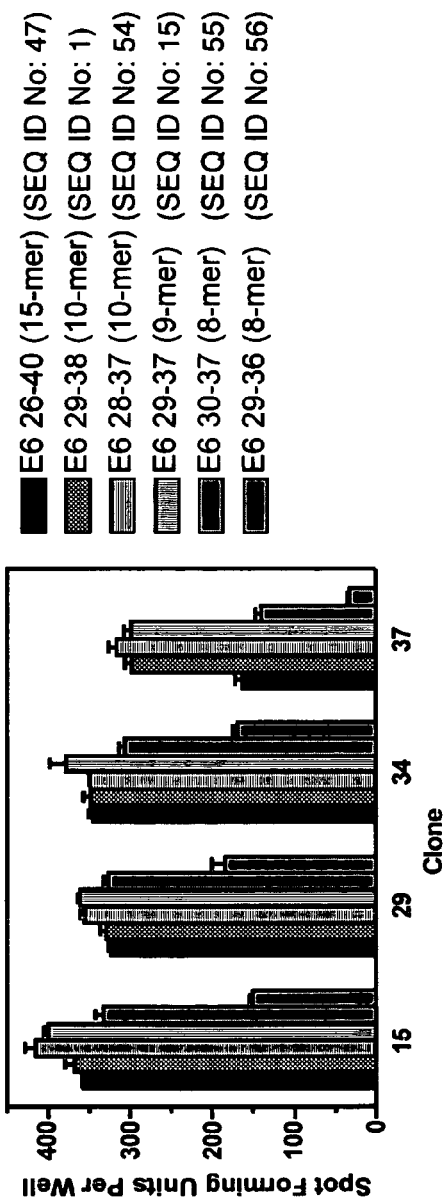
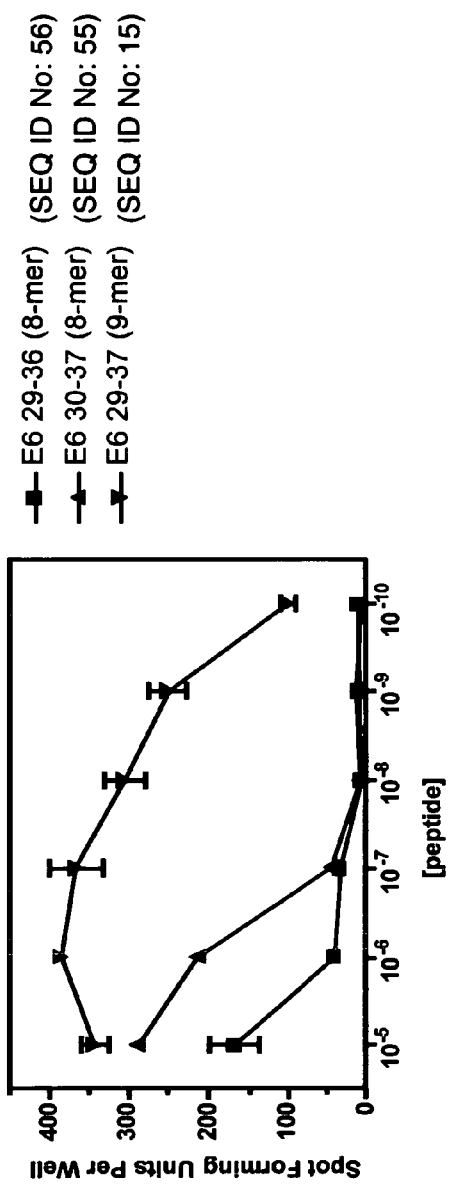
Fig. 5A
Fig. 5B

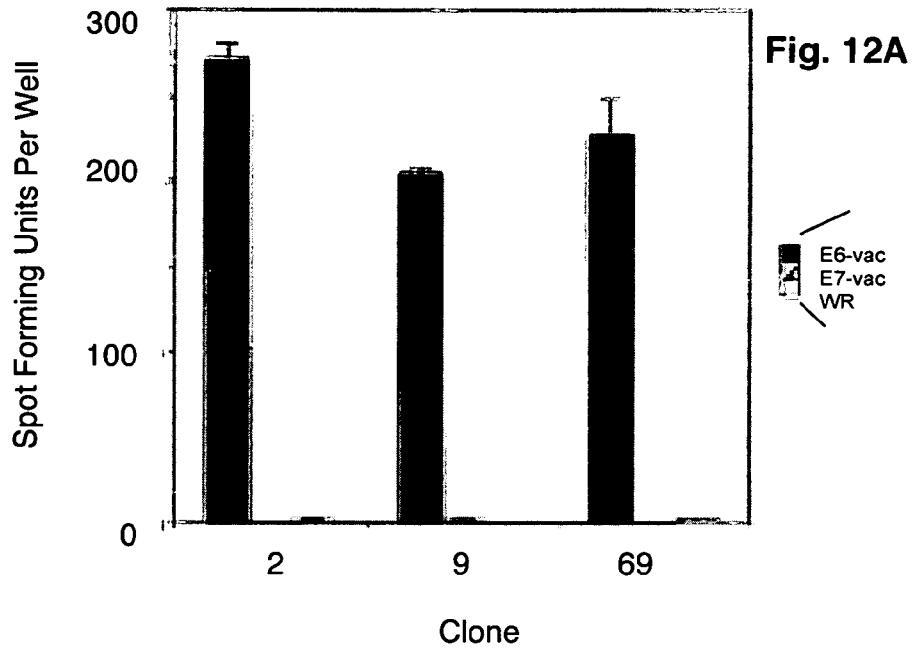
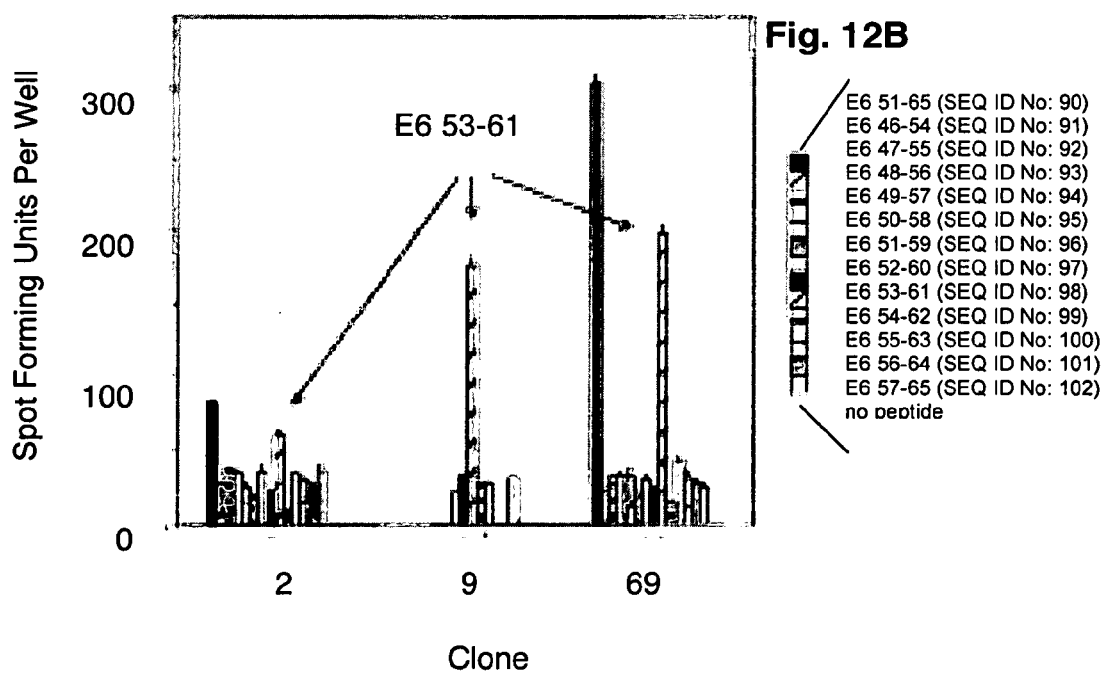
* E6 51-65 (SEQ ID NO. 90), E6 56-64 (SEQ ID NO. 101) and E6 57-65 (SEQ ID NO. 102) not tested

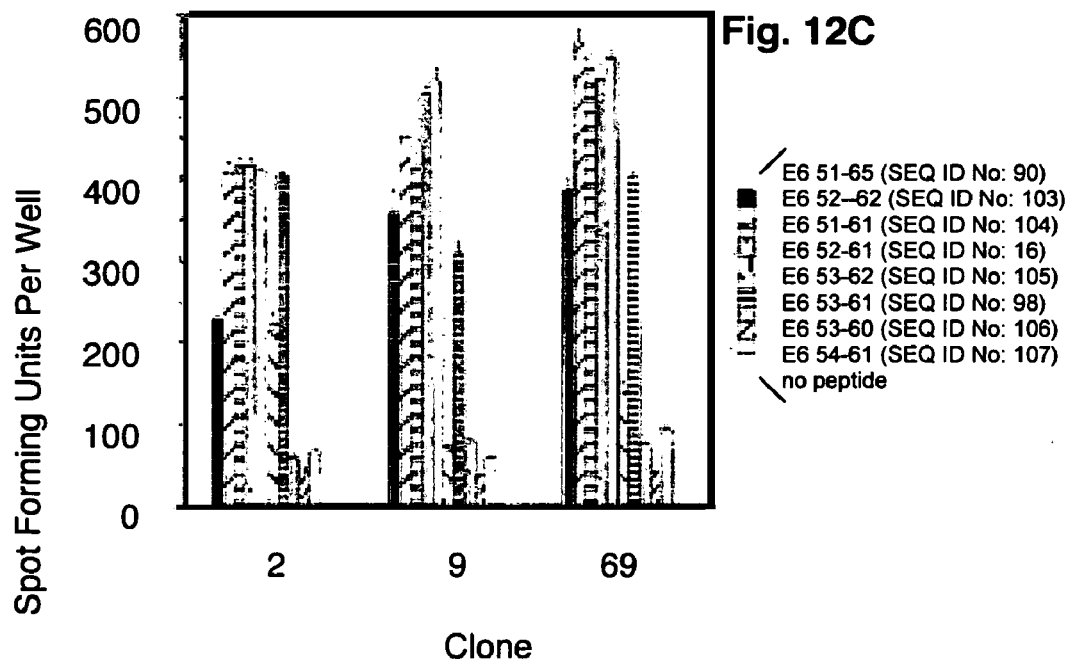
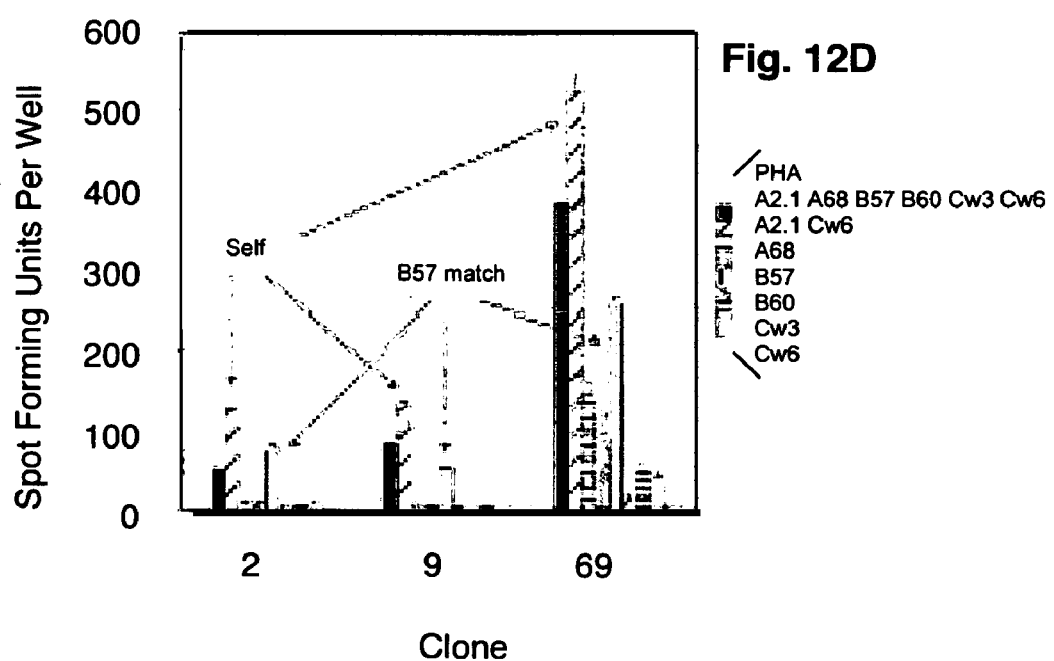

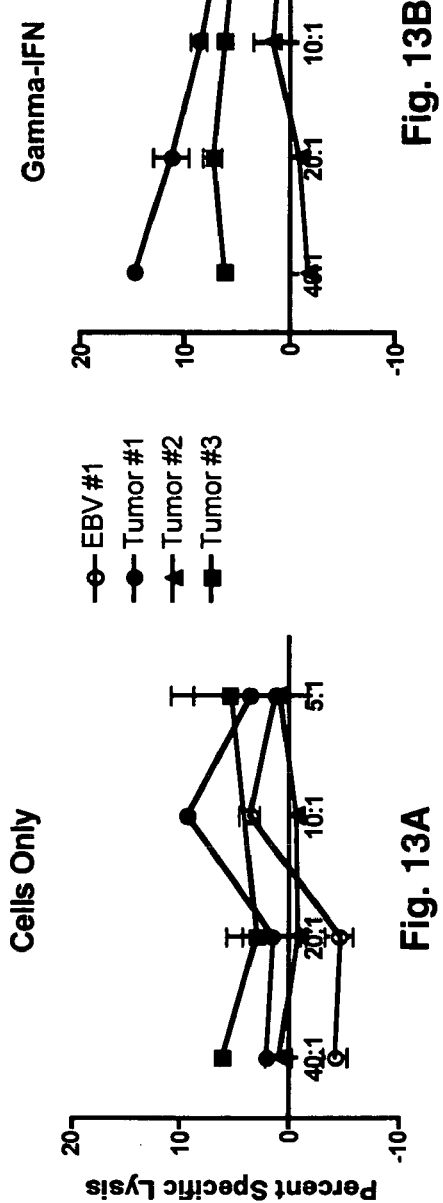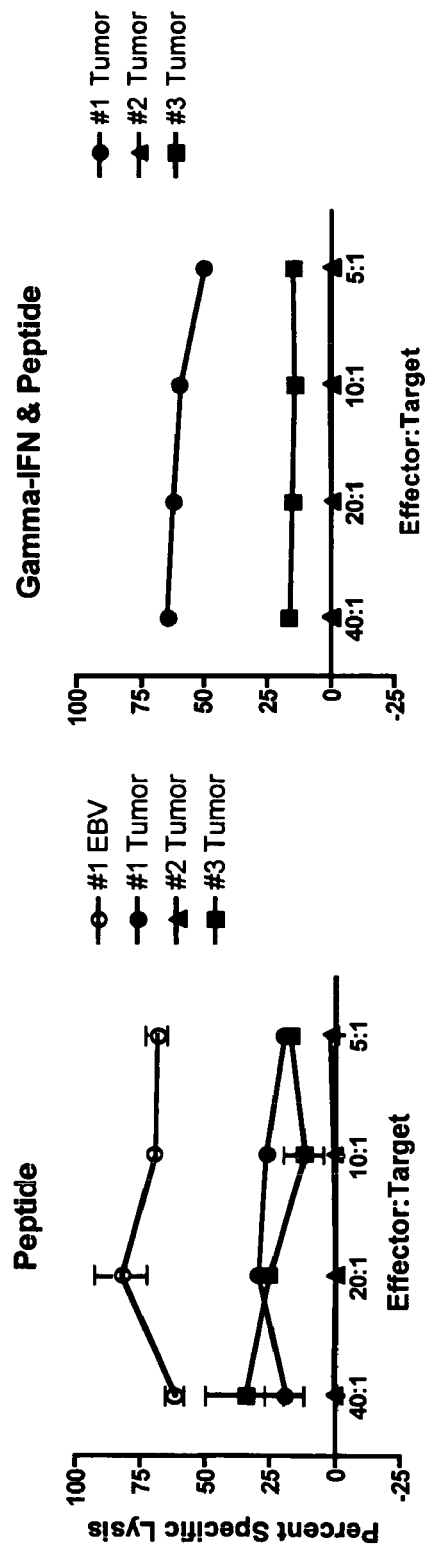
Fig. 13A Fig. 13B Fig. 13C Fig. 13D

E6 26-40 (SEQ ID NO. 47); E6 28-37 (SEQ ID NO. 54); E6 29-38 (SEQ ID NO. 1); E6 26-34 (SEQ ID NO. 48); E6 27-35 (SEQ ID NO. 49); E6 28-36 (SEQ ID NO. 50); E6 29-37 (SEQ ID NO. 15); E6 30-38 (SEQ ID NO. 51); E6 31-39 (SEQ ID NO. 52); E6 32-40 (SEQ ID NO. 53); E6 29-36 (SEQ ID NO. 17); E6 30-37 (SEQ ID NO. 55); E6 28-38 (SEQ ID NO. 192); E6 29-39 (SEQ ID NO. 193); E6 30-39 (SEQ ID NO. 188); E6 31-38 (SEQ ID NO. 104); E6 51-61 (SEQ ID NO. 90); E6 51-65 (SEQ ID NO. 104); E6 52-62 (SEQ ID NO. 103); E6 52-61 (SEQ ID NO. 16); E6 53-62 (SEQ ID NO. 105); E6 51-59 (SEQ ID NO. 96); E6 52-60 (SEQ ID NO. 97); E6 53-61 (SEQ ID NO. 98); E6 54-62 (SEQ ID NO. 99); E6 55-63 (SEQ ID NO. 100); E6 56-64 (SEQ ID NO. 101); E6 57-65 (SEQ ID NO. 102); E6 53-60 (SEQ ID NO. 106); E6 54-61 (SEQ ID NO. 107)

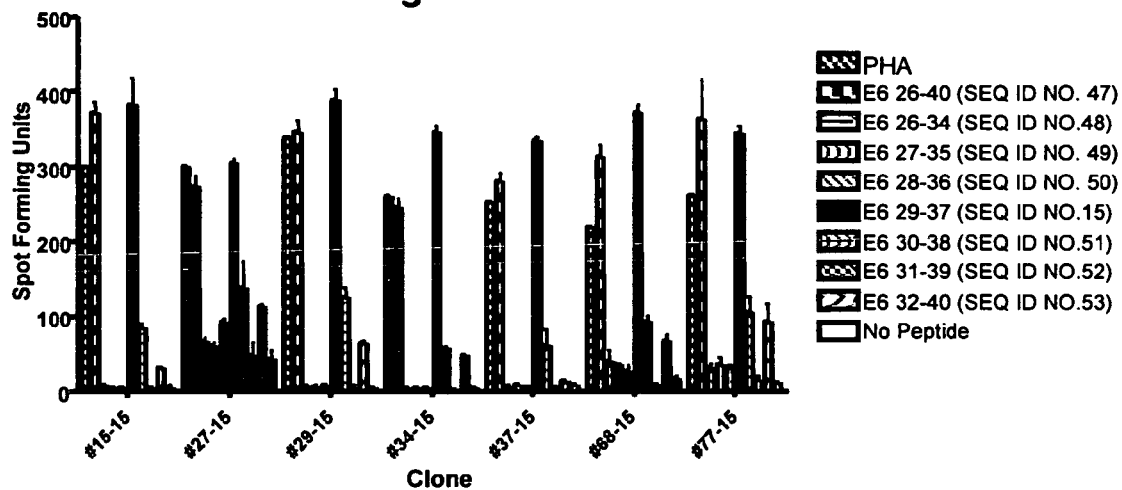
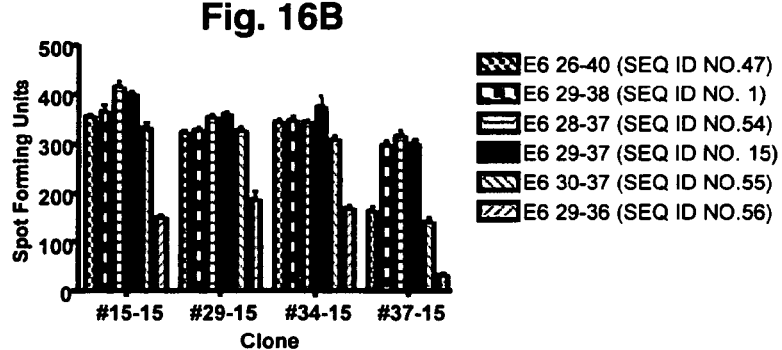
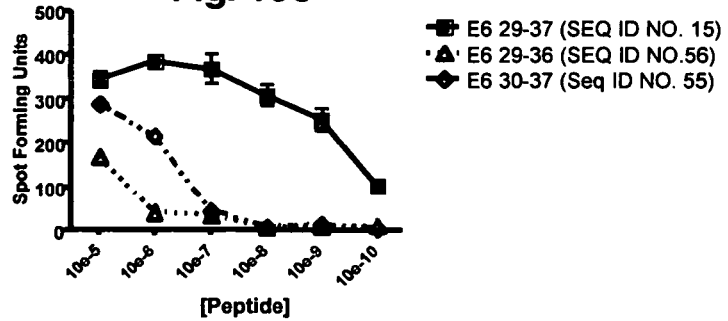

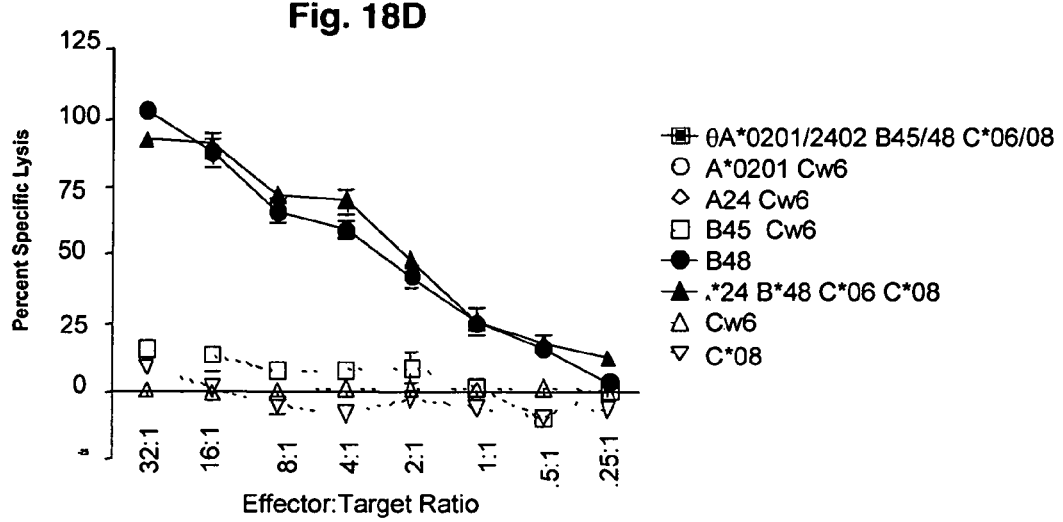
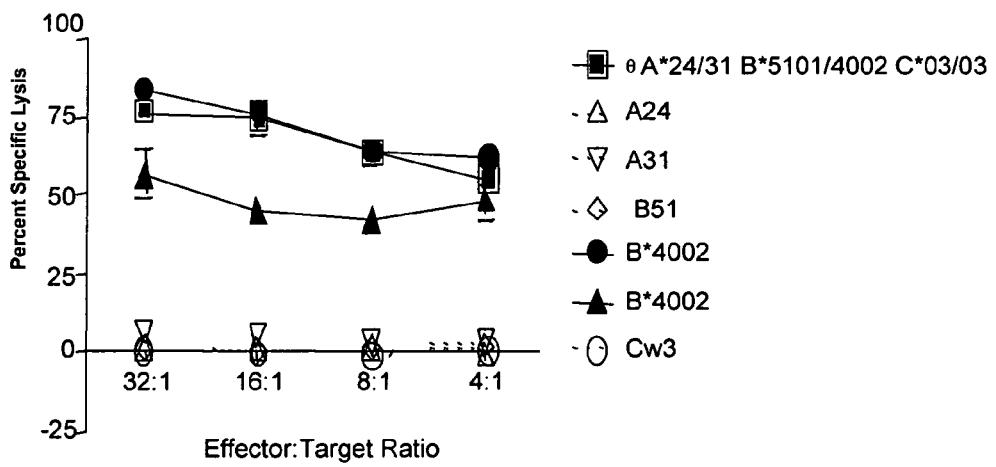

# CD8 T CELL EPITOPES IN HPV 16 E6 AND E7 PROTEINS AND USES THEREOF

CROSS REFERENCE TO RELATED APPLICATION

This non-provisional application claims benefit of provisional application U.S. Ser. No. 60/648,496 filed on Jan. 31, 2005, now abandoned.

FEDERAL FUNDING LEGEND

This invention was produced using funds from Federal government under grant no. NCI CA51323, NCI K07 CA75974, and M01RR01271 from the National Institutes of Health. Accordingly, the Federal government has certain rights in this invention.

BACKGROUND OF THE INVENTION

1. Field of the Invention

The present invention relates generally to the field of immunology. More specifically, the present invention involves identification of dominant CD8 T cell epitope in the Human Papillomavirus (HPV) proteins and its use in treating cancer such as cervical cancer.

2. Description of the Related Art

Cervical cancer is the second most common malignancy among women worldwide (World Health Organization, 1990) with 400,000 new cases being diagnosed annually (Parkin, D. et al., 1999). Annually 12,000 to 14,000 new cases of squamous cell cancer of the cervix are reported in the United States (Silverberg, E. and Lubera, J., 1988), resulting in about 3,500 deaths per year. The link between human papilloma virus (HPV) and the development of cervical cancer is well known. Among the over one hundred different types of HPV, at least 15 are strongly associated with invasive squamous cell cancer of the cervix (Munoz, N. et al., 2003). HPV16 is the one most commonly found associated with this cancer (Beaudenon et al., 1986; Crum et al., 1985).

HPV infection is also associated with the precursor lesion of cervical cancer, squamous intraepithelial lesion (SIL) (Beaudenon, et al., 1986; Crum et al., 1985; Reid, R., 1987; Lorincz et al., 1986; Lorincz et al., 1987; Fuchs, et al., 1988). While most low-grade squamous intraepithelial lesions prospectively regress spontaneously (Koutsky et al., 1992; Richart and Barron, 1969), some progress to high-grade squamous intraepithelial lesions. These high-grade lesions, in particular, cervical intraepithelial neoplasia 3 (CIN-3) are associated with a high rate progression to invasive cervical cancer (Nash et al., 1987; Campion et al., 1986).

Transformation to a malignant phenotype by HPV is mediated by two early gene products, E6 and E7. Both of these viral proteins have been shown to interact with the products of cellular human tumor suppressor genes. The E6 protein can bind and promote degradation of cell-encoded p53, while the E7 protein interacts with the retinoblastoma susceptibility gene product (Crook et al., 1991; Heck et al., 1992; Scheffner et al., 1990). The expression of E6 and E7 open reading frames has been shown to be necessary and sufficient for transformation of human cells by HPV 16 (Schlegel, R. et al., 1988; Storey, A. et al., 1988; Pirisi, L. et al., 1987). Therefore, the E6 and E7 proteins can serve as potential targets when developing new preventative and therapeutic modalities.

Cell-mediated immunity has been shown to play an important role in controlling HPV infection and HPV-associated diseases. CD8-positive, MHC class I-restricted cytotoxic T lymphocytes (CTLs) are known to be responsible for recognizing and killing virus-infected host cells and virus-induced tumors (Greenberg, P. D., 1991). Immunohistochemical analyses of squamous intraepithelial lesions and cervical cancer specimens have demonstrated the presence of activated CTLs in lesions (Bontkes, H. J. et al., 1997). Studies using mouse models have demonstrated that immunization with HPV 16 E6 or E7-transfected non-tumorigenic fibroblasts can lead to regression of tumors expressing E6 or E7 respectively, and that these events are mediated by CD8-positive CTLs (Chen, L. P. et al., 1991; Chen, L. et al., 1992).

In humans, HPV16 E6 and/or E7-specific CTLs have been identified in women with cervical cancer and women with squamous intraepithelial lesions. One group stimulated the peripheral blood mononuclear cells (PBMCs) from cervical cancer patients with an HLA-A2-restricted HPV16 E7 peptide (E7 11-20, SEQ ID NO: 3) and demonstrated that CTLs were capable of lysing HLA-matched HPV16 E7 11-20 (SEQ ID NO: 3)-pulsed targets in two of three patients (Alexander et al., 1996). Another group identified HPV-specific CTLs in lymph nodes and tumors of cervical cancer patients (Evans et al., 1997). In some patients with squamous intraepithelial lesions, CTLs to HPV16 E6 and E7 were demonstrated in PBMCs stimulated in vitro with the cervical carcinoma line CaSki (Evans et al., 1996).

HPV16 E6 and E7-specific CTLs have also been demonstrated in subjects who had evidence of HPV16 infection but who had not developed squamous intraepithelial lesions. In a small cross-sectional study, the percentage of subjects who demonstrated HPV16 E6 and/or E7-specific CTLs was higher in a group of women with HPV16 infection who had not developed squamous intraepithelial lesions, compared to a group of women with HPV16 infection who had developed squamous intraepithelial lesions. The effector cell phenotypes in these women who had not developed squamous intraepithelial lesions were shown to be CD4- and CD8-positive T lymphocytes. In women with PCR-detected cervical HPV16 infection, the association between HPV16 E6 and E7-specific CTLs and HPV16 persistence was examined using a longitudinal study design involving multiple CTL assays (Nakagawa, M. et al., 2002). Lack of CTL response to the HPV16 E6 protein but not the E7 protein was correlated with persistent HPV16 infection, suggesting that CTL responses to E6 and E7 are likely to be important at different stages during the course of infection. These studies suggested that the development of cervical cancer may due to insufficient cell-mediated immunity to HPV and that one of the possible modalities for treatment of cervical cancer may be enhancing such response as would be done in dendritic cell immunotherapy.

CD8-positive CTL recognize foreign peptides that are 8 to 11 amino acids in length and bound to and presented by HLA class 1 molecules. These peptides are called T cell epitopes. Both mouse (Ressing, M. E. et al., 1995; Sadovnikova, E. et al., 1994) and human (Ressing et al., 1995: Tarpey, I. et al., 1994) systems have been used to identify the antigenic epitopes of HPV. One group identified the potential CTL epitopes of HPV16 E6 and E7 proteins for five common HLA types by measuring binding of each of the 150 nonamer peptides using purified HLA molecules and radlolabeled peptides (Kest, W. M. et al., 1994). The immunogenicity of 9 of these potential antigenic epitopes for HLA-2.1 was tested (Ressing, M. E. et al., 1995). In vivo, 4 immunogenic peptides were identified (E6 29-38 (SEQ ID NO: 1), E7 11-20 (SEQ ID NO: 3), E7 (82-90) and E7 (86-93)) using HLA-2.1 transgenic mice. Additionally, in vitro CTL induction of human PBMCs confirmed the immunogenicity of 3 of the 4 peptides (E7 11-20 (SEQ ID NO: 3), E7 (82-90) and E7 (86-93)). CTLs to one of these peptides, E7 11-20 (SEQ ID NO: 3) have been demonstrated in patients with SIL and in cancer patients. However, since responses to this peptide were found in cancer patients, it is not clear whether this peptide played a protective role.

Another study identified antigenic epitopes of HPV16 E6 and E7 proteins by using overlapping peptides of these proteins to stimulate PBMCs from a healthy donor and binding assays to find candidate epitopes (Bourgault Villada, I. et al., 2000). This approach enabled the Identification of HLA-B18 epitopes, E6 80-88 (ISEYRHYCY; SEQ ID NO: 2) and E7 44-52 (QAEPDRAHY; SEQ ID NO: 4). It was also shown that E6 (80-88) was a naturally processed epitope that could be recognized by T cells from a patient with HSIL. Although the binding of the peptide to the HLA molecule was demonstrated, the strength of the T cell response to these antigenic epitopes compared with other T cell epitopes was not assessed. Since response to E6 80-88 (SEQ ID NO: 2) epitope was demonstrated in patient who had developed high-grade SIL, it was not clear whether this peptide had a protective effect.

Additionally, some work has also been carried out to identify antigenic epitopes of another common high-risk type, HPV 18. Using the same approach as was taken for HPV16, HLA-A2.1 binding synthetic peptides of HPV18 E6 protein were identified (Yoon, H. et al., 1998). Some of these binding peptides were also shown to be antigenic by demonstrating in vitro cytotoxicity (Table 1). An HLA-Cw4-restricted HPV18 L1 epitope, NVFPIFLQM (SEQ ID NO: 14) was identified by eluting and sequencing peptides from purified class I MHC molecules of a cervical cell line (Garcia, A. M. at al., 1999).

Table 1 lists a small number of HPV CD8 T lymphocyte epitopes shown to be antigenic in human experimental systems by demonstrating peptide-specific cytotoxicity. Except for the HLA-B18-restricted epitopes identified by Bourgault Villada et al., all were pre-selected for the given HLA types. None of the antigenic epitopes were identified based on the magnitude of T cell response regardless of the restricting HLA molecules.

TABLE 1

High-risk HPV peptide antigens for CD8 T lymphocytes shown to be antigenic in human experimental systems by demonstrating peptide-specific cytotoxicity or γ-IFN secretion.

| HPV TYPE | PEPTIDE | HLA TYPE | SEQUENCE | SEQ. ID. NO. |
|---|---|---|---|---|
| HPV16 | E6 29-38 | A2.1 | TIHDIILECV | 1 |
| | E6 80-88 | B18 | ISEYRHYCY | 2 |
| | E7 11-20 | A2.1 | YMLDLQPETT | 3 |
| | E7 44-52 | B18 | QAEPDRAHY | 4 |
| | E7 82-90 | A2.1 | LLMGTLGIV | 5 |
| | E7 86-93 | A2.1 | TLGIVCPI | 6 |
| | L1 323-331 | A2.1 | ICWGNQLFV | 7 |
| HPV18 | E6 24-33 | A2.1 | SLQDIEITCV | 8 |
| | E6 25-33 | A2.1 | LQDIEITCV | 9 |
| | E6 40-48 | A2.1 | ELTEVFEFA | 10 |
| | E6 47-55 | A2.1 | FAFKDLFVV | 11 |
| | E6 92-101 | A2.1 | KLTNTGLYNL | 12 |
| | E6 13-21 | A2.1 | KLPDLCTEL | 13 |
| | L1 54-62 | Cw4 | NVFPIFLQM | 14 |

Dendritic cells are the most potent antigen-presenting cells and are capable of sensitizing T cells to new and recall antigens (Fong, L. et al., 2001). Recent advances in the knowledge of dendritic cell differentiation steps and in the technical abilities to prepare them in a large quantity enabled development of immunotherapy protocols for the treatment of variety of cancers. The results of clinical trials for different types of cancers have been reported but the best-studied tumors are malignant melanoma, prostate cancer, colorectal carcinoma and multiple myeloma (Ridgway, D. et al., 2003). The results of a small clinical trial of cervical cancer patients have been published in which autologous dendritic cells were pulsed with HPV16 E6 or HPV1 8 E7 protein (Ferrera et al., 2003). Although the therapy was well-tolerated and there was evidence of humoral and cell-mediated immune responses in some patients, no objective clinical response was reported.

Thus, prior art is deficient in peptide antigens derived from the HPV16 E6 and E7 proteins that have been identified based on the magnitude of T cell responses to be used as sources of antigens for dendritic cell immunotherapy for cervical cancer. The present invention fulfills this long-standing need and desire in the art.

SUMMARY OF THE INVENTION

In one embodiment of the present invention, there is a method of determining a pattern of immunodominant T cell epitopes within an HPV protein in an individual. This method comprises stimulating T cell line of an individual in vitro with autologous dendritic cells infected with a recombinant virus expressing the protein. The stimulated T cells are then incubated with a first set of peptides and the magnitude of T cell response in the incubated cells is determined. The peptides that induce strong T cell response are identified, where the sequence of the peptides correspond to a region within the protein. Thus, the pattern of the immunodominant T cell epitopes within the HPV protein is determined.

In another embodiment of the present invention, there is provided a synthetic peptide having sequences corresponding to peptides of first set, second set, third set and the immunodominant CD8 T cell epitope. In yet another embodiment of the present invention, there is provided a method of immunotherapy directed towards HPV protein in an individual. This method comprises isolating immune cells from the individual and pulsing the isolated immune cells with the peptide comprising one or more than one immunodominant T cell epitope identified herein. The pulsed immune cells are then transferred back to the individual, where the immune cells activate HPV-specific immune response in the individual, thereby generating immunotherapy targeted towards the HPV protein in the individual. In still another embodiment of the present invention, there is provided an immunogenic composition comprising a sequence or a combination of sequences of the immunodominant T cell epitope and an adjuvant. In yet another embodiment of the present invention, there is provided a method of preventing or treating a pathophysiological condition involving expression of HPV protein in an individual. Such a method comprises administering the immunogenic composition identified herein, where the composition activates HPV-specific immune response in the individual, thereby treating the pathophysiological condition in the individual.

BRIEF DESCRIPTION OF THE DRAWINGS

FIG. 2A shows ten screen-positive T cell clones with E6 26-40 (SEQ ID NO: 47) confirming their specificity. FIG. 2B shows four screen-positive T cell clones with E6 16-30 (SEQ ID NO: 45) or E6 21-35 (SEQ ID NO: 46) that were false positives.

FIGS. 5A-B identify the shortest and the most optimal amino acid sequence of the CD8 T cell epitope of subject 15. FIG. 5A compares E6 26-40, SEQ ID NO: 47), E6 29-387 SEQ ID NO: 1), E6 28-37 (SEQ ID NO: 54), E6 29-37 (SEQ ID NO: 15), E6 30-37 (SEQ ID NO: 55) and E6 29-36 (SEQ ID NO: 56) using an ELISPOT assay, which revealed that the optimal peptide of minimum length was E6 29-37 (SEQ ID NO: 15). One thousand T cell clones were plated in triplicate along with $10^5$ autologous EBV-LCL cells. FIG. 5B compares E6 29-37 (SEQ ID NO: 15), E6 30-37 (SEQ ID NO: 55) and E6 29-36 (SEQ ID NO: 56), ranging from $10^{-5}$M to $10^{-10}$M, using an ELISPOT assay. This assay confirmed that the optimal peptide of minimum length was E6 29-37 (SEQ ID NO: 15). A total of thousand T cell clones were plated in triplicate along with $10^5$ autologous EBV-LCL cells.

FIG. 6A shows results of an ELISPOT assay demonstrating that the restriction element for the E6 29-37 (SEQ ID NO: 15) epitope was HLA-B48 molecule. A total of 1000 T cell clones were plated in triplicate along with $10^5$ EBV-LCL cells matching at the designated HLA types. FIG. 6B shows results of chromium release assay confirming that the restriction element for the E6 29-37 (SEQ ID NO: 15) epitope was HLA-B48 molecule.

FIG. 8A shows that the E7 7-15 (SEQ ID NO: 18) specific T cell clones recognize the E7 7-15 (SEQ ID NO: 18) peptide but not E7-vac-infected autologous EBV-LCL. A total of $10^3$ T cell clones were plated with $10^5$ autologous EBV-LCL. FIG. 8B shows the results suggesting that the restriction element for the E7 7-15 (SEQ ID NO: 18) peptide was the HLA-B48 molecule. A total of $10^3$ T cell clones were plated along with $10^5$ EBV-LCL matching at the designated HLA types. Only the HLA class I molecules matching the subject being studied are indicated.

FIG. 9A shows that E7 11-20 (SEQ ID No: 3) specific T cell clones recognize the E7 11-20 (SEQ ID NO: 3) peptide but not the E7 11-19 (SEQ ID NO: 57) peptide, the E7 12-20 (SEQ ID NO: 58) peptide of the E7-vac-infected autologous EBV-LCL. A total of $10^3$ T cell clones were plated along with $10^5$ autologous EBV-LCL. FIG. 9B shows the restriction element for E7 11-20 (SEQ ID NO: 3) was the HLA-A2.1 molecule. A total of $10^3$ T cell clones were plated along with $10^5$ EBV-LCL matching at the designated HLA types.

FIG. 11A shows that the chromium release assay demonstrated the specificity of the 27G6 clone for an epitope from the E7 protein. FIG. 11B shows that the ELISPOT assay using overtapping 15-mer peptides of E7 demonstrated that the antigenic peptide is contained within the E7 76-90 (SEQ ID NO: 80) region. A total of $10^3$ T cell clones were plated along with $10^5$ autologous EBV-LCL. FIG. 11C shows that an ELISPOT assay using Overlapping 9-mer peptides within the E7 76-90 (SEQ ID NO: 80) region demonstrated a response only with the E7 79-87 (SEQ ID NO: 19) peptide. A total of $10^3$ T cell clones were plated along with $10^5$ autologous EBV-LCL. FIG. 11D compares the E7 76-90 (SEQ ID NO: 80), E7 79-87 (SEQ ID NO: 19), E7 79-86 (SEQ ID NO: 88) and E7 80-87 (SEQ ID NO: 39) by an ELISPOT assay and shows that an optimal response was obtained with E7 79-87 (SEQ ID NO: 19). A total of $10^3$ T cell clones were plated along with $10^5$ autologous EBV-LCL. FIG. 11E shows the restriction element for the 27G6 clone to be the HLA-B60 molecule by an ELISPOT assay. A total of $10^3$ T cell clones were plated along with $10^3$ EBV-LCL matching at designated HLA types. FIG. 11F shows that the E7 76-90 (SEQ ID NO: 80) and E7 79-87 (SEQ ID NO: 19) peptides were much more vigorously recognized than were the E7 79-86 (SEQ ID NO: 88) and E7 80-87 (SEQ ID NO: 89) peptides using chromium release assay where E:T ratio is the effector to target cell ratio.

FIGS. 12A-D show the results of ELISPOT assay performed to characterize the E6 epitope from subject 1. FIG. 12A shows that T cell clones 2, 9 and 89 recognized an E6 epitope, which was naturally processed. A total of $10^3$ T cell clones were plated along with $10^3$ autologous EBV-LCL infected with E6-vac, E7-vac and WR respectively. FIG. 12B shows a response with the E6 53-61 (SEQ ID NO: 98) peptide in an ELISPOT assay using overlapping 9-mer peptides within the E6 46-70 (SEQ ID NO: 38) region. A total of $10^3$ T cell clones were plated along with $10^5$ autologous EBV-LCL. FIG. 12C compares E6 51-65 (SEQ ID NO: NO 90), E6 52-62 (SEQ ID NO: 103), E6 51-61 (SEQ ID NO: 104), E6 52-61 (SEQ ID NO: 16), E6 53-62 (SEQ ID NO: 105), E6 53-61 (SEQ ID NO: 98), E6 53-60 (SEQ ID NO: 106) and E6 54-61 (SEQ ID NO: 107) using an ELISPOT assay and shows that the optimal peptide of minimum length was E6 52-61 (SEQ ID NO: 16). A total of $10^3$ T cell clones were plated along with 10⁵ autologous EBV-LCL. FIG. 12D shows restriction element for E6 52-61 (SEQ ID NO: 16) epltope was HLA-B57 molecule using an ELISPOT assay. A total of 10³ T cell clones were plated along with 10⁵EBV-LCL matching at designated HLA types.

FIGS. 13A-D show results of a chromium release assay examining the expression of the E6 52-61 (SEQ ID NO: 16) CD8 T cell epitopes by primary tumor cell lines derived from cervical cancer patients. EBV-LCL was available from patient#1. FIG. 13A shows percent specific lysis of untreated cells. FIG. 13B shows percent specific lysis of cells treated with IFN-γ, FIG. 13C shows percent specific lysis of cells pulsed with E6 52-61 (SEQ ID NO: 16) peptide and FIG. 13D shows percent specific lysis of cells pulsed with peptide and treated with IFN-γ. The experiment was performed in triplicate and the error bars represent standard deviations.

FIG. 14A shows that all twenty of the T cell clones from subject 7 that screened positive for the E6 16-40 (SEQ ID NO: 36) region were positive for a naturally processed E6 epitope. Ten representative clones (MOI 5) are shown. FIG. 14B shows that 6 of 10 T cell clones (MOI 5) from subject 7 that screened positive for the E6 46-70 (SEQ ID NO: 38) region were positive for a naturally processed E6 epitope. FIG. 14C shows that 10 of the 14 T cell clones from subject 15 that screened positive for the E6 18-40 (SEQ ID NO: 36) region were positive for a naturally processed E6 epitope. Four representative clones (MOI 10) are shown. FIG. 14D shows that all eight of the T cell clones (MOI 5) from subject 20 that screened positive for the E6 16-40 (SEQ ID NO: 36) region were positive for a naturally processed E6 epitope. FIG. 14E shows that 6 of the 8 T cell clones (MOI 5) from subject 20 that screened positive for the E6 31-55 (SEQ ID NO: 37) region were positive for a naturally processed E6 epitope (MOI 5).

FIG. 15A shows that two of three T cell clones demonstrated the most number of spot forming units with E6 29-38 (SEQ ID NO: 1) among all the other peptides that were tested. FIG. 15B compares E6 28-38 (SEQ ID NO: 192), E6 29-39 (SEQ ID NO: 193), E6 28-37 (SEQ ID NO: 54), E6 29-38 (SEQ ID NO: 1), E6 29-37 (SEQ ID NO: 15), E6 30-38 (SEQ ID NO: 51), E6 29-36 (SEQ ID NO: 56), E6 30-37 (SEQ ID NO: 55), and E6 31-38 (SEQ ID NO: 17) and shows that the optimal peptide of minimum length was E6 29-38 (SEQ ID NO: 1). FIG. 15C shows that two of four T cell clones demonstrated the most number of spot forming units with E6 52-61 (SEQ ID NO: 16) among all the peptides that were tested. FIG. 15D compares E6 51-61 (SEQ ID NO: 104), E6 52-62 (SEQ ID NO: 103), and E6 52-61 (SEQ ID NO: 16), ranging from $10^{-5}$M to $10^{-10}$ M, and shows that the optimal peptide of minimum length was the E6 52-61 (SEQ ID NO: 16) peptide. The results of one representative clone (#86-7) out of two clones tested is shown.

FIGS. 16A-C show results of ELISPOT assays demonstrating that the shortest and optimal peptide for subject 15's dominant epitope was E6 29-37 (SEQ ID NO: 15), FIG. 16A shows that all seven of T cell clones demonstrated the most number of spot forming units with E6 29-37 (SEQ ID NO: 1) among all the peptides that were tested. FIG. 16B compares E6 26-40 (SEQ ID NO: 47), E6 29-38 (SEQ ID NO: 1), E6 28-37 (SEQ ID NO: 54), E6 29-37 (SEQ ID NO: NO, 15), E6 30-37 (SEQ ID NO: 55), and E6 29-36 (SEQ ID v 56) and shows that the optimal peptide of minimum length was E6 29-37 (SEQ ID NO: 15). FIG. 16C compares E6 29-37 (SEQ ID NO: 15), E6 30-37 (SEQ ID NO: 55), and E6 29-36 (SEQ ID NO: 56), ranging from $10^{-5}$M to $10^{-10}$ M, and confirms that the optimal peptide of minimum length was E6 29-37 (SEQ ID NO: 15). The results of one (#15-15) representative clone out of four clones tested is shown.

FIG. 17A shows large numbers of spot forming units for clone #60-20 with E6 30-38 (SEQ ID NO: 51) and E6 31-39 (SEQ ID NO: 52) among the other peptides that were tested. FIG. 17B shows large numbers of spot forming units with E6 30-38 (SEQ ID NO: 51) and E6 31-39 (SEQ ID NO: 52) among the other peptides that were tested for clones #127-20 and #138-20. FIG. 17C compares E6 30-39 (SEQ ID NO: 188), E6 30-38 (SEQ ID NO: 51), E6 31-39 (SEQ ID NO: 52), E6 30-37 (SEQ ID NO: 55), E6 31-38 (SEQ ID NO: 17), E6 31-37 (SEQ ID NO: 186), and E6 32-38 (SEQ ID NO: 187) and shows that the optimal peptide of minimum length was E6 31-38 (SEQ ID NO: 17). FIG. 17D compares E6 30-39 (SEQ ID NO: 188), E6 30-38 (SEQ ID NO NO 51), and E6 31-39 (SEQ ID NO: 52), ranging from $10^{-5}$M to $10^{-8}$ M, and shows that the optimal peptide of minimum length was E6 30-38 (SEQ ID NO: 51). FIG. 17E compares E6 30-39 (SEQ ID NO: 188), E6 30-38 (SEQ ID NO: 51), and 66 31-38 (SEQ ID NO: 17), ranging from $10^{-5}$M to $10^{-10}$ M, and shows that the optimal peptide of minimum length was E6 31-38 (SEQ ID NO: 17). The results with one (#60-20) representative clone out of two clones tested are shown.

FIGS. 18A-E show the restricting HLA class I molecule for the CD8 T-cell epitope using chromium release assays. θ indicates autologous LCL. HLA types determined using one of the molecular methods is indicated by *. FIG. 18A shows that the E6 29-38 epitope (SEQ ID NO: 1) was restricted by the A0201 molecule. A representative (#59-7) of two clones is shown. FIG. 18B shows that the E6 29-38 epitope (SEQ ID NO: 1) was restricted by the A0201 molecule, but only with homozygous expression. A representative (#59-7) of two clones is shown. FIG. 18C shows that the E6 52-61 epitope (SEQ ID NO: 16) was restricted by the B35 molecule. A representative (#86-7) of two clones is shown. FIG. 18D shows that the E6 29-38 epitope (SEQ ID NO: 1) was restricted by the B48 molecule. A representative (#34-15) of the two clones is shown. FIG. 18E shows that the E6 31-38 epitope (SEQ ID NO: 17) was restricted by the B4002 molecule. A representative (#127-20) of three clones is shown.

DETAILED DESCRIPTION OF THE INVENTION

Figure 1:
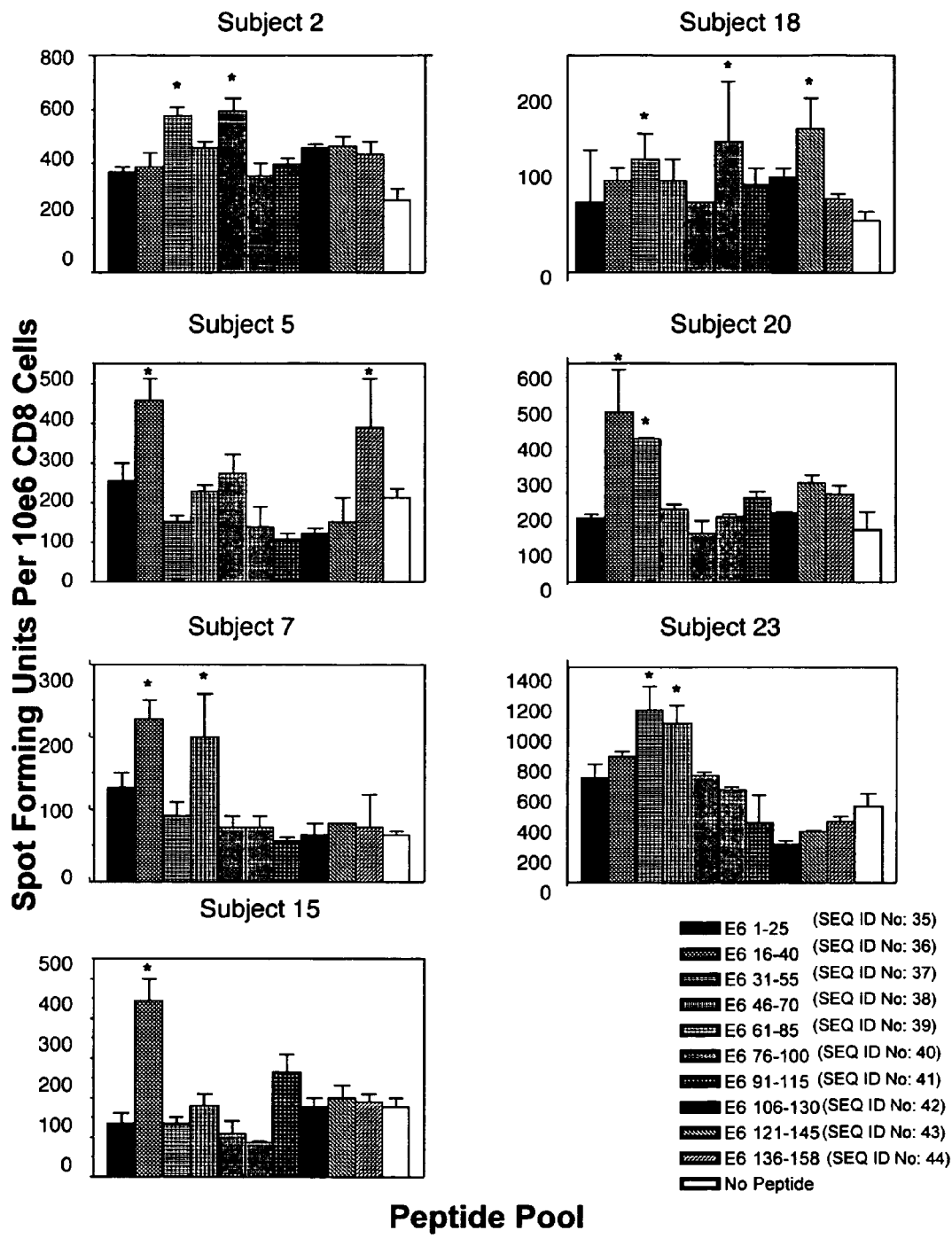
FIG. 1 shows results of ELISPOT assays showing the pattern of CD8 T cell immunodominance within HPV16 E6 protein in women who were able to clear their HPV16 infection. The results of subjects who had at least one positive peptide pool are shown, except for subject 1 whose data has been previously described (Nakagawa, M et al., ). (*) indicates a positive peptide pool.

Human papillomavirus type 16 (HPV16) is a high-risk type human papillomavirus most commonly associated with the squamous cell carcinoma of the cervix. The E6 protein is one of the two oncoproteins utilized by HPV16 for transformation and functions by binding and degrading p53. Although the exact mechanism leading from HPV infection to malignancy are unknown, one of the critical steps in the progression to malignancy appears to be persistence of infection. Previous studies had demonstrated that women with persistent HPV16 infection did not have detectable CTL responses compared to over one-half of those whose infection had cleared.

The present invention examined the pattern of CD8 T cell epitopes in the HPV16 E6 protein recognized by T lymphocytes from women who had cleared HPV16 cervical infection by isolating and culturing T cells in vitro. Enzyme-linked immunospot (ELISPOT) assay was then performed to identify a region within the E6 protein, which contained the dominant as well as subdominant epitope. Then, T cell clones with the specificity to the dominant epitope were isolated on the basis of IFN-γ secretion.

One-third of the women tested showed the presence of one or more potential CD8 T cell epitopes. The dominant epitopes (i.e. forming the greatest number of spot-forming units) were found in the amino acid region 16 to 40 in 4 subjects. The present invention further defined the minimum and optimal amino acid sequence of a dominant epitopes such as E6 29-37 (TIHDHLEC, SEQ ID NO: 15) restricted by HLA molecule (HLA-B48), E6 31-38 (HDIILECV, SEQ ID NO: 17) restricted by HLA-4002 molecules) and E6 29-38 (TIHDIILECV, SEQ ID NO: 1) restricted by HLA-A0201 molecule and a subdominant epitope such as E6 52-61 (SEQ ID NO: 16) restricted by HLA-B35. The E6 29-38 (SEQ ID NO: 1) restricted by HLA-A2.1, the E7 7-15 (TLHEYMLDL; SEQ ID NO: NA, 18) restricted by HLA-A2.1 and HLA-B8 molecules and E7 11-20 (SEQ ID NO: 3) restricted by HLA-A2.1 molecule were also reported by others previously. Since all the immunodominant epitopes of E6 and E7 protein were found in the N-terminal half of the protein, it suggested that the N-terminal half of the E6 or E7 protein played an important role in mounting T cell immunity and that a vaccine focusing on the N-terminal half of HPV16 E6 or E7 might be appropriate to assist in viral clearance.

Previous studies have shown that HPV16 E6 protein has extensive transformation capabilities via a variety of interactions, including (1) binding to and degradation of p53 (Wemess et al., 1990); (2) activation of telomerase (Klingelhutz, A. J. et al., 1996); and (3) interactions with the transcriptional coactivator CBPp300-binding protein (Patel et al., 1999; Zimmermann et al., 1999), human minichromosome maintenance 7 protein (Kuhne et al., 1998), interferon regulatory factor-3 (Ronco et al., 1998) and E6-targeted protein 1 (Gao et al., 1999). However, the most extensively studied mechanism of transformation involves the p53 protein. Interestingly, the N-terminal half of the E6 protein had been shown to induce p53 degradation although the C-terminal half could bind to p53 (Crook et al. 1991). Further, 43 amino acids in the N-terminal of E6 protein had been shown to be required for its binding to E6-associated protein (Pim et al., 1997). Therefore, using the N-terminal half of the E6 protein may not necessarily be safe from its oncogenic potential and smaller fragments such as T cell epitopes may be better sources of antigens for vaccines and immunotherapies.

Further, the E7 protein, a well-characterized cytoplasmic-nuclear protein with little intratypic sequence variation is as important as the E6 protein in the vaccination against HPV containing cervical cancer. HPV16 and 18 are associated with vast majority of cervical cancers and it is known that the E7 oncoprotein is important in the induction and maintenance of cellular transformation in most HPV-containing cancers. Thus, the E7 protein from HPV16 and HPV 17 is a significant target antigen in the vaccination of cervical cancer. However, all the studies reported so far have demonstrated the usefulness of full-length E7 protein in the vaccination against such cancer. One such study reported that autologous dendritic cells pulsed with the recombinant, full-length E7 protein elicited a specific CD8+ CTL response against autologous tumor target cells in patients with HPV16 or HPV18-positive cervical cancer and induced CD4+ T cell proliferative response (Santin, A. D. et al., 2002).

Another study reported that a patient diagnosed with pulmonary metastatic cervical cancer refractory to standard salvage therapy when subjected to a full course of treatment with E7-loaded dendritic cell, demonstrated strong cellular immune response in the form of DTH skin test reactions to E7 antigen (Santin et al., 2002). Although the pulmonary metastatic lesions remained stable under radiologic examination throughout the treatment, fine needle biopsy of one of the larger pulmonary lesions after 11 months revealed necrosis, fibrosis and macrophage infiltration but no tumor cells. Additionally, the treatment was well-tolerated, with no side effects or adverse events other than transient pain and induration at the sites of DC vaccination and skin testing.

Thus, considerable effort has been made to identify antigenic epitopes of HPV. However, the present invention differed from the previous studies described so far in two ways. First, the approach taken in the present invention had an advantage of being able to select T cell epitopes based on the magnitude of the T cell response. Hence, these epitopes might play a significant role in viral clearance. Second, since the present invention studied women whose HPV16 infection had become undetectable, the CD8 T cell epitopes examined were likely to be important. This importance could be further assessed by comparing responses between women who were able to clear their HPV16 infection and those in whom the infection persisted.

Additionally, the difference in the approach used by the present invention might also lead to different result. For example, it was previously reported that E6 29-38 (SEQ ID NO: 1) was an HLA-A2.1 restricted epitope (Ressing, M. E. et al., 1995). However, present invention identified the E6 29-37 (SEQ ID NO: 15) epitope as an HLA-B48 restricted epitope although the subject was HLA-A2.1 positive. Further, the possibility that the subjects of the present invention had a low level infection that was under the threshold of detection by current methods was unlikely since these subjects demonstrated PCR results negative for HPV16 in a large number of visits. Furthermore, the women studied in the present invention were examined some years after their HPV16 infection had become undetectable and the T cell responses to the key epitopes might have diminished to a level below detection. Additionally, the peptides that were synthesized were only of the HPV16 European prototype (Seedorf 1985). Although previous study had demonstrated that the HPV16 European prototype was the most commonly found type (Nakagawa et al., 2000), the T cell epitopes in women infected with other HPV16 variants might have been missed.

The method described in the present invention was also compared to two other methods for identifying antigenic peptides of HPV16 E6 and E7 proteins in women with documented HPV clearance. The first method that led to the identification of E7 7-15 (SEQ ID NO: 18) epitope, required first having the information about which peptides bind to an HLA-A2.1 molecule. Although this method should have identified an HLA-A2.1-restricted epitope, the restriction element was found to be the HLA-B48 molecule, underscoring the limitation of this method in identifying HLA-specific epitopes. The second method that led to the identification of E7 79-87 (SEQ ID NO: 19) epitope involved generation of T cell line by in vitro stimulation of CD8 cells with autologous dendritic cells infected with E6-vac and E7-vac and performing a limiting dilution assay to isolate a T cell clone before defining the peptide sequence and its associated restriction element. The latter technique was a more classical approach and many viral epitopes have been identified using this approach (Kaul and Rowland-Jones, 2000; Rickinson, and Moss, D. J., 1997).

However, this method used to identify E7 79-87 (SEQ ID NO: 19) epitope was impractical for identifying antigenic epitopes of pathogens which are expected to generate a small number of circulating T lymphocytes and thus failed to identify the E6 epitope due to low frequency of T-cell clones. The third method that was used to Identify the E6 52-61 (SEQ ID NO: 16) epitope, incorporated key technical advances which could make it feasible to identify new epitopes even when particular T lymphocytes with the specificity might be scarce. These advances included (i) using overlapping 15-mer peptides to identify the region in which the epitope is contained; (H) magnetically selecting for IFN-γ-secreting peptide-specific T lymphocytes and (iii) seeding autologous and allogeneic EBV-LCL cells for the ELISPOT assay, reducing the number of T cell clone cells required to $10^3$ cells per well.

It was observed that the E7 7-15 (SEQ ID NO: 18) and E7 11-20 (SEQ ID NO: 3) specific T cell clones In the first method did not recognize the E7-vac-infected autologous EBV-LCL (FIGS. 8A and 9A), especially since cross reactive lysis of CaSki cells (an HLA A2.1-positive cervical carcinoma cell line expressing the HPV E6 and E7 proteins) by an E7 11-20 (SEQ ID NO: 3)-specific T cell clone had been demonstrated previously (Ressing, M. E. et al., 1995). This may due to low affinity of the E7 7-15 (SEQ ID NO: 18) and E7 11-20 (SEQ ID NO: 3)-specific T cell clones identified in the present invention, since they were isolated from a peptide-stimulated T cell line. Alternatively, it was possible that these epitopes were not naturally processed in EBV-LCL, although they were processed in dendritic cells used to stimulate the T cell lines.

Figure 10:
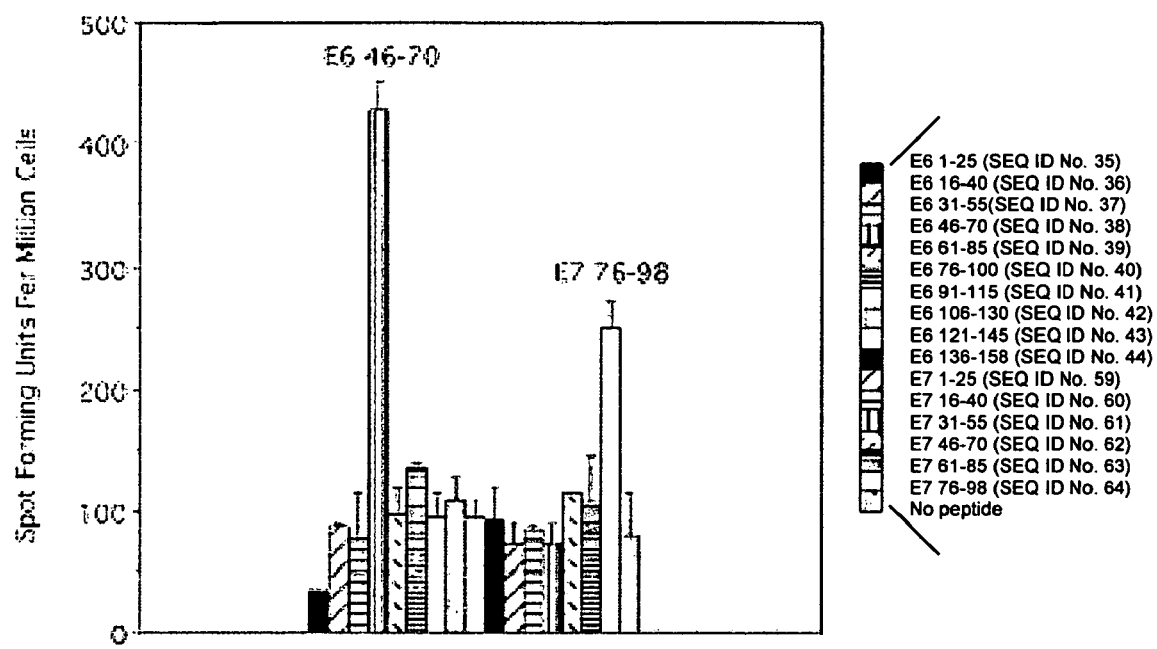
FIG. 10 shows results of ELSPOT assay performed using a CD8 T cell line from subject 1 with overlapping 15-mer peptides, in pools of three of the HPV16 E6 and E7 protein suggesting the presence of one antigenic epitope in the E6 46-70 (SEQ ID NO: 38) region and another one in the E7 76-98 (SEQ ID NO. 64) region. Each pool contained three 15-mer peptide which overlapped by 10 central amino acids. For example, the first pool, which covered the E6 1-25 (SEQ ID NO: 35) region, contained E6 1-15 (SEQ ID NO: 108), E6 6-20 (SEQ ID NO: 109), and E6 11-25 (SEQ ID NO: 110). A total of $2\times10^5$ cells from the CD8 T cell line were plated per well.

The magnitude of immune responses to the E6 and E7 proteins for subject 10 was measured using a CD8 T cell line (FIG. 10). Despite the in vitro manipulation, the repertoire of the resulting HPV16 E6- and E7-specific T cell was representative of that in natural infection, since antigenic epitopes in E6-vac and E7-vac-infected cells would be processed in the same manner as in cells infected with the whole virus. The three different epitope that were identified using the different approaches were restricted by other less common HLA types, for example, E6 52-61 (SEQ ID NO: 16) by HLA B57; E7 7-15 (SEQ ID NO: 18) by HLA B48 and E7 79-87 (SEQ ID NO: 19) by HLA B60.

Thus, the present invention demonstrated the technical feasibility of isolating T cell clones and characterizing these CD8 T cell epitopes in terms of their minimal and optimal sequence and the restricting HLA molecules. It is contemplated to evaluate the CD8 T cell epitopes from other subjects. Additionally, it is also contemplated that the cross-presentation of the peptide analogous to the HPV16 E6 52-61 (SEQ ID NO: 16) epitope by other high risk HPV types will also be examined.

TABLE 2

Amino acid sequences of peptides of high risk HPV types which are analogous to the HPV16 E6 52-61 (SEQ ID NO: 16) CD8 T cell epitope.

| HPV TYPE | AMINO ACID RESIDUES | SEQUENCE | SEQ ID NOS. |
|---|---|---|---|
| 16 | 52-61 | FAFRDLCIVY | 16 |
| 18 | 47-56 | FAFKDLFVVY | 22 |
| 31 | 45-54 | FAFTDLTIVY | 23 |
| 33 | 45-54 | FAFADLTVVY | 24 |
| 35 | 45-54 | FACYDLCIVY | 25 |
| 39 | 47-56 | FAFSDLYVVY | 26 |
| 45 | 47-56 | FAFSDLYVVY | 27 |
| 51 | 45-54 | VAFTEIKIVY | 28 |
| 52 | 45-54 | FLFTDLRIVY | 29 |
| 56 | 48-57 | FACTELKLVY | 30 |
| 58 | 45-54 | FVFADLRIVY | 31 |
| 59 | 47-56 | FAFNDLFIVY | 32 |
| 68 | 47-56 | FAFGDLNVVY | 33 |
| 73 | 45-54 | FAFSDLCIVY | 34 |

*Amino acid residues different from the ones in the HPV16 E6 52-61 (SEQ ID NO: 16) epitope are shown in bold.

Most of the CD8 T cell epitopes described herein were shown to be naturally processed (Table 8). However, the T cell epitope clones (#1-5 and #17-5) isolated from subject 6 only recognized the E6 141-155 (SEQ ID NO: 185) 15-mer peptide pulsed target and not the E6-vac infected ones. Since none of the 9-mers and the 11-mers within the E6 141-155 (SEQ ID NO: 185) region were recognized by the T cells, these T cell clones may be detecting a 3-dimensional structure formed by the E6 141-155 (SEQ ID NO: 185) 15-mer peptide which mimicked some other antigen. Since the T cell clones were isolated from women who were able to clear their HPV infection in the present invention, it is speculated that the epitopes identified herein might be involved in viral clearance. Therefore, the present invention contemplates comparing responses between women who were able to clear their HPV 16 infection and those whose infection persisted to elucidate the role played by these epitopes in viral clearance.

With regards to the use of the epitopes identified herein as targets for tumor immunotherapy, previous findings have been disappointing particularly in the case of E6 29-38. It was observed that HPV16 E7 11-20 specific T cell clones were able to kill variety of HPV16 tumor cell lines while E6 29-38 specific T cell clone could not (Youde et al., 2005), suggesting that there was something different about the E6 29-38 epitope that made it an unsuitable target. One possible explanation for the lack of cytotoxicity of the E6 29-38 specific T cell clone could be a weaker binding affinity of E6 29-38 to the HLA-A 2.1 molecule. The present invention demonstrated lower levels of cytotoxicity by the E6 29-38 specific T cell clones against HLA-A2.1 positive allogeneic LCL compared to autologous LCL. This was not observed for T cell clones specific for other HPV16 E6 epitopes. Further, the potential of E6 52-61 epitope restricted by the HLA-B57 molecules as a tumor antigen has also been examined. Two of the three HPV16-positive tumor cell lines derived from HLA-B57 positive cervical cancer patients were killed by the E6 52-61 specific T cell clone.

Hence, the present invention further contemplates investigating the potential of other HPV epitopes as tumor antigen and using them as sources of antigens for dendritic cell immunotherapies or as a therapeutic vaccine to treat cervical cancer patients who express the particular HLA types. The small size of these epitopes makes it easier to produce a large quantity of the antigen at GMP grade compared to a whole protein. Additionally, it is safer to use these epitopes in the treatment since such a small portion of the protein will not have oncogenic potentials. It is further contemplated to identify large number of similar epitopes restricted by a wide variety of HLA types to be used either singly or in concert to develop a preventative vaccine, which could be used for general population. Such a vaccine might comprise use of recombinant viral vector, a plasmid or a peptide.

This investigation will require identification of CD8 T cell epitopes in women being treated for squamous intraepithelial lesions. Since these women in addition to being diagnosed with squamous intraepithelial lesions should also test positive for HPV16 DNA, cervical swab samples will be collected from women with abnormal pap smears for HPV DNA testing. The ones that test positive for HPV16 will have to undergo phlebotomy. The patterns of CD8 T cell epitopes contained in the HPV16 E6 and E7 proteins will be examined. The minimal and optimal amino acid sequences of these epitopes will be defined along with the restricting HLA molecules. Further, the feasibility of using these epitopes as sources of antigen for dendritic cell immunotherapy will be assessed by examining their expression on primary tumor cell lines derived from cervical cancer. The broadness of the utility of these epitopes will be examined by cross-presentation and cross-recognition of analogous CD8 T cell epitopes from HPV16 variants and other high-risk HPV types. With regards to E7 protein, it is contemplated that the efficacy of dendritic cell immunotherapy using HPV16 or HPV18 E7 whole protein and the CD8 T cell epitopes derived from E7 using the method described in the present invention will also be compared.

Figure 19:
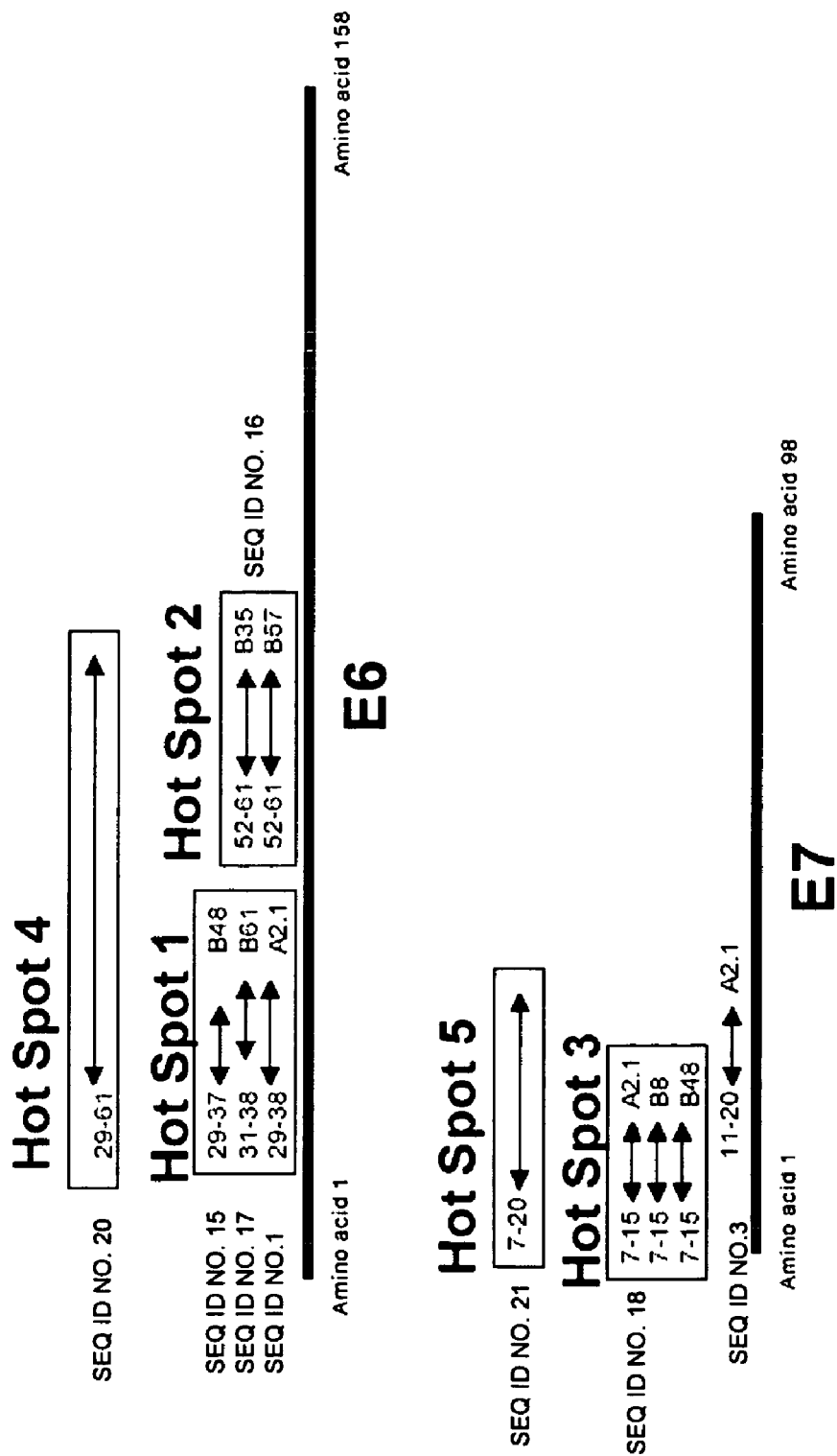
FIG. 19 is a diagrammatic representation of the "epitope hot spots" within the HPV16 E6 and E7 proteins showing the clustering of the CD8 T cell epitopes restricted by different HLA molecules.

Furthermore, the CD8 T cell epitopes described herein (E6 29-38 (SEQ ID NO: 1), E6 29-37 (SEQ ID NO: 15), E6 31-38 (SEQ ID NO: 17), E6 52-61 (SEQ ID NO: 16)) and a previously described epitope (E6 52-61 restricted by HLA-B57) (Nakagawa et al., 2004) demonstrated a striking HLA class I binding promiscuity (FIG. 19). Similar HLA class I binding promiscuity can also be demonstrated in the HPV 16 E7 protein based on the epitopes identified in previous studies (Nakagawa et al., 2004; Kast et al., 1994; Oerke et al., 2005). The regions which contain multiple T cell epitopes are identified herein as "epitope hot spots". These epitope hot spots include but are not limited to hot spot 1 (E6 29-37 (SEQ ID NO: 15) restricted by HLA-B48, E6 31-38 (SEQ ID NO: 17) restricted by HLA-B61, E6 29-38 (SEQ ID NO: 1) restricted by HLA-A2.1), hot spot 2 (E6 52-62 (SEQ ID NO: 103) restricted by HLA-835 and HLA-B57), hot spot 3 (E7 7-15 (SEQ ID NO: 18) restricted by HLA-A2.1, HLA-B8 and HLA-B48), hot spot 4 (E6 29-61 (SEQ ID NO: 20) restricted by HLA-A2.1, HLA-B35, HLA-B48, HLA-B57, and HLA-B61) and hot spot 5 (E7 7-20 (SEQ ID NO: 21) restricted by HLA-A2.1, HLA-B8, HLA-B48). The HLA-B35 and -B61 molecules are known to be present in 10.33% and 2.94% of Caucasian, 5.53% and 0.25% of African American and 5.03% and 4.62% of Oriental population, respectively. Hence, when sufficient numbers of these epitopes restricted by a wide variety of HLA types are identified, it is contemplated to use them in concert as a preventive vaccine for general population.

Although the "epitope hot spots' described herein can also be used in an analogous manner, they have an advantage of being able to be used in larger number of patients since they can cover 28.1%, 13.2% and 32.6% (allele or population frequencies) and 53.1%, 27.9% and 73.2% (phenotype frequencies) of Caucasian population for hot spots 1, 2 and 3, respectively. Thus, the epitope hot spots have significant implications for the development of vaccine and immunotherapies since the same region of the viral protein may be used for people with different HLA types.

The present invention is directed to a method of determining a pattern of immunodominant T cell epitopes within a protein expressed in an individual, comprising: stimulating the T cell line of an individual in vitro with autologous dendritic cells infected with recombinant virus expressing the protein; incubating the stimulated T cell line with first set of peptides; determining magnitude of T cell response in the incubated cells; and identifying peptides that induce strong T cell response, wherein a sequence of the peptide corresponds to a region within the protein, thereby determining the pattern of the immunodominant T cell epitopes within the protein in the individual.

Generally, the first set peptides are overlapping peptides that are 15-residue long and overlap by 10 central amino acids. These peptides cover the entire protein. Specifically, these peptides cover fragments of HPV protein having amino acid sequence of SEQ ID NO: 35 (E6 1-25), SEQ ID NO: 36 (E6 16-40), SEQ ID NO: 37 (E6 31-55), SEQ ID NO: 38 (E6 46-70), SEQ ID NO: 39 (E6 61-85), SEQ ID NO: 40 (E6 76-100), SEQ ID NO: 41 (E6 91-115), SEQ ID NO: 42 (E6 106-130), SEQ ID NO: 43 (E6 121-145), SEQ ID NO: 44 (E6 136-158), SEQ ID NO: 59 (E7 1-25), SEQ ID NO: 60 (E7 16-40), SEQ ID NO: 61 (E7 31-55), SEQ ID NO: 62 (E7 46-70), SEQ ID NO: 63 (E7 61-85) or SEQ ID NO: 64 (E7 76-98) of HPV type 16.

This method further comprises: determining amino acid sequence of the immunodominant epitope identified in the earlier method. The method of determining amino acid sequence comprises: stimulating the T cell line with autologous dendritic cells infected with a recombinant virus expressing the protein, where the T cell line was stimulated for additional rounds in vitro prior to the incubation; incubating the stimulated cell line with a second set of peptides; selecting peptide-specific T cell clones; incubating the peptide-specific T cell clones with a third set of peptides; comparing the magnitude of T cell response in the incubated T cell clones; and identifying the T cell clones demonstrating a strong T cell response, thereby determining amino acid sequence of the immunodominant epitope. Additionally, this method further comprises: identifying HLA restriction molecule of the immunodominant epitope of the T cell, which is identified by ELISPOT assay and chromium release assay. Furthermore, the method described herein can be used to identify immunodominant epitopes of CD4 T cell or CD8 T cell.

Generally, the second set of peptides used in this method are overlapping peptides that are 15-residue long and cover region of the protein identified as comprising the immunodominant T cell epitope. Specifically, the second set of peptides that comprise the immunodominant CD8 T cell epitope in HPV protein have amino acid sequence of SEQ ID NO: 45 (E6 16-30), SEQ ID NO: 46 (E6 21-35), SEQ ID NO: 47 (E6 26-40), SEQ ID NO: 90 (E6 51-65), SEQ ID NO: 91 (E6 46-54), SEQ ID NO: 92 (E6 47-55), SEQ ID NO: 93 (E6 48-56), SEQ ID NO: 94 (E6 49-57), SEQ ID NO: 95 (E6 50-58), SEQ ID NO: 96 (E6 51-59), SEQ ID NO: 97 (E6 52-60), SEQ ID NO: 98 (E6 53-61), SEQ ID NO: 99 (E6

54-62), SEQ ID NO: 100 (E6 55-63), SEQ ID NO: 101 (E6 56-64) SEQ ID NO: 102 (E6 54-62), SEQ ID NO: 18 (E7 7-15), SEQ ID NO: 3 (E7 11-20), SEQ ID NO: 5 (E7 82-90), SEQ ID NO: 6 (E7 86-93), SEQ ID NO: 57 (E7 11-19, SEQ ID NO: 58 (E7 82-90), SEQ ID NO: 65 (E7 1-15), SEQ ID NO: 66 (E7 8-20), SEQ ID NO: 67 (E7 11-25), SEQ ID NO: 68 (E7 16-30), SEQ ID NO: 69 (E7 21-35), SEQ ID NO: 70 (E7 26-40), SEQ ID NO: 71 (E7 31-45), SEQ ID NO: 72 (E7 36-50), SEQ ID NO: 73 (E7 41-55), SEQ ID NO: 74 (E7 46-60), SEQ ID NO: 75 (E7 51-65), SEQ ID NO: 76 (E7 56-70) or SEQ ID NO: 77 (E7 61-75) of HPV type 16.

These peptides are used to select CD8 T cell clones based on the secretion of IFN-γ using IFN-γ secretion assay enrichment kit. Additionally the third set of peptides are overlapping peptides that are about 8-residue long to about 15-residue long and cover amino acid sequence of the peptide of the second set that induced strong T cell response. Specifically, this peptide for determining CD8 T cell epitope in HPV protein has sequence of SEQ ID NO: 1 (E6 29-38), SEQ ID NO: 16 (E6 52-61), SEQ ID NO: 17 (E6 31-38), SEQ ID NO: 45 (E6 16-30), SEQ ID NO: 46 (E6 21-35), SEQ ID NO: 47 (E6 26-40), SEQ ID NO: 48 (E6 26-34), SEQ ID NO: 49 (E6 27-35), SEQ ID NO: NO: 50 (E6 28-36), SEQ ID NO: NO: 15 (E6 29-37), SEQ ID NO: NQ 51 (E6 30-38), SEQ ID NO: 52 (E6 31-39), SEQ ID NO: 53 (E6 32-40), SEQ ID NO: 90 (E6 51-65), SEQ ID NO: 103 (E6 52-62), SEQ ID NO: 104 (E6 51-61), SEQ ID NO: 105 (E6 53-62), SEQ ID NO: 98 (E6 53-61), SEQ ID NO: 106 (E6 53-60), SEQ ID NO: 107 (E6 54-61), SEQ ID NO: 18 (E7 7-15), SEQ ID NO: (E7 11-20), SEQ ID NO: 5 (E7 82-90), SEQ ID NO: 6 (E7 86-93), SEQ ID NO: 21 (E7 7-20), SEQ ID NO: 57 (E7 11-19), SEQ ID NO: 58 (E7 12-20), SEQ ID NO: 80 (E7 76-90), SEQ ID NO: 83 (E7 76-84), SEQ ID NO: 84 (E7 77-85), SEQ ID NO: 85 (E7 78-86), SEQ ID NO: 19 (E7 79-87), SEQ ID NO: 86 (E7 80-88) or SEQ ID NO: 87 (E7 81-89) of HPV type 16.

The immunodominant T cell epitope identified by this method is about 8-residue long to about 15-residue long. Specifically, the CD8 T cell epitope in the HPV protein may be in the N-terminal of the HPV protein and the epitope has the sequence of SEQ ID NO: 1 (E6 29-38), SEQ ID NO: 16 (E6 52-61), SEQ ID NO: 17 (E6 31-38), SEQ ID NO: 20 (E6 29-61), SEQ ID NO: 45 (E6 16-30), SEQ ID NO: 46 (E6 21-35), SEQ ID NO: 47 (E6 26-40), SEQ ID NO: N48 (E6 26-34), SEQ ID NO: 49 (E6 27-35), SEQ ID NO: 50 (E6 28-36), SEQ ID NO: 15 (E6 29-37), SEQ ID NO: 51 (E6 30-38), SEQ ID NO: 52 (E6 31-39), SEQ ID NO: 53 (E6 32-40), SEQ ID NO: 16 (E6 52-61), SEQ ID NO: 19 (E7 79-87), SEQ ID NO: 21 (E7 7-20), SEQ ID NO: 90 (E6 51-65), SEQ ID NO: 103 (E6 52-62), SEQ ID NO: 104 (E6 51-61), SEQ ID NO: 105 (E6 53-62), SEQ ID NO: 98 (E6 53-61), SEQ ID NO: 106 (E6 53-60), SEQ ID NO: 107 (E6 54-61), SEQ ID-NO: 18 (E7 7-15), SEQ ID NO: 3 (E7 11-20), SEQ ID NO: 5 (E7 82-90), SEQ ID NO: 6 (E7 86-93), SEQ ID NO: 57 (E7 11-19), SEQ ID NO: 58 (E7 12-20), SEQ ID NO: 80 (E7 76-90), SEQ ID NO: 83 (E7 76-84), SEQ ID NO: 84 (E7 77-85), SEQ ID NO: 85 (E7 78-86), SEQ ID NO: 86 (E7 80-88) or SEQ ID NO: 87 (E7 81-89) of HPV type 16. Further, these epitopes may be presented by any of the six HLA class I molecules expressed by an individual.

Generally, such methods can be performed on an individual is diagnosed with a pathophysiological condition, is in remission or is diagnosed with a precursor of the pathophysiological condition. Examples of such pathophysiological conditions include but are not limited to a neoplastic disease or disorder, an autoimmune disease or disorder or a pathogen-related disease. Further, examples of the neoplastic disease include but are not limited to prostate cancer, ovarian cancer or cervical cancer. In the case of cervical cancer, the individual might have been previously infected with HPV, had abnormal pap smear results, had been diagnosed with precursor of cervical cancer for example, SIL. Although the present invention used the method to identify immunodominant epitopes of HPV protein, this method can be used to identify dominant epitope of any protein such as prostate specific antigen (PSA) or cancer antigen-125 as long as the protein can be cloned into a recombinant virus that can infect dendritic cells. Therefore, this method can be used to identify epitopes from many other pathogens and autoantigens. Additionally, it can also be used to identify immunodominant epitopes of proteins of HPVs other than HPV16 and other than E6 and E7 proteins. For instance, proteins such as E1, E2, E4, E5, L1 or L2. The T cells in these methods are stimulated with autologous dendritic cells infected with recombinant vaccinia virus expressing the entire HPV protein. This HPV protein is an E6, an E7, an E2, an E4, an E5, a L1 or a L2 protein. The HPV protein belongs to any of the following type of HPV: 16, 18, 31, 33, 35, 39, 45, 51, 52, 56, 58, 59, 68, 73 or other high-risk types. The magnitude of T cell response in these methods is determined by the ELISPOT assay.

The present invention is also directed to a synthetic peptides comprising sequence of first set peptides, second set peptides, third set peptides and immunodominant CD8 T cell epitopes having the sequences as described earlier.

The present invention is further yet directed to a method of immunotherapy towards HPV protein in an individual, comprising: isolating immune cells from the individual; pulsing the isolated immune cells with peptide comprising one or more than one immunodominant T cell epitope with the sequence identified herein; and transferring the pulsed immune cells back to the individual, where the immune cells activate HPV-specific immune responses in the individual, thereby generating immunotherapy towards HPV protein in the individual. The immune cells used in this method are T cells or dendritic cells. The individual likely to benefit from this immunotherapy will be the one who has abnormal pap smear results, who has been diagnosed with precursor of cervical cancer for example, SIL or who has been diagnosed with cervical cancer or is suspected or at risk of suffering from the disease. Since antigenic epitopes for many other pathogens and autoantigens can be identified using the method described in the present invention, the immunotherapy described above will benefit individuals suffering from other cancers, pathogen-related diseases and autoimmune diseases. Additionally, the aspect regarding the type of HPV, the type of HPV protein and sequence of the peptide is as described earlier.

Furthermore, the present invention is also directed to an immunogenic composition comprising a sequence or a combination of sequences identified herein and an adjuvant. Such a sequence or sequences may be expressed in a recombinant viral vector, a plasmid or is a peptide. Additionally, the present invention is directed to a method of preventing or treating a pathophysiological condition involving expression of HPV protein in an individual. Such a method comprises administering the immunogenic composition described herein to the individual, where the composition activates HPV-specific immune response in the individual, thereby treating the pathophysiological condition in the individual. Generally, the individual who might benefit from this method is the one who has abnormal pap smear results, has been diagnosed with a precursor of cervical cancer such as SIL or is suspected or at risk of suffering from cervical cancer. As discussed herein, since this method can be used to identify immunodominant epitopes of proteins other than HPV that are expressed in other diseases or disorders, these diseases or disorders can also be treated in the manner analogous to the treatment directed towards HPV protein.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Subjects

Several hundred female subjects ranging in age from 13 to 20 years, were participants in a longitudinal study of HPV infection initiated in 1991 (Moscicki et al., 1998). As part of this parent study, the subjects were being monitored via cervical HPV DNA testing by PCR (Ting and Manos 1990), cytology and colposcopy every 4 months. Subjects who had negative HPV16 cervical specimens for a minimum of 2 consecutive visits, after previously testing positive, were selected for the current study. Subjects had to remain HPV16 negative for the duration of the study.

EXAMPLE 2

HLA Typing

HLA typing was performed using peripheral blood mononuclear cells (PBMC) and either a serological method and/or polymerase chain reaction-sequence specific amplification (PCR-SSP). High-resolution HLA typing by sequencing was also performed whenever necessary to identify the alleles (i.e. to identify HLA-A2.1 positive subjects).

EXAMPLE 3

Peptides

Overlapping 15-mer peptides (overlapping by 10 amino acids) covering the entire HPV16 E6 protein (Seedorf, K. et al., 1985) and the overlapping 9-mer peptides (overlapping by 8 amino acids) covering the entire HPV16 E6 protein were synthesized. Two 8-mer peptides and two 10-mer peptides used to define the minimal amino acid sequence were also synthesized.

EXAMPLE 4

Generating CD8 T Cell Lines

HPV16 E6-specific T cell lines were established by in vitro stimulation of CD8 cells using autologous dendritic cells infected with recombinant vaccinia viruses expressing the E6 protein (E6-vac) (Nakagawa, M et al., 1997). CD8 cells were selected from PBMC using a commercially available magnetic kit (CD8 isolation kit, Miltenyi Biotec, Auburn, Calif.). Autologous dendritic cells were established by isolating monocytes from PBMC using CD14 antibody coupled to magnetic beads (Miltenyi Biotech), and by growing the autologous dendritic cells in the presence of GM-CSF (50 ng/ml) and rIL-4 (100 u/ml) for 7 days. They were matured by culturing in wells containing irradiated L cells expressing CD40 ligand for 48 h, and E6-vac was added during the last 24 h. Seven days later, the in vitro stimulation was repeated for an additional 7 days.

EXAMPLE 5

IFN-γ Enzyme-Linked Immunospot (ELISPOT) Assay

A method described previously was used with some modifications (Larsson, M. et al., 2002). Briefly, a 96-well plate (Millititer, Millipore, Bedford, Mass.) was coated with 5 μg/ml primary anti-γ-IFN monoclonal antibody (Mabtech, Stockholm, Sweden) and stored at 4° C. overnight. The plate was then washed 4 times with phosphate buffered saline (PBS) and blocked using RPMI 1640 plus 5% pooled human serum for 1 h at 37° C.

To examine the pattern of CD8 T cell epitopes (FIG. 1), $1 \times 10^5$ cells of a CD8 T cell line were plated in each well. Overlapping 15-mer peptides (overlapping by the 10 central amino acids) were pooled to 10 groups (each group containing 3 peptides) and tested in duplicate (10 μM for each peptide) along with no peptide control. For screening T cell clones, 50 μl of culture media containing the T cell clones was added with $1 \times 10^5$ autologous Epstein-Barr virus-transformed B lymphoblastoid cell line (EBV-LCL) cells (data not shown). With the remaining experiments using T cell clones, $1 \times 10^3$ T cell clones were plated along with $1 \times 10^5$ EBV-LCL cells to reduce the number of T cell clones necessary for analysis. All peptides were used at a concentration of 10 μM.

Figure 2A:
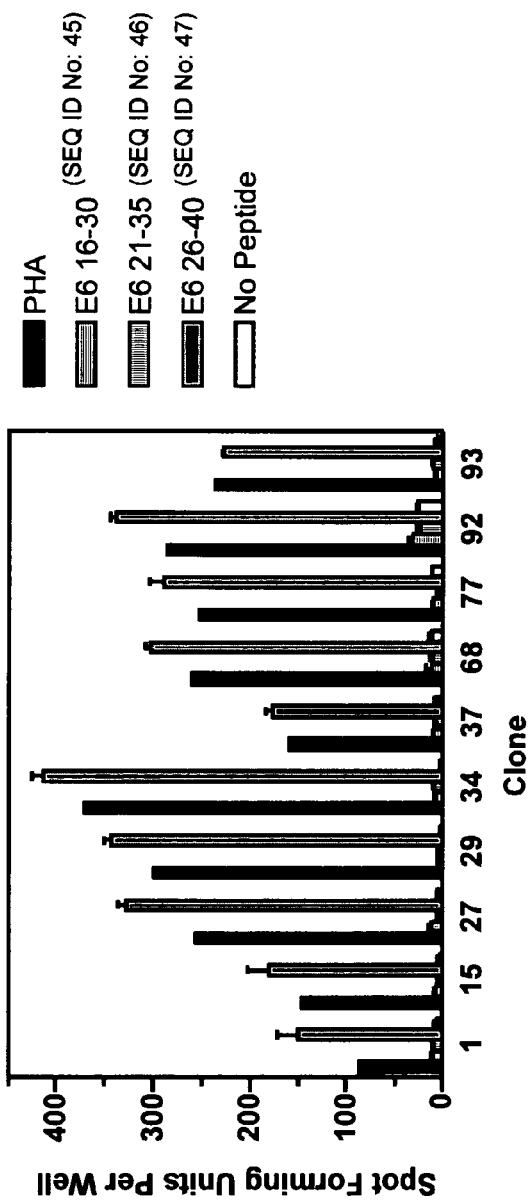
FIGS. 2A-B show results of ELISPOT assay performed to retest screen-positive T-cell clones from subject 15, with E6 16-30 (SEQ ID NO: 45), E6 21-35 (SEQ ID NO: NO: 46) and E6 26-40 (SEQ ID NO: 47) peptides. A total of 1000 T-cell clones were plated in duplicate, along with $10^5$ autologous EBV-LCL cells.
Figure 2B:
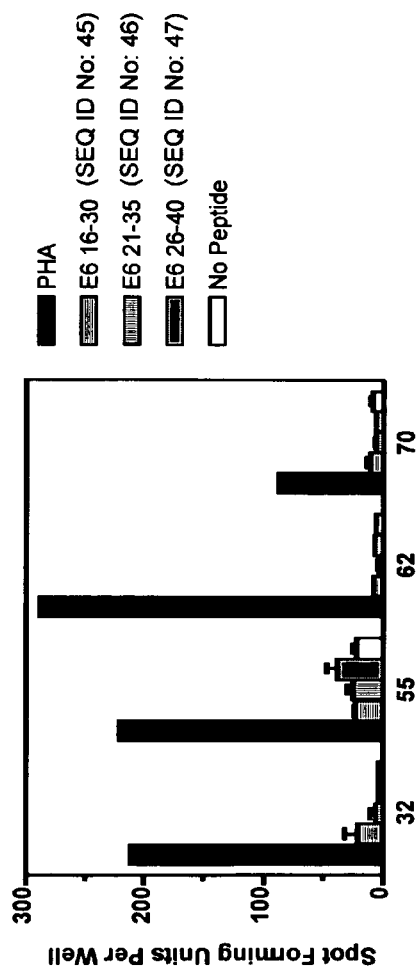

Autologous EBV-LCL cells were incubated with E6-vac, E7-vac or WR at the multiplicity of infection of 10 for 1 h at 37° C. prior to being plated (FIG. 2B). Phytohemagglutinin (PHA) at 10 μg/ml was added as positive control. After a 24 h incubation at 37° C., the plate was washed 4 times with PS plus 0.05% Tween-20. A total of 50 μl of secondary antibody (1 μg/ml biotin-conjugated anti-IFNγ monoclonal antibody; Mabtech) was added and the plate was incubated for 2 h at 37° C. The plate was then washed 4 times with PBS plus 0.1% Tween-20. Avidin-bound biotinylated horseradish peroxidase H (Vectastain Elite kit; Vector laboratories, Inc., Burligame, Calif.) was added with deionized water three times and air-dried overnight. Spot forming units were counted using an automated ELISPOT analyzer (Cell Technology, Inc., Jessup, Md.) and were normalized to number of spot forming units per $1 \times 10^6$ cells for CD8 T cell lines. Response was considered positive when the number of spot forming units in wells with peptide pools was at least double that seen in the no peptide control wells.

EXAMPLE 6

Magnetic Selection of IFN-γ Secreting Cells to Isolate T Cell Clones

To isolate T cell clones recognizing the E6 antigenic epitope from subject 15, her CD8 T cell lines were stimulated as described above for two additional 7-day cycles, so the frequency of targeted T cell clones would be above the threshold of selection ($\geq 0.1\%$). The peptide-specific T cells were positively selected using the IFN-γ secretion assay enrichment kit, according to the manufacturer's instructions (Miltenyi Biotec), after stimulating cells with 10 μM each of peptides contained in the E6 16-40 (SEQ ID NO. 36) pool. Selected cells were plated at a concentration of 0.5 cells per well in the presence of a 0.5× feeder cell mixture (Yssel's media containing 1% pooled human serum, penicillin G 100 units/ml, streptomycin 100 μg/ml, $5 \times 10^5$/ml irradiated allogenic PBMC, $5 \times 10^4$/ml irradiated JY cells, 0.1 μg/ml PHA, with/without 10 u/ml rIL-4). Control wells for growth contained 1 to 1000 cells per well. On day 5, 100 μl of Yssel's media containing 20 U/ml of rIL-2 was added to each well. Growing microcultures were transferred to 24-well plates containing 1 ml of 1× feeder cell mixture per well (Yssel's media containing 1% pooled human serum, penicillin G 100 units/ml, streptomycin 100 μg/ml, 1×10⁶/ml irradiated allogenic PBMC, 1×10⁵/ml irradiated JY cells and 0.1 μg/ml PHA).

EXAMPLE 7

Chromium Release Assay

Either the cells of the autologous EBV transformed B lymphobastoid cell line or of the allogenic EBV-transformed B lymphoblastoid cell line sharing designated HLA class I molecule(s) with subject 15 were pulsed with 10 μM of E6 29-37 (SEQ ID NO: 15) peptide antigen. The cells were radiolabeled with 2004 μCi sodium chromate ($Na_2^{51}CrO_4$) and incubated with the peptide. After washing, the cells were plated in triplicate in 96-well plates at 3×10³ cells per well. Effector cells were added at eight different effector:target cell ratios. The plated cells were pelleted by centrifugation and then incubated for 5 h at 37° C. in a humidified 5% $CO_2$ incubator. The supernatants were harvested using a Skatron harvesting press and the chromium-51 was counted using a gamma counter (Packard Instruments, Meriden, Conn.). Percent specific lysis was calculated as described previously (Nakagawa, M. at al., 1997).

EXAMPLE 8

FACS Analysis

The T cell clones were stained for surface markers with anti-CD4-anti-CD8 and anti-CD3-anti-CD16 (Caltag, Burlingame, Calif.) and analyzed (FACScan, Beckton Dickinson Immunocytometry Systems, San Jose, Calif.).

EXAMPLE 9

Pattern of CD8 T Cell Epitopes in the HPV16 E6 Protein

A total of 23 subjects enrolled in this study had a history of cleared HPV16 infection. The mean age at the time of blood sampling was 25.3 years. The mean time since the last positive HPV16 result was 51.8 months and the mean number of study visits which were HPV16 negative by PCR following the last HPV16-positive visit was 12.0. The results of the ELISPOT assays, using pooled 15-mer peptides, examining the pattern of CD8 T cell epitopes in the HPV16 E6 protein are shown in FIG. 1. At least one positive peptide was identified in 8 of 23 subjects examined. The region within E6 that most often contained antigenic epitopes with the greatest magnitude of response was that of amino acids 16 to 40, which was observed in 4 subjects (17.4%); two subjects had one positive region (subjects 1 and 15); four subjects had two positive regions (subjects 2, 5, 7 and 20) and one subject had three positive regions (subject 18). Seven of the 23 subjects (30.4%) studied showed the presence of potential antigenic epitopes in the N-terminal half (amino acids 1-85). In comparison, two of the 23 subjects (8.7%) showed the presence of potential antigenic epitopes in the C-terminal half (amino acids 76-158) (P=0.03). The results are summarized in Table 3.

TABLE 3

Patterns of CD8 T cell responses to HPV 16 E6 protein in women who had cleared the infection

| Subject E6 Reg | 1 | 2 | 5 | 7 | 15 | 18 | 20 | 23 |
|---|---|---|---|---|---|---|---|---|
| 1-25 (SEQ ID NO: 35) | | | | | | | | |
| 16-40 (SEQ ID NO: 36) | | | X | X | X | | X | |
| 31-55 (SEQ ID NO: 37) | | x | | | | x | x | X |
| 46-70 (SEQ ID NO: 38) | X | X | | x | | | | |
| 61-85 (SEQ ID NO: 39) | | | | | | x | | x |
| 76-100 (SEQ ID NO: 40) | | | | | | | | |
| 91-115 (SEQ ID NO: 41) | | | | | | X | | |
| 106-130 (SEQ ID NO: 42) | | | | | | | | |
| 121-145 (SEQ ID NO: 43) | | | | | | | | |
| 136-158 (SEQ ID NO: 44) | | | x | | | | | |

*The strongest T cell response for a given subject is indicated with upper case X and subdominant response is indicated with lower case x. For subjects 1 and 15, the epitopes were characterized and amino acid sequences identified.

EXAMPLE 10

Amino Acid Sequence and Restriction Molecule of a CD8 T Cell Epitope

Since the amino acid region 16 to 40 most often showed the presence of potential CD8 T cell epitopes with the largest number of spot forming units (FIG. 1), an epitope in this region from one of these subjects was characterized. Two million cells from the CD8 T cell line of subject 15 were incubated with the three peptides contained in the E6 16-40 (SEQ ID NO. 36) pool (E6 16-30 [PRKLPQLCTELQTTI] (SEQ ID NO: 45), E6 21-35 [QLCTELQTTIHDIIL] (SEQ ID NO:46), and E6 26-40 [LQTTIHDIILECVYC] (SEQ ID NO: 47) for 8 h and 9.7×10³ peptide-specific T cells were isolated. T cell clones were established by limiting dilution, as described earlier.

Figure 3:
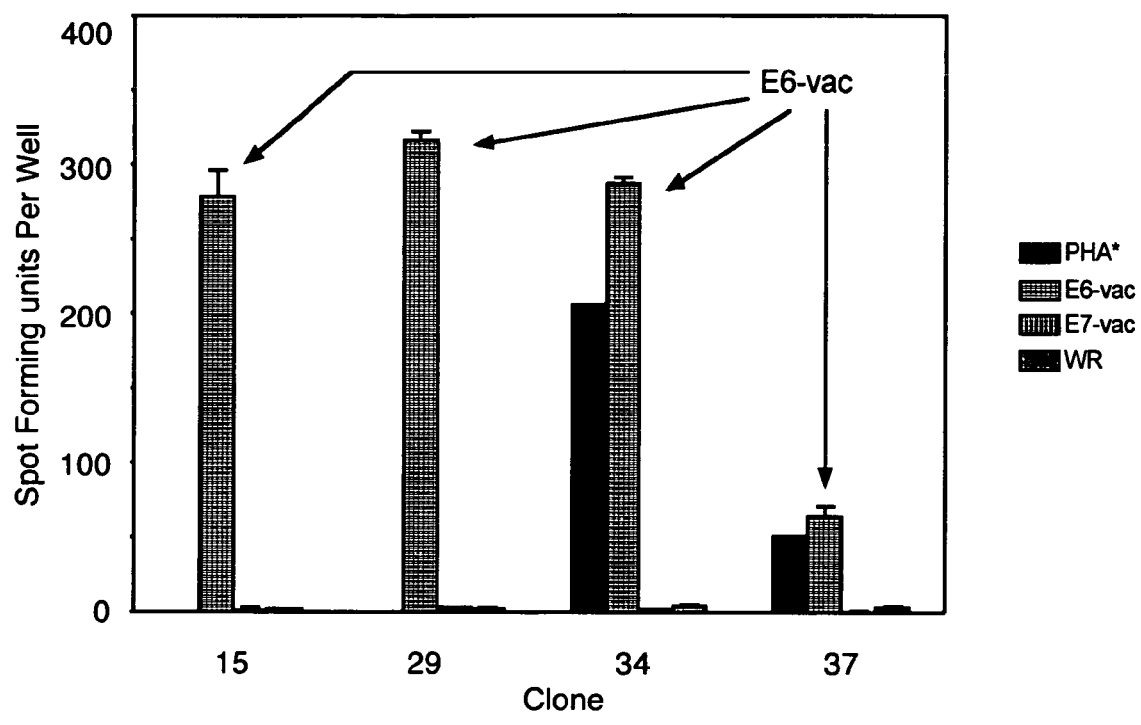
FIG. 3 shows ELISPOT assay performed using E6-vac-, E7-vac- and WR-infected autologous EBV-LCL as antigen presenting cells revealed that the T cell clones from subject 15 recognized a naturally processed E6 epitope. A total of 1000 T cell clone cells were plated in duplicate along with $10^5$ autologous EBV-LCL cells infected with E6-vac, E7-vac and WR, respectively, at a multiplicity of infection of 10.

A random selection of 94 out of 400 clones that expanded were screened with E6 16-30 (SEQ ID NO: 45), E6 21-35 (SEQ ID NO: 46) and E6 26-40 (SEQ ID NO: 47), along with no peptide control. Thirteen T cell clones were positive for E6 26-40 (SEQ ID NO: 47), three clones were positive for E6 21-35 (SEQ ID NO: 46), two clones were dually positive for E6 21-35 (SEQ ID NO: 46) and E6 26-40 (SEQ ID NO: 47) and one clone was positive for E6 16-30 (SEQ ID NO: 45). One thousand of each positive T cell clone, which had >100 spot-forming units with peptide compared to the control were retested in duplicate. Ten of the 15 clones (13 clones singly positive for E6 26-40 (SEQ ID NO: 47) and two clones dually positive for E6 21-35 (SEQ ID NO: 46) and E6 26-40 (SEQ ID NO: 47) initially positive for E6 26-40 (SEQ ID NO: NO, 47) were re-tested and their specificity to E6 24-60 (SEQ ID NO: 47) was confirmed (FIG. 2A). Three clones initially positive for E6 16-30 (SEQ ID NO: 45) and one clone initially positive for E6 21-35 (SEQ ID NO: 46) were negative (FIG. 2B), Clones 15, 29, 34 and 37 also showed IFN-γ secretion to E6-vac but not to E7-vac and WR, confirming their specificity to E6 (FIG. 3). These results suggested that the T cell epitope being studied was naturally processed. Six additional clones positive for E6 26-40 (SEQ ID NO: 471 were also positive for E6-vac but E7-vac and WR were not tested.

Figure 4:
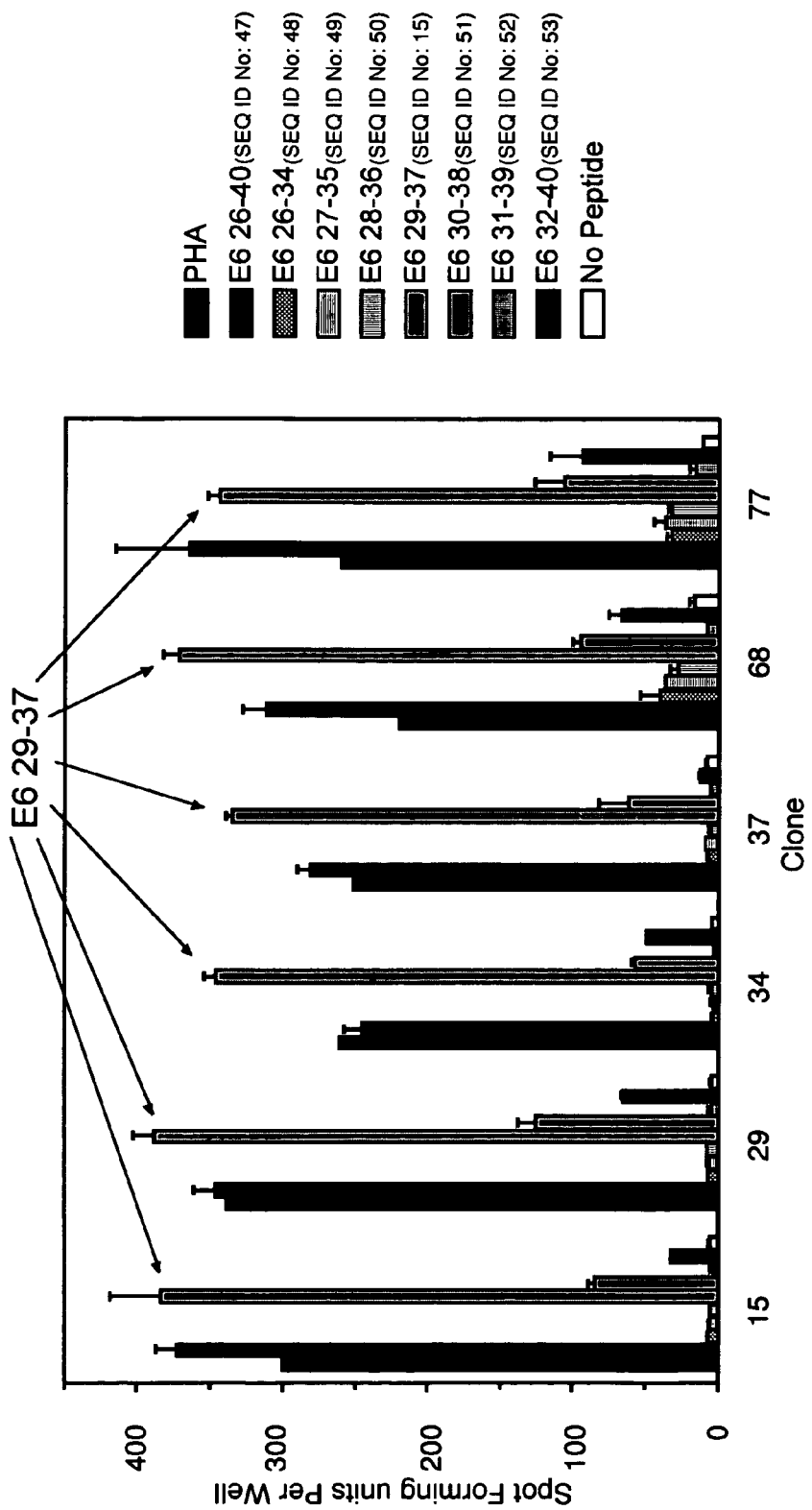
FIG. 4 shows ELISPOT assay using overlapping 9-mer peptides within the E6 26-40 (SEQ ID NO: 47) region, demonstrating the strongest response with the E6 29-37 (SEQ ID NO: 15) peptide for six T cell clones from subject 15. One thousand T cell clone cells were plated in duplicate along with $10^5$ autologous EBV-LCL cells.

Six clones with confirmed specificity to E6 26-40 (SEQ ID NO: 47) that were growing well were tested using seven 9-mer peptides (overlapping by 8 amino acids) within the 15 amino acid region and the results are shown in FIG. 4. AU six clones demonstrated the greatest number of spot-forming units with the E6 29-37 9-mer peptide (TIHDIILEC, SEQ ID NO: 15). To define the shortest and the optimal sequence of this epitope, two 8-mer peptides within E6 29-37 (SEQ ID NO: 15) and two 10-mer peptides surrounding E6 29-37 (SEQ ID NO: 15) were tested. Four clones positive for E6

26-40 (SEQ ID NO: 47) were tested and the results are shown in FIG. 5A. It was observed that the response to E6 29-37 (SEQ ID NO: 15) 9-mer was stronger in all clones tested compared to either 8-mer. However, the difference between E6 30-37 8-mer (IHDIILEC; SEQ ID NO: 55) and E6 29-37 (SEQ ID NO: 15) 9-mer was >100 spot-forming units only for clone 37. The responses to E6 26-40 (SEQ ID NO: 47) 15-mer, E6 29-38 10-mer (TIHDIILECV; SEQ ID NO: 1), E6 28-37 10-mer (TTIHDIILEC; SEQ ID NO: 54) and E6 29-37 (SEQ ID NO: 15) 9-mer were similar. To clarify whether the E6 30-37 (SEQ ID NO; 55) 8-mer or the E6 29-37 (SEQ ID NO: 15) 9-mer was the optimal peptide, these peptides along with the E6 29-36 (SEQ ID NO: 56) 8-mer peptide were serially diluted and retested. The E6 29-37 (SEQ ID NO: 15) 9-mer was positive over a wider range of dilutions compared to either one of the 8-mers for the four clones that were tested (clones 15, 29, 34 and 37). A representative graph for clone 15 is shown in FIG. 5B. These results suggested that the shortest and optimal peptide was E6 29-37 (SEQ ID NO: 15).

Figure 6A:
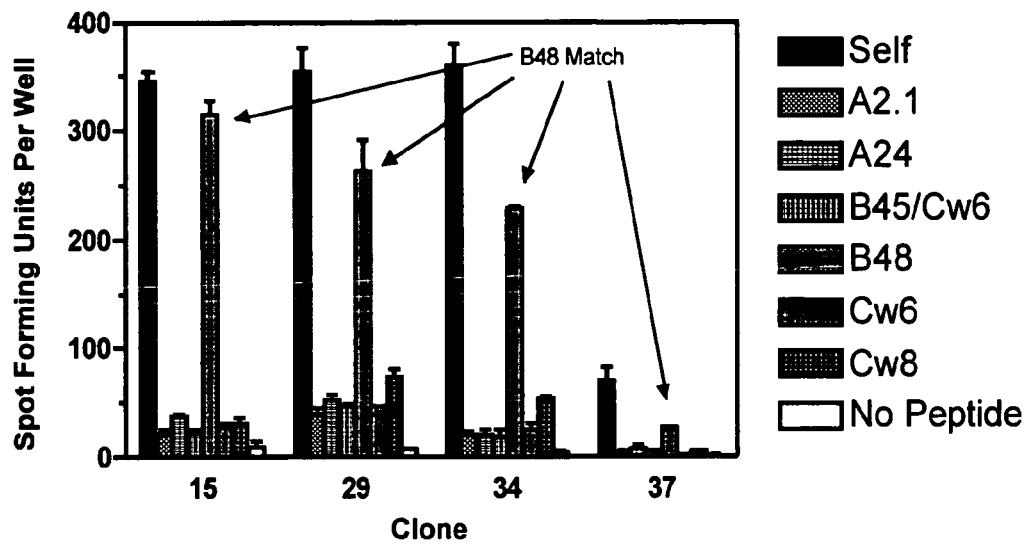
FIGS. 6A-B identify the restricting HLA class 1 molecule for the CD8 T cell epitope of subject 15.
Figure 6B:
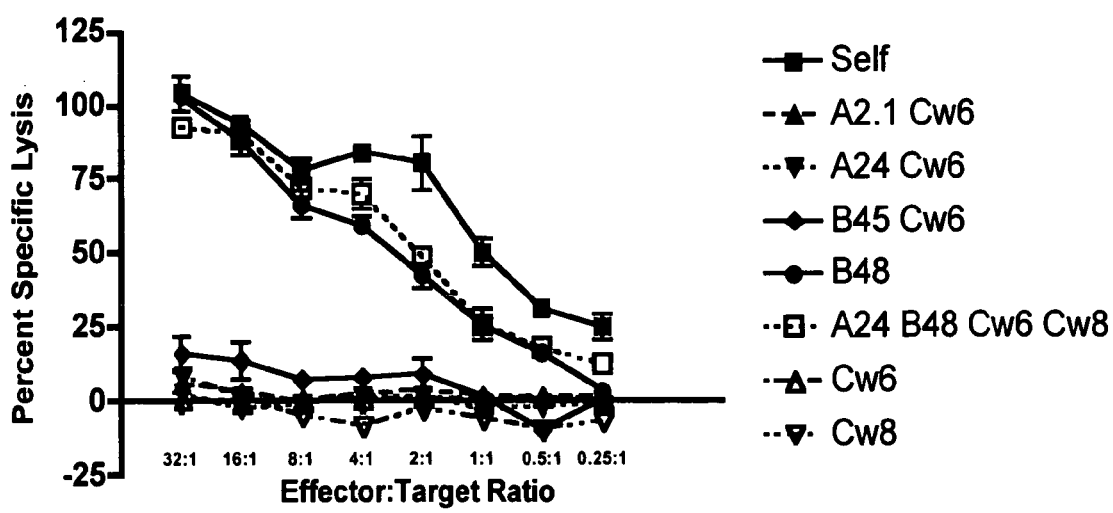

Allogeneic EBV-LCL cells sharing one or two HLA class I molecules with subject 15 (A2.1, A24, B45, B48, Cw6, Cw8) were used to determine the restriction element for the E6 29-37 (SEQ ID NO: 15) peptide. Using ELISPOT, the restriction element appeared to be the HLA-B48 molecule for the four clones that were tested (clones 15, 29, 34 and 37) (FIG. 6A). Since the T cell clones present peptide antigens to themselves, the analysis was repeated using a chromium release assay for clones 34 and 37. A representative graph for clone 34 is shown in FIG. 6B. Two allogeneic EBV-LCLs expressing the HLA-B48 molecule were tested and both demonstrated positive results. The negative control peptide (E7 7-15; SEQ ID NO: 18) presented by autologous or B48-matched EBV-LCL demonstrated no response, underscoring the specificity of the T cell clones (clones 34 and 37). The E6 29-37 (SEQ ID NO: 15) peptide did not contain any known anchoring residues for the HLA-B46 molecule. The surface phenotypes of clones 15, 29, 34 and 37 were CD3+CD4−CD8+CD16−.

EXAMPLE 11

CD8 T Cell Epitopes Described on the Basis of Strong T Cell Responses Presented by Uncommon HLA Types The characteristics of the HPV16 E6 and E7 epitopes identified based on the magnitude of the T cell responses is summarized in Table 4.

These peptides were 9 or 10 amino acids in length and were restricted by HLA-B molecules. Since the restriction elements were not common, it would mean that few people would benefit from therapies utilizing these epitopes. However, there might be a biological reason for their low population frequency. For example, if a dominant epitope was restricted by a common HLA molecule, the probability of evolving virus resulting in a mutation in that epitope might be greater than if the epitope were restricted by a rare HLA molecule. If this was the case, then trying to identify antigenic epitopes used by a large proportion of population might be futile. Instead, a large numbers of antigenic epitopes should be identified to tailor to individuals' HLA types. Hence, whether the epitopes exhibiting a strong T cell response were more likely to be restricted by uncommon HLA molecules will be investigated.

EXAMPLE 12

Comparison Between Different Methods of Identifying New Antiigenic Epitopes of Human Papillomavirus Type 16 E6 and E7 Proteins Three different methods were compared to identify the most effective method of identifying new epitopes for which the numbers of specific T lymphocytes in the circulation were expected to be small in addition to being widely applicable for identifying new T cell epitopes.

The first method identified antigenic peptides among those peptides that were shown to bind HLA A2.1 molecules. To examine the immunogenicity of HPV16 E6 and E7 peptides, cytotoxic T lymphocyte lines were derived from PBMC of women who were participants in a cohort study investigating the natural history of HPV infection. Seven of these women (subjects 1 to 7) were selected for being HLA-A2 positive and having had a history of cleared HPV16 infection. The mean age at infection was 24 years. The mean duration since the last HPV16—positive result was 25.0 months, which meant that on average, the subjects had five consecutive visits with negative PCR results.

Figure 7:
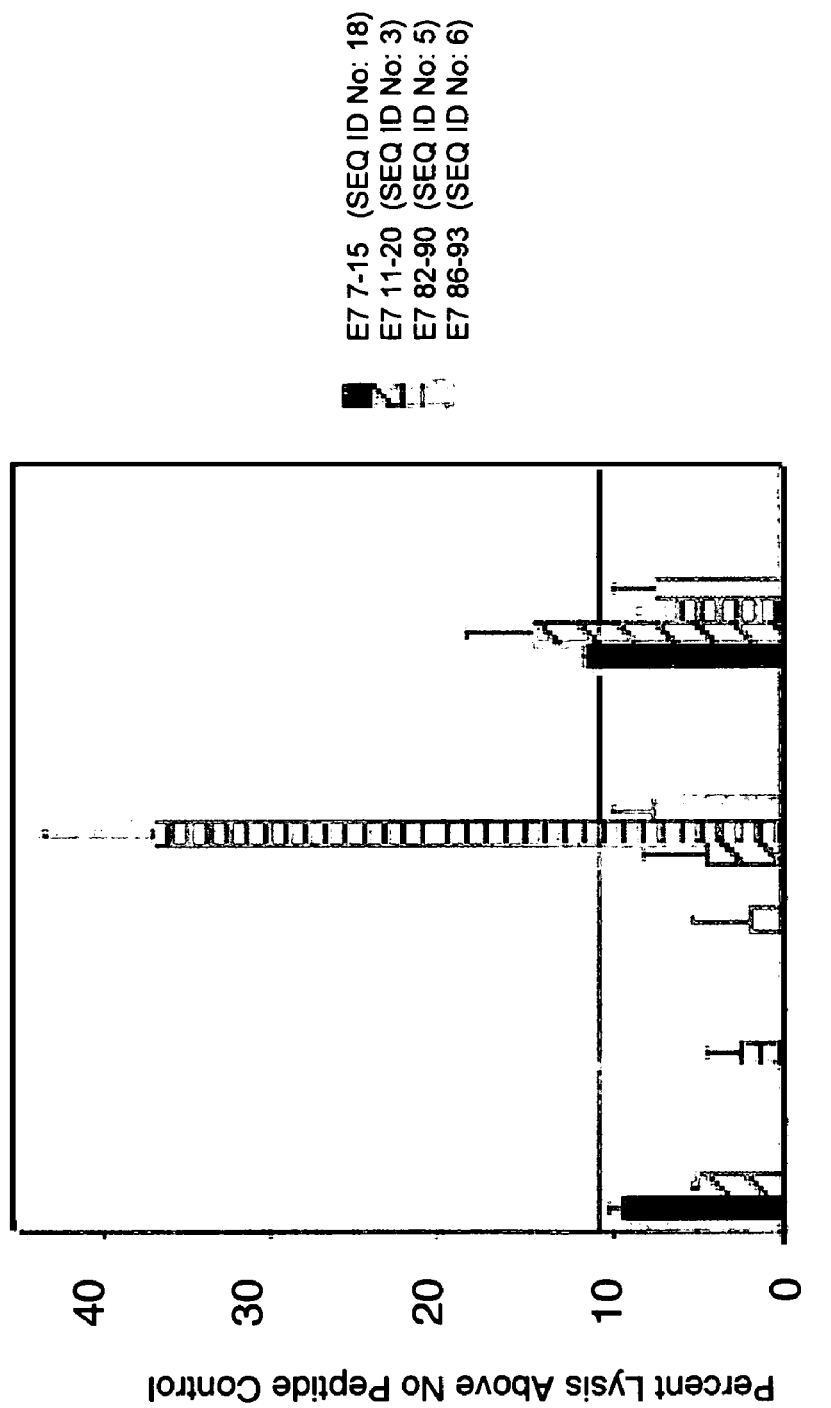
FIG. 7 shows the results of the chromium release assay of T cell lines established from HLA-A2. 1-positive women with past HPV16 infection who have not developed SIL. A positive response to E7 7-15 (SEQ ID NO: 18), E7 11-20 (SEQ ID NO: 3) or E7 82-90 (SEQ ID NO: 5) was demonstrated once each (above the cutoff line).

The cytotoxic T lymphocyte lines were established by stimulating PBMC with autologous dendritic cells that were infected with E6-vac and E7-vac. Chromium release assays were performed to assess the lysis of peptide (E7 7-15 (SEQ ID NO: 18), E7 11-20 (SEQ ID NO: 3), E7 82-90 (SEQ ID NO: 5) or E7 86-93[TLGIVCPI; SEQ ID NO: 6]-pulsed target cells) (only E7 peptides were studied because of low cell yield). These peptides were previously shown to bind the HLA-A2.1 molecule (Kast et al., 1994). Of the seven subjects, two demonstrated positive responses to one (E7 82-90 (SEQ ID NO: 5) in subject 4) or two (E7 7-15 (SEQ ID NO: 18) and E7 11-20 (SEQ ID NO: 3) in subject 6) peptides (FIG. 7). Although the antigenicity of E7 11-20 (SEQ ID NO: 3) and E7 82-90 (SEQ ID NO: 5) were described (Alexander at al.,

TABLE 4

Summary of HPV16 E6 and E7 CD8 T cell epitopes identified based on strong T cell response

| Epitope | Subject | Sequence | Restriction Element | Population Frequency | | |
|---|---|---|---|---|---|---|
| | | | | Caucasian | Black | Oriental |
| E6 29-37 (SEQ ID NO: 15) | 15 | TIHDIILEC | B48 | 0.20 | 0.31 | 3.82 |
| E6 52-61 (SEQ ID NO: 16) | 1 | FAFRDLCIVY | B57 | 2.91 | 3.96 | 1.33 |
| E7 79-87 (SEQ ID NO: 19) | 1 | LEDLLMGTL | B60 | 3.12 | 0.46 | 9.13 |

1996; Evans et al., 1997; Ressing et al., 1995; Youde et al, 2000), the antigenicity of E7 7-15 (SEQ ID NO: 18) peptide was not known.

To fully characterize these epitopes, T cell clones were isolated. In order to do so, T cell lines were first established from five subjects by serially stimulating CD8 T lymphocytes with autologous dendritic cells pulsed with E7 7-15 (SEQ ID NO: 18), E7 11-20 (SEQ ID NO: 3), or E7 82-90 (SEQ ID NO: 5) peptides. IFN-γ ELISPOT assays were performed to determine the frequency of T lymphocytes specific to these peptides. Only subject 6 demonstrated the presence of E7 7-15 (SEQ ID NO: 18) specific T lymphocytes. This T cell line was also positive for E7 11-20 (SEQ ID NO: 3). Further, the cell line was stimulated for two additional cycles and the frequencies of E7 7-15 (SEQ ID NO: 18) and E7 11-20 (SEQ ID NO: 3)-specific T lymphocytes determined by ELISPOT assay. The frequencies of E7 7-15 (SEQ ID NO: 18) and E7 11-20(SEQ ID v 3)-specific T lymphocytes were observed to be 0.20 and 0.47% respectively.

Figure 8A:
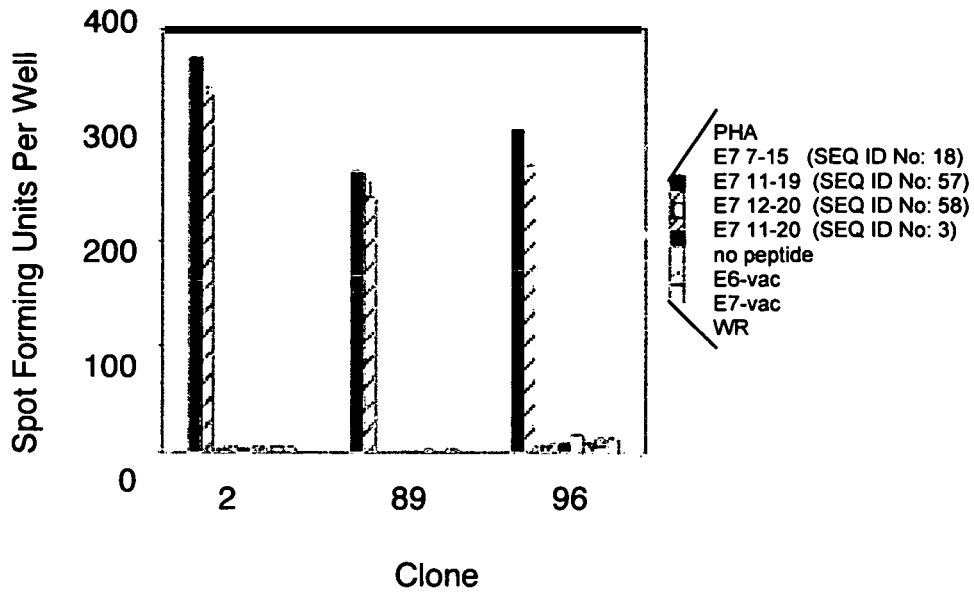
FIGS. 8A-B show confirmation of the E7 7-15 (SEQ ID NO: 18) specificity of the screen-positive T cell clones and identification of their restriction element.
Figure 8B:
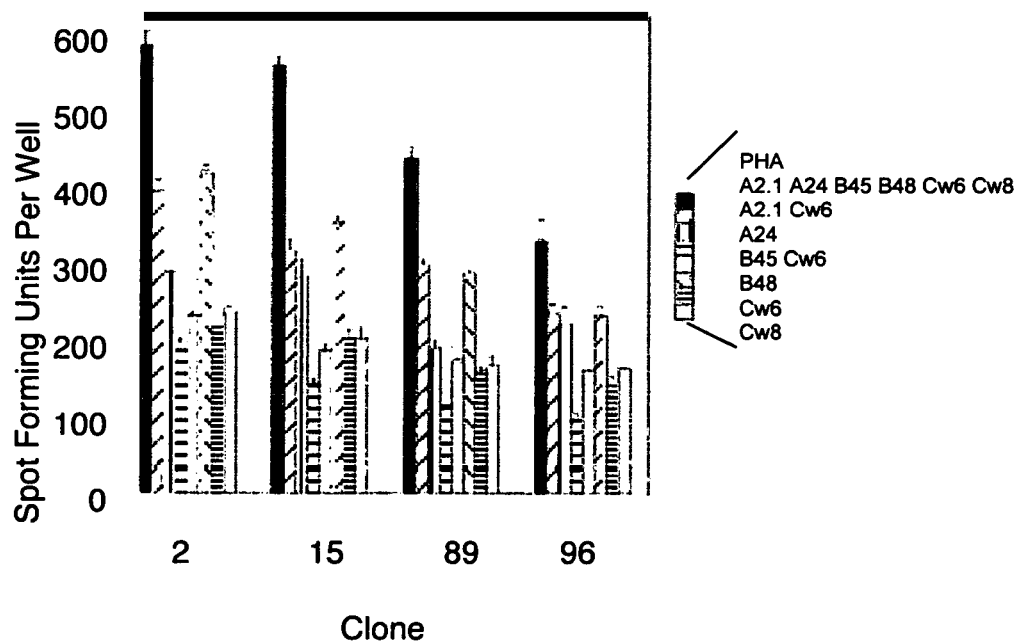
Figure 9A:
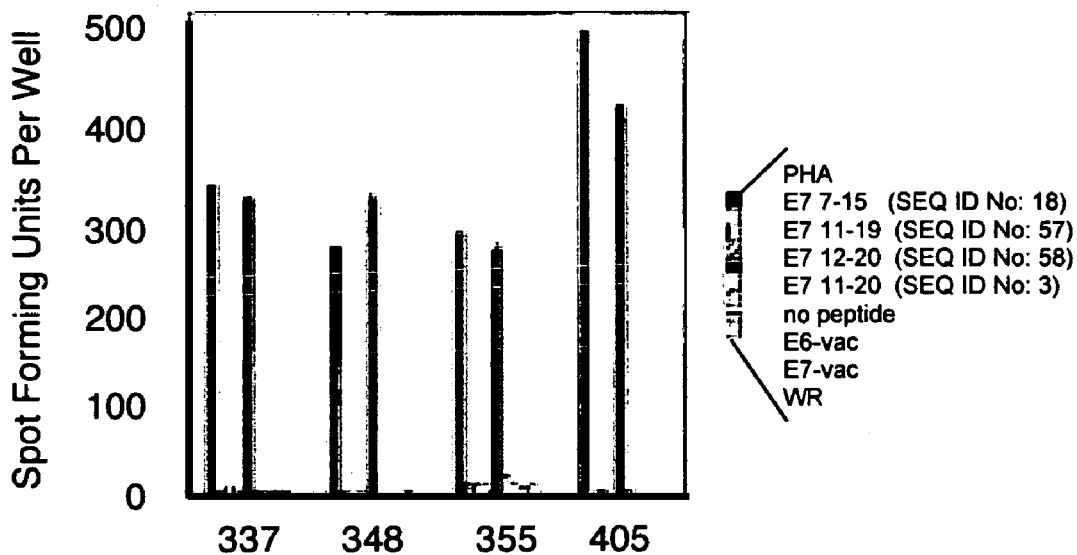
FIGS. 9A-B show confirmation of the E7 11-20 (SEQ ID NO: 3) specificity of the screen positive T cell clones and identification of their restriction element.
Figure 9B:
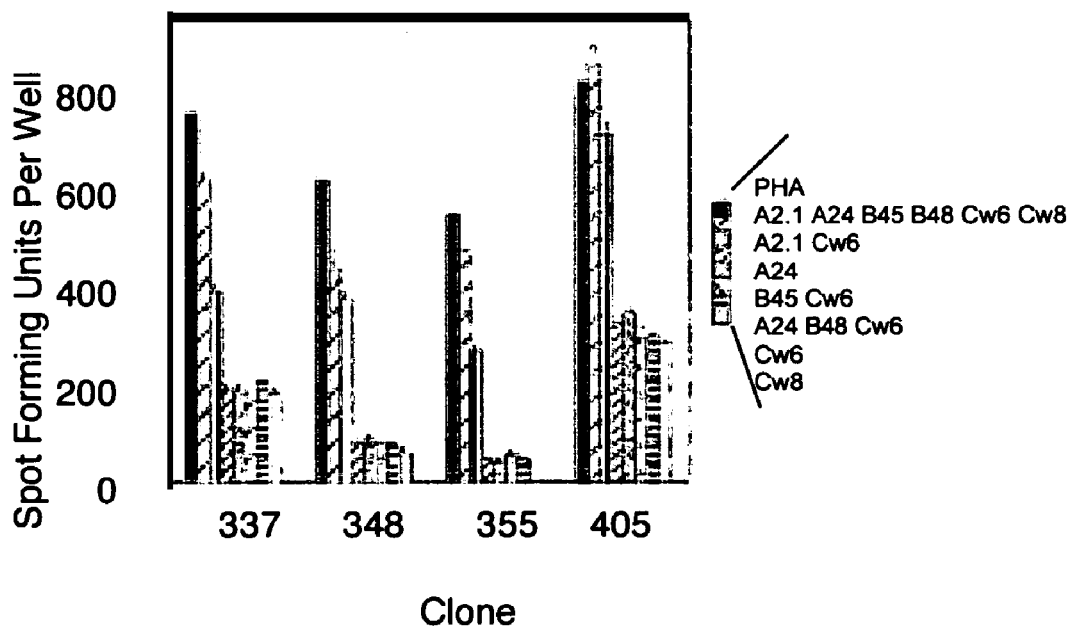

Next, approximately $1.5 \times 10^3$ E7 7-15 (SEQ ID NO: 18)-specific and $2.5 \times 10^4$ E7 11-20 (SEQ ID NO: 3)-specific T cell were isolated on the basis of IFN-γ secretion from the T cell line of subject 6. The limiting dilution was performed separately for each peptide by plating cells at a frequency of 0.5 cells per well. A total of 288 clones for E7 7-15 (SEQ ID NO: 18) and 157 clones for E7 11-20 (SEQ ID NO: 3) were expanded. Then, 96 of these of these were randomly selected and screened for specificity to the E7 7-15 (SEQ ID NO: 18) peptide on the basis of IFN-γ secretion using ELISPOT (data not shown). Of these, 81 (84.3%) were positive for E7 7-15 (SEQ ID NO: 18) peptide and 2 (2.1%) were positive for EBV antigens). Similarly, out of 94 randomly selected clones that were screened for E7 11-20 (SEQ ID NO. 3), 89 (94.7%) were positive for E7 11-20 (SEQ ID NO: 3) and 2 (2.1%) clones were positive for EBV antigens. The results of restriction mapping demonstrated that E7 7-15 (SEQ ID NO: 18) was restricted by HLA-B48 molecule, which was unexpected (FIG. 8B) and E7 11-20 (SEQ ID NO: 3) was restricted by HLA-A2.1 as expected (FIG. 9B). The fact that E7 7-15 (SEQ ID NO: 18) peptide was likely to be restricted by the HLA-B48 molecule demonstrated a limitation of the approach in which peptide binding to only common HLA types was studied. The T cell clones specific for the E7 7-15 (SEQ ID NO: 18) and E7 11-20 (SEQ ID NO: 3) epitopes did not recognize E7-vac-infected autologous EBV-LCL (FIGS. 8A and 9A). Additionally, fluorescence-activated cell sorter analysis demonstrated that all T cell clones that were examined had the surface phenotype CD3$^+$CD4$^-$CD8$^+$CD16$^-$.

Further, the epitopes within HPV16 E6 and E7 proteins were also identified based on the magnitude of immune response. The number of peptide-specific CD8 T cells in an established T cell lined from one subject (subject 1) was quantified. This subject was HLA-A2.1 positive and had ar HPV16 infection at the age of 26 years, which was cleared 29 months prior to drawing of blood Overlapping 15-mer peptides pooled in groups of three spanning all the E6 and E7 proteins were used it a IFN-γ ELISPOT assay. Responses to the E6 46-70 (SEQ ID NO: 38) and E7 76-98 (SEQ ID NO: 64) regions were demonstrated, with the response to the E6 epitope being larger than that to the E7 epitope (FIG. 10).

Figure 11A:
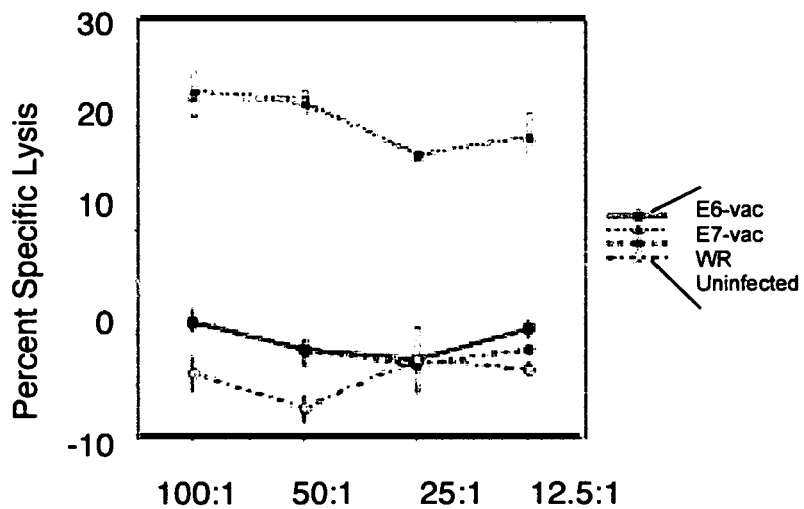
FIGS. 11A-F show results of chromium release and ELISPOT assays performed to characterize the E7 epitope from subject 1.
Figure 11B:
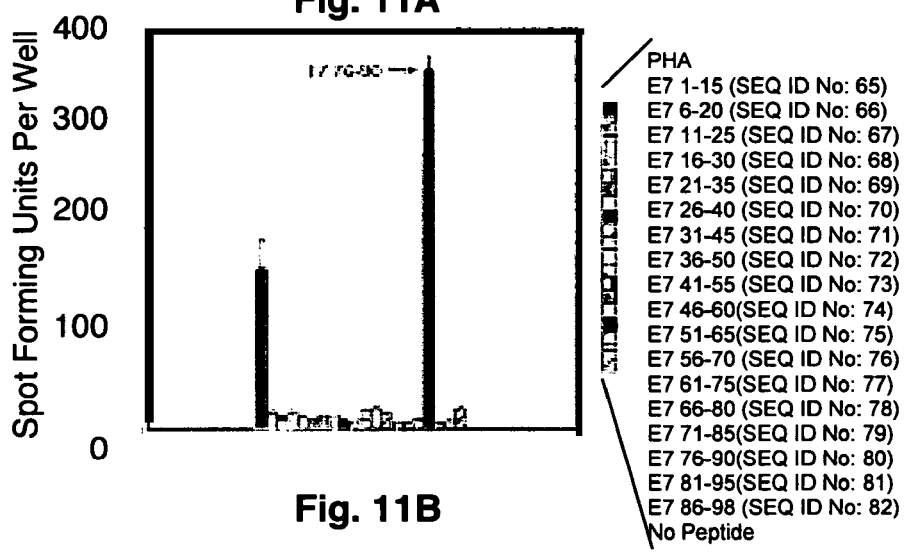
Figure 11C:
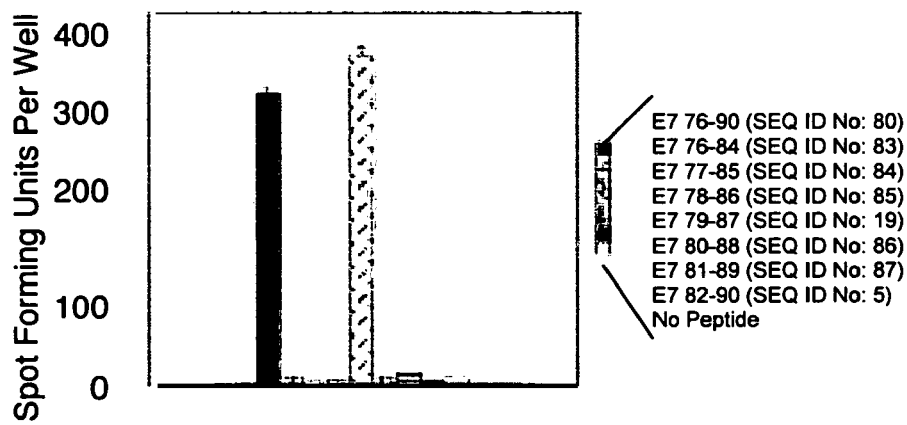
Figure 11D:
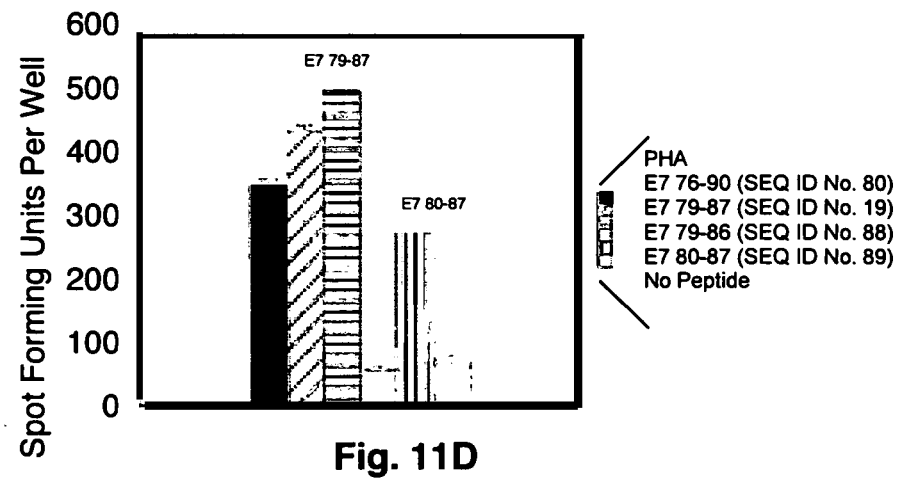

The T cell clones recognizing these antigenic epitopes were isolated by performing limiting dilution by plating 0.5 cells per well of the CD8 T cell line without selection for IFN-γ secretion. A total of $3 \times 10^3$ cells were plated and 348 of the 586 clones that grew were screened by a chromium release assay, using E6-vac or E7-vac-infected autologous EBV-LCL. Of the 348 T cell clones that were tested, 1 (the 27G6 clone) had an E7 specificity (FIG. 11A). By using overtapping 15-mer peptides covering the E7 protein the epitope recognized by this T cell clone was shown to be in the E7 76-90 (IRTLEDLLMGTLGIV; SEQ ID NO: 80) peptide (FIG. 11B). The epitope was further defined using an overlapping 9-mer within the 15-amino acid region of the E7 79-87 peptide [LEDLLMGTL: SEQ ID NO: 19) (FIG. 11C). Examination of the shorter 8-mer peptides (E7 79-86 (LEDLLMGT; SEQ ID NO: 88] and E7 80-87 [EDLLMGTL: SEQ ID NO: 89]) demonstrated a smeller response compared to that for the E7 79-87 (9-mer; SEQ ID NO: 19) (FIG. 11D).

Figure 11E:
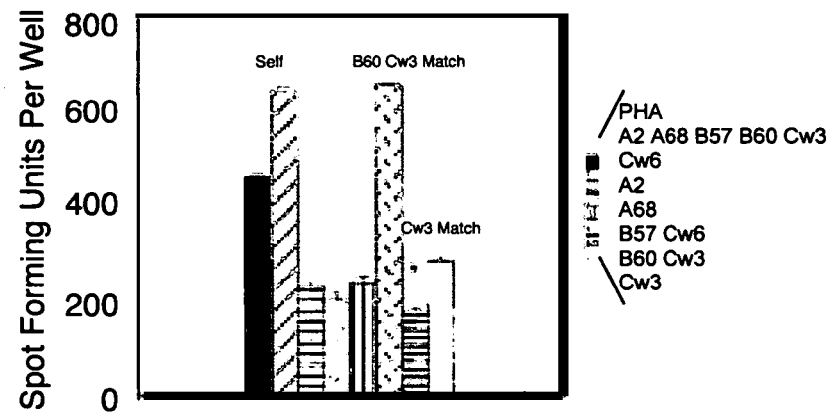
Figure 11F:
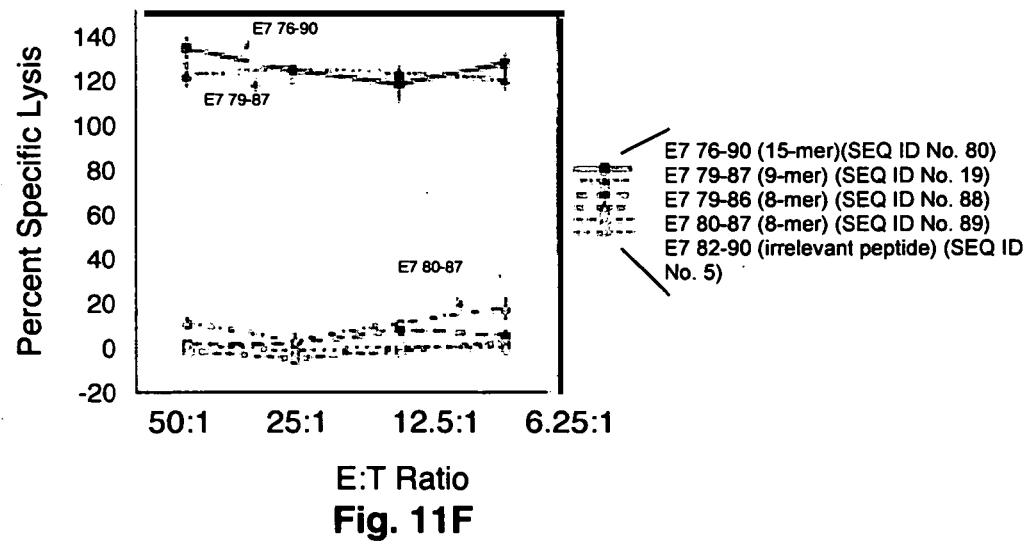

Using allogeneic EBV-LCL sharing the HLA class I molecules with subject 10, the restriction element for the E7 79-87 (SEQ ID NO: 19) epltope was investigated. The results suggested the HLA-B60 molecule to be its restriction element (FIG. 11E). The 9-mer peptide E7 79-87 (SEQ ID NO: 19) did not contain the known HLA-B60 motif, which included a glutamic acid residue at position 2 and a leucine residue at position 9. This explained why the E7 80-87 (8-mer, SEQ ID NO: 89) peptide, which contained both anchor residues exhibited partial IFN-γ secretion while E7 79-86 (8-mer; SEQ ID NO: 88) which contained only one of the two anchor residues did not show any activity above the background (FIG. 11D). Although these results were similar to those of the chromium release assay, the quantitative difference between the strength of immunogenicity of E7 76-90 (15-mer; SEQ ID NO: NO. 80) and E7 79-87 (9-mer; SEQ ID NO: 19) was not apparent in the chromium release assay (FIG. 11F). Additionally, the difference between the activity of £7 79-86 (8-mer, SEQ ID NO: 88) and E7 80-87 (B-mer; SEQ ID NO: 89) was less obvious as well. However, the ELISPOT assay had an advantage of requiring only $10^3$ T cell clones per well, which meant that this assay required 1/60 of the number of T cell clones used in chromium release assay.

A second CD8 T cell line was generated from the same subject 10 using autologous dendritic cells pulsed with the peptide pool to which this subject demonstrated a response (E6 46-60 (SEQ ID NO: 111), E6 51-65 (SEQ ID NO: 90) and E6 56-70 (SEC) ID NO: 112) peptides). Stimulation was done using peptides since this induced a more robust proliferation of T cells than stimulation with recombinant vaccinia virus-infected antigen-presenting cells. The frequencies of the peptide-specific T cells were 0.09, 0.11 and 0.04%, respectively. The T cells with specificity to three peptides were isolated magnetically for IFN-γ production before performing the limiting dilution assay. One thousand cells selected on the basis of IFN-γ secretion were plated.

An ELISPOT assay was performed on 94 randomly selected clones of the 480 clones that grew after the limiting dilution experiment. Each clone plated in quadruplicate was tested separately with E6 46-60 (SEQ ID NO: 111), E6 51-65 (SEQ ID NO: 90), E6 56-70 (SEQ ID NO: 112) and the no peptide control. A total of 18 T cell clones were positive for the E6 46-60 (SEQ ID NO: 111) peptide, 6 clones were positive for E6 51-65 (SEQ ID v 90), 18 clones were positive for both E6 46-80 (SEQ ID NO: 111) and E6 51-65 (SEQ ID NO: 90) and 1 Clone was positive for E6 56-70 (SEQ ID NO: 112).

To further define the peptide contained within the E6 epitope, eight representative clones (two positive for E6 46-60 (SEQ ID NO: 111), two positive for E6 51-65 (SEQ ID NO: 90) and one positive for E6 56-70 (SEQ ID NO: 112)) were examined to determine if they recognized naturally processed epitopes by testing their recognition of E6-vac-infected autologous EBV-LCL. This criteria was used to distinguish T cell clones of interest from Irrelevant T cell clones because the first CD8 T cell line was established using autologous dendritic cells infected with vaccinia viruses expressing the E6 protein. Three of the eight clones that positively recognized E6-vac-infected autologous EBV-LCL did not recognize those Infected with E7-vac or wild type, suggesting that these clones were specific for a naturally processed epitope of the E6 protein (FIG. 12A).

Using overlapping 9-mer peptides within this region, the epitope was determined to be E6 53-61 (AFRDLCIVY; SEQ ID NO: 98) (FIG. 12B). However, the response to the 15-mer E6 51-65 (SEQ ID NO: 90) was greater than to the 9-mer E6 53-61 (SEQ ID NO: 98), thereby suggesting that the optimal sequence of this epitope was longer than 9 amino acids. The peptide sequences E6 53-60 (AFRDLCIV; SEQ ID NO: 106) (8-mer), E6 54-61 (FRDLCIVY; SEQ ID NO: 107) (8-mer), E6 53-61 (9-mer; SEQ ID NO: 98), E6 53-62 (10-mer; SEQ ID NO: 105), E6 52-61 (FAFRDLCIVY; SEQ ID NO: 16) (10-mer), E6 51-61 (DFAFRDLCIVY; SEQ ID NO: 104) (11-mer), E6 52-62 (FAFRDLCIVYR; SEQ ID NO: 103) and E6 51-65 (15-mer; SEQ ID NO: 90) were examined to determine the shortest optimal peptide sequence. The optimal sequence was found to be the 10-mer E6 52-61 (SEQ ID NO: 16) (FIG. 12C), The restriction element for the E6 52-61 (SEQ ID NO: 16) was likely to be the HLA-B57 molecule (FIG. 12D). The surface phenotypes of all the three T cell clones were CD3$^+$CD4$^-$CD8$^+$CD16$^-$.

EXAMPLE 13

Expression of the HPV16 E6 52-61 (SEQ ID NO: 16) Epitope by Primary Tumor Cell Lines Established from Cervical Cancer In order to assess the potential for using the CD8 T cell epitopes described above as sources of antigens for dendritic cell immunotherapy, their expression on primary tumor cell lines derived from cervical cancer were examined. Three HLA-B57 positive primary tumor cell lines (patient #1, #2 and #3) were available to test the HPV16 E6 52-61 (SEQ ID NO: 16) epitope. These and other cell lines described in Table 5 were established as described earlier.

An ELISPOT assay was performed in which 1×10$^3$ HPV16 E6 52-61 (SEQ ID NO: 16) specific T cell clones were incubated with 1×10$^5$ tumor cell lines in triplicate. To augment expression of co-stimulatory molecules, primary tumor cells were treated with 500 u/ml of IFN-$\gamma$ for 48 hrs and then tested. Further EBV-LCLS were available from the subject from whom the T cell clone was isolated (subject #15), patient #1 and patient#2 although the one from patient #2 was growing poorly. 1×10$^3$ T cell clones were incubated with these EBV-LCLs (1×10$^5$ per well except for patient#2 for whom only 3×10$^4$ cells were available) in the presence of 10 µM of the E6 52-61 (SEQ ID NO: 16) peptide. The experiment was performed in triplicate and PHA wells were used as positive control. IFN-$\gamma$ secretions were detected for all peptide-pulsed EBV-LCLs although the magnitude was less for patient #2 (208.7±26.8 spot forming units per well for subject #15, 191.0 28.5 for patient #1, 158.0±8.5 for patient #2), few if any spot forming units were present in any of the wells with the primary tumor cells (data not shown).

TABLE 5

HLA types of cervical cancer patients from whom HPV16-positive primary tumor cell line were derived

| Patient# | Histology | Class I | Class II |
|---|---|---|---|
| 1 | Squamous cell | A1, A2, B35, B57, Cw6 | DR1, DR3, DR7, DR53, DQ5, DQ9 |
| 2* | Squamous cell | A30, B53, B57, Cw4, Cw7 | DR13, DR15, DQ2, DQ6, DR51, DR52 |
| 3 | Squamous cell | A1, A2, B50, B57, Cw6 | DR3, DR7, DR53, DQ2, DQ9 |
| 4 | Squamous cell | A68, B53, Cw4, Cw6 | DR4, DR13, DQ7, DQ8, DR52, DR53 |
| 5 | Squamous cell | A1, A2, B7, B41, Cw7 | DR11, DR15, DR51, DR52, DQ6 |

*Loss of surface expression of HLA class I type observed by FACS analysis using HLA class I-specific monoclonal antibody (W6/32).

The same primary tumor cell lines were tested using chromium release assay (FIGS. 13A-D). The HPV16 E6 52-61 (SEQ ID NO: 16) peptide was added to the tumor cells as well as to the EBV-LCL in order to assess the ability of the HLA molecules to present antigen. 3×10$^3$ target cells were plated in triplicate. Untreated tumor cells (FIG. 13A) from patient #1 and #3 seemed to demonstrate very weak cytolysis. Treatment with IFN-$\gamma$ enhanced the killing of tumor cells of patient#1 and #3 to more discernable levels (FIG. 13B). Therefore, it appeared that these tumor cells were expressing the HPV16 E6 52-61 (SEQ ID NO: 16) epitope. When peptides were added to the tumor cells, the levels of killing enhanced for subject 1 and 3 (FIG. 13C). However, no killing was observed for subject #2. These results were consistent with earlier surface staining results that showed little expression of HLA class I molecules for this patient's tumor cell line. The treatment with IFN-$\gamma$ and pulsing with peptide greatly enhanced killing of #1 tumor cells but that of tumor cells of #3 were unchanged from peptide pulsed but IFN-$\gamma$ untreated cells (FIG. 13D). These results demonstrated that the CD8 T cell epitopes were processed and expressed by the tumor cells. The reason for all three primary tumor cell lines to be negative for ELISPOT was not clear. One possibility was mechanical obstruction by tumor cells, which are larger and flatter cells than the cells of EBV-LCL. The IFN-$\gamma$ secreted by the T cell clone cells trapped in between tumor cells, might have been dispersed prior to reaching the membrane. Therefore, the use of less number of tumor cells will also be explored.

EXAMPLE 14

Pattern of CD8 T Cell Epitopes in the HPV16 E6 and E7 Proteins in Women with SIL Based on the hypothesis that more potent epitopes will be better source of immunogen for dendritic cell immunotherapy, it is contemplated to identify CD8 T cell epitopes to which strongest CD8 T cell responses are demonstrated. These CD8 T cell epitopes will be identified in women who have abnormal pap smear results indicating that they have SIL and test positive for HPV16 DNA. The HPV DNA will be tested in cervical swab specimens by PCR with sequence specific primers for the E7 oncoproteins.

Briefly, for HPV16: 0.1-1 µg of each genomic DNA sample will be amplified in a 50 µl reaction containing 0.3 µM of each of the individual primers (HPV16 E7: F5'-ATGGAGATA-CACCTACATTGC-3' (SEQ ID NO: 113); R5'-GGTTTCT-GAGAACAGATGGGGC-3' (SEQ ID NO: 114)) in presence of 1×PCR buffer, 2.5 µM MgCl$_2$, 0.8 µM dNTPs and 0.025 U/µl U AmpliTaq DNA polymerase (Applied Biosystems, Foster City, Calif.). Amplifications will be performed in the Applied Biosystems GeneAmp PCR System 2700 (Applied Biosystems, Foster City, Calif.) at 95° C. for 3 minutes, followed by 35 cycles of 95° C. for 30 seconds, 60° C. for 30 seconds, 72° C. for 1 minute and a final extension of 72° C. for 7 minutes. The PCR products will be stored at 4° C. before electrophoresis on a 2% agarose gel. Beta-tubulin gene will be amplified using the following primers: F5'-CGCAT-CAACGTGTACTACAA-3' (SEQ ID NO: 115), R5'-TAC-GAGCTGGTGGACTGAGA-3' (SEQ ID NO: 116) (0.25 μM of each primer) will be used as appositive internal control. SiHa (HPV16) cervical carcinoma cell line DNA will be used as a positive external control. HT-3 (HPV-negative) cell line DNA and a water template will be used as negative controls. Women who test positive for HPV16 will further undergo phlebotomy to establish CD8 T cell lines. The CD8 T cell fines from these women will be established by in vitro stimulation of CD8 cells using autologous dendritic cells infected with recombinant vaccinia viruses expressing the E6 and E7 proteins. The same procedure as described earlier will be followed. Further, an ELISPOT assay using overlapping peptides covering the E6 and E7 proteins of HPV18 or HPV52 will be performed as described earlier. However, instead of using 15-mer peptides overlapping by 10 amino acids, peptides designed by PeptGen, a program designed to create maps of overlapping peptides for the purpose of epitope mapping www.hiv.lanl.gov/content/hiv-db/PEPTGEN/PeptGen-SubmitForm.html) will be used (Table 6). Three consecutive peptides will be pooled and tested.

TABLE 6

Overlapping peptides designed by PeptEGN For HPV 16

| HPVL6 E6 | | | | HPV16 E7 | | | |
|---|---|---|---|---|---|---|---|
| Residue | Length # | Sequence (amino acid) | SEQ ID NO. | Residue | Length # | Sequence (amino acid) | SEQ ID NO. |
| 1-15 | 15 | MHQKRTAMFQDPQER | 108 | 1-15 | 15 | MHGDTPTLHEYMLDL | 65 |
| 5-19 | 15 | RTAMFQDPQERPRKL | 117 | 5-19* | 15 | TPTLHEYMLDLQPET | 157 |
| 9-22 | 14 | FQDPQERPRKLPQL | 118 | 9-23 | 15 | HEYMLDLQPETTDLY | 158 |
| 12-26 | 15 | PQERPRKLPQLCTEL | 119 | 13-25 | 13 | LDLQPETTDLYCY | 159 |
| 16-30 | 15 | PRKLPQLCTELQTTI | 45 | 15-28 | 14 | LQPETTDLYCYEQL | 160 |
| 20-34 | 15 | PQLCTELQTTIHDII | 120 | 18-32* | 15 | ETTDLYCYEQLNDSS | 161 |
| 24-38 | 15 | TELQTTIHDIILECV | 121 | 22-38 | 17 | LYCYEQLNDSSEEEDEI | 162 |
| 28-41 | 14 | TTIHDIILECVYCK | 122 | 28-42 | 15 | LNDSSEEEDEIDGPA | 163 |
| 31-45 | 15 | HDIILECVYCKQQLL | 123 | 32-45 | 14 | SEEEDEIDGPAGQA | 164 |
| 35-49 | 15 | LECVYCKQQLLRREV | 124 | 35-49 | 15 | EDEIDGPAGQAEPDR | 165 |
| 39-53 | 15 | YCKQQLLRREVYDFA | 125 | 39-52 | 14 | DGPAGQAEPDRAHY | 166 |
| 41-55 | 15 | KQQLLRREVYDFAFR | 126 | 42-55 | 14 | AGQAEPDRAHYNIV | 167 |
| 45-59 | 15 | LRREVYDFAFRDLCI | 127 | 45-57 | 13 | AEPDRAHYNIVTF | 168 |
| 49-62 | 14 | VYDFAFRDLCIVYR | 128 | 47-60 | 14 | PDRAHYNIVTFCCK | 169 |
| 52-67 | 16 | FAFRDLCIVYRDGNPY | 129 | 50-65 | 16 | AHYNIVTFCCKCDSTL | 170 |
| 57-69 | 13 | LCIVYRDGNPYAV | 130 | 55-69 | 15 | VTFCCKCDSTLRLCV | 171 |
| 59-72 | 14 | IVYRDGNPYAVCDK | 131 | 59-73 | 15 | CKCDSTLRLCVQSTH | 172 |
| 62-76 | 15 | RDGNPYAVCDKCLKF | 132 | 63-77 | 15 | STLRLCVQSTHVDIR | 173 |
| 66-80 | 15 | PYAVCDKCLKFYSKI | 133 | 67-79 | 13 | LCVQSTHVDIRTL | 174 |
| 70-84 | 15 | CDKCLKFYSKISEYR | 134 | 69-83 | 15 | VQSTHVDIRTLEDLL | 175 |
| 74-88 | 15 | LKFYSKISEYRHYCY | 135 | 73-87 | 15 | HVDIRTLEDLLMGTL | 176 |
| 78-91 | 14 | SKISEYRHYCYSLY | 136 | 77-90 | 14 | RTLEDLLMGTLGIV | 177 |
| 81-95 | 15 | SEYRHYCYSLYGTTL | 137 | 80-93 | 14 | EDLLMGTLGIVCPI | 178 |
| 85-99 | 15 | HYCYSLYGTTLEQQY | 138 | 83-98 | 16 | LMGTLGIVCPICSQKP | 179 |
| 89-103 | 15 | SLYGTTLEQQYNKPL | 139 | | | | |
| 93-107 | 15 | TTLEQQYNKPLCDLL | 140 | | | | |
| 96-109 | 14 | EQQYNKPLCDLLIR | 141 | | | | |

TABLE 6-continued

Overlapping peptides designed by PeptEGN For HPV 16

| | HPVL6 E6 | | | | HPV16 E7 | | |
|---|---|---|---|---|---|---|---|
| Residue | Length # | Sequence (amino acid) | SEQ ID NO. | Residue | Length # | Sequence (amino acid) | SEQ ID NO. |
| 99-111 | 13 | YNKPLCDLLIRCI | 142 | | | | |
| 101-115 | 15 | KPLCDLLIRCINCQK | 143 | | | | |
| 105-117 | 13 | DLLIRCINCQKPL | 144 | | | | |
| 107-122 | 16 | LIRCINCQKPLCPEEK | 145 | | | | |
| 112-126 | 15 | NCQKPLCPEEKQRHL | 146 | | | | |
| 116-129 | 14 | PLCPEEKQRHLDKK | 147 | | | | |
| 119-133 | 15 | PEEKQRHLDKKQRFH | 148 | | | | |
| 122-136 | 15 | KQRHLDKKQRFHNIR | 149 | | | | |
| 126-139 | 14 | LDKKQRFHNIRGRW | 150 | | | | |
| 129-142 | 14 | KQRFHNIRGRWTGR | 151 | | | | |
| 132-144 | 13 | FHNIRGRWTGRCM | 152 | | | | |
| 134-148 | 15 | NIRGRWTGRCMSCCR | 153 | | | | |
| 138-151 | 14 | RWTGRCMSCCRSSR | 154 | | | | |
| 141-154 | 14 | GRCMSCCRSSRTRR | 155 | | | | |
| 144-158 | 15 | MSCCRSSRTRRETQL | 156 | | | | |

*forbidden peptides. The program was instructed to avoid N-terminal and C-terminal amino acids as these make the peptides unstable for binding by shortening or lengthening the peptides by a few amino acids.

Each subject are HLA typed for class I molecules to identify the restriction elements of the new antigenic epitopes. A total of $2 \times 10^6$ to $3 \times 10^6$ PBMCs from each subject are sent for DNA-based typing, which is designed to determine low-resolution HLA types. This method approximates conventional serological typing. Sequence-specific amplification using 96 PCR reactions will be used for low resolution HLA-A, -B and -C typing. Each reaction will contain one or more pairs of primers that will detect polymorphic HLA sequences, which are associated with low-resolution HLA types along with an additional primer pair that will serve as an internal control for amplification competence.

The results of each ELISPOT assay performed are calculated and graphed individually. Peptide pools for which the number of spot forming units exceeds those in the no peptide control wells will be considered positive. CD8 T cell lines containing any positive peptide pool will be used further. Further, percentage of subjects with at least one positive peptide pool will be calculated. If there are particular region(s) of the E6 or E7 protein that is/are frequently positive, its/their significance will be assessed statistically. For example, if the N-terminal half of the E6 protein contains positive peptide pools frequently, Fisher's exact test will be performed.

EXAMPLE 15

Amino Acid Sequence and the Restricting HLA Molecules of CD8 T Cell Epitopes.

Since the number of circulating CD8 T lymphocytes specific for pathogen that cause local infection such as HPV is low, the identification of CD8 T cell epitopes to such pathogens is challenging. However, this limitation is overcome by optimizing the in vitro stimulation protocol and by isolating T cell clones on the basis of IFN-γ secretion prior to performing a limiting dilution analysis. The CD8 T cell line undergoes two additional 7-day cycles of in vitro stimulation so that the amount of target T cells is above the threshold of isolation (>0.1%). The frequency will be determined by testing peptides contained in the positive pool in separate wells in an ELISPOT assay. Further, antigen-specific T cells are selected using the IFN-γ secretion assay enrichment kit as described earlier.

In order to screen CD8 T cell clones, a total of 94 randomly selected clones are tested in quadruplicate since each of the peptides in the peptide pools are tested on separate ELISPOT plates along with no-peptide control plate. The ELISPOT plates are coated with primary anti-IFNγ monoclonal antibody and washed as described earlier. After blocking, T cell clones from the 24-well plates, resuspended in 50 μl of media are plated in one well in each of the four plates. One well is used as a no-cell negative control; one is used as a PHA-positive control. The first peptide from the pool is added to the first ELISPOT plate at a concentration of 10 μM, the second peptide is added to the second ELISPOT plate, the third peptide is added to the third ELISPOT plate and no peptide is added to the fourth plate. The ELISPOT plates are incubated and developed as described earlier. The wells that show spots in an ELISPOT plate with one peptide but not in other ELISPOT plates are likely to contain T cell clones with specificity of interest. The T cell clones that are positive in the screening will be retested.

Further, whether the T cell epitope is naturally processed is assessed by performing another ELISPOT assay using recombinant vaccinia virus. Autologous EBV-LCL cells are infected with E6-vac or E7-vac at the multiplicity of infection of 10 for 1 h prior to being added to the ELISPOT plate. A negative control comprising wild type vaccinia viruses will be used for comparison. Briefly, EBV-LCLs will be established as follows: $10 \times 10^6$ to $20 \times 10^6$ PBMCs will be incubated with occasional mixing for 90 min with supernatant fluid of B958 containing free EBV virions. Ninety percent of the EBV virions will be removed by centriftigation and the PBMCs will be grown in RPMI 1640 containing 10% fetal calf serum (FCS), penicillin G (1000 units/ml), streptomycin (1000 μg/ml) and cyclosporine A. The PBMCs are then incubated and monitored for growth of characteristic cell clumps.

In order to identify the minimal and optimal amino acid sequence of the T cell epitope, ELISPOT assays are performed using 9-mer peptides overlapping by the central 8 amino acids, which covers the peptide to which the epitope has been narrowed down to. For a 15-mer peptide, seven 9-mers will be needed. Once the 9-mer, which contains the epitope is identified, 8-mers within the 9-mer and 10-mers flanking the 9-mers are synthesized and tested. The shortest peptide demonstrating strong positivity is designated the minimum optimal peptide. In cases where the results are not clear, peptides are serially diluted and tested with ELISPOT assay. The peptide with the positivity at the wider concentration are designated as minimum optimal peptide.

Further, the restricting HLA molecule are identified using both ELISPOT and chromium release assays. Six allogeneic EBV-LCLs sharing one HLA class I molecule with the subject are used for the ELISPOT assay ($1 \times 10^3$ T cell clones are plated along with $1 \times 10^5$ allogeneic EBV-LCL cells per well in triplicate). The HLA type shared between the subject and the allogeneic EBV-LCL with the largest number of spot forming unit will be the restriction element. This will be confirmed using a chromium release assay as discussed earlier. Additionally, the T cell clones for which the peptide specificities are confirmed are analyzed for their surface phenotypes by staining with anti-CD4, anti-CD8 and anti-CD3, anti-CD16 antibodies. This analysis will also confirm that the T cell lines that were selected are CD8 positive.

EXAMPLE 16

Expression of HPV16 E6 and E7 CD8 T Cell Epitopes by Primary Tumor Cell Lines Derived from Patients with Cervical Cancer.

To be useful as targets of immunotherapy, the CD8 T cell epitopes have to be expressed by tumor cells. Primary tumor cell lines are established after sterile processing of samples from surgical biopsies of patients diagnosed with frankly invasive stage IB-IIA cervical cancer (staged according to the F.I.G.O. operative staging system) obtained at the time of surgery and/or staging. Briefly, single cell suspensions are obtained by processing solid tumor samples under sterile conditions at room temperature. Viable tumor tissue are mechanically minced in RPMI 1640 to portions no larger than 1-3 mm$^3$ and washed twice with RPMI 1640. The portions of the minced tumor will then be placed into 250 ml flasks containing 30 ml of enzyme solution (0.14% Collagenase Type I (Sigma) and 0.01% DNAse (Sigma, 2000 KU/mg) in RPMI 1640 and incubated on a magnetic stirring apparatus either for 2 hrs at 37° C. or overnight at 4° C. Enzymatically dissociated tumor are then washed twice in RPMI 1640 plus 10% human AB serum (Gemini Bioproducts, Calabasas, Calif.) before being seeded in tissue culture flasks in serum-free keratinocyte medium, supplemented with 5 ng/ml epidermal growth factor and 35 to 50 μg/ml bovine pituitary extract (Invitrogen, Grand Island, N.Y.) at 37° C.

In order to assess the expression of the newly described CD8 T cell epitope, a primary tumor positive for HPV16 and for the HLA restricting molecule are needed. The class I HLA types represented in the collection of the HPV16-positive primary tumor cell lines are HLA-A1, A2, A30, A68, B7, B35, B41, B50, B53, B57. Cw4, Cw6, Cw7. The frequencies of these HLA antigens in different racial groups are summarized in Table 7.

TABLE 7

The population frequencies (%) of HLA class I antigens represented in the current collection of tumor cell lines positive for HPV16 (Marsh, S.G.E. et al., 2000)

| Race/HLA | A1 | A2 | A30 | A68 | B7 | B35 | B41 | B50 | B53 | B57 | Cw4 | Cw6 | Cw7 |
|---|---|---|---|---|---|---|---|---|---|---|---|---|---|
| Black | 4.9 | 15.8 | 14.5 | 9.7 | 7.7 | 5.5 | 2.4 | 0.6 | 5.5 | 4.0 | 15.8 | 15.1 | 21.3 |
| Caucasian | 14.1 | 25.0 | 3.4 | 4.0 | 8.7 | 10.3 | 1.5 | 1.2 | 1.0 | 2.9 | 12.4 | 9.6 | 22.9 |
| Other | 3.7 | 27.2 | 2.1 | 1.3 | 3.4 | 5.0 | 0.3 | 0.5 | 1.0 | 1.3 | 7.9 | 6.6 | 15.1 |

The expression of HPV16 E6 or E7 CD8 T cell epitopes by the primary tumor cell line are assessed by an ELISPOT assay as described earlier. As described earlier, analogous wells with cells of the primary tumor cell line treated with IFN-γ for 48 hrs are set up. The positive control for the expression of correct HLA antigen will be EBV-LCL, established from the patient whose primary tumor cell line is pulsed with the peptide. Additionally, the expression of the T cell epitope by the primary tumor cell line will also be assessed by the chromium release assay as described earlier.

EXAMPLE 17

Cross-Recognition of Analogous CD8 T Cell Epitopes of HPV16 Variants and Other High-Risk HPV Types The HPV16 E6 and E7 CD8 T cell epitopes identified by the methods described earlier could be used broadly as the source of antigens for immunotherapy if the specific T cells also recognized analogous epitopes in HPV16 variants and in other high-risk HPV types. Therefore, published sequences of HPV16 variants and of high-risk HPV types other than 16 will be examined for the presence of "analogous" epitopes in the same region as the HPV16 E6 or E7 CD8 T cell epitope. The presence of analogous epitopes is defined as those peptides that contain the same anchor residues (amino acid #2 and the last amino acid residue of the CD8 T cell epitope) as the original HPV16 epitope will be searched among published HPV16 variant sequences and the sequences of other high-risk HPV types.

The sequences of HPV16 variants described prior to 1995 will be obtained from a compendium (hpv-web.lanl.gov/std-gen/virus/hpv/compondium/htdocs/COMPENDIUM PDF/95PDF/1?16var.pdf). The more recently described sequences of HPV16 variants will also be included (Wheeler, C. M. et al., 1997). The sequences of other high-risk HPV types (HPV 18, 31, 33, 35, 39, 45, 51, 52, 56, 58, 59, 68 and 73) available at the HPV sequence database (hpv-web.lanl.gov/stdgen/virus/hpv/) will also be included. Synthetic peptides with the sequences of analogous epitopes will also be synthesized. The number of analogous epitopes will vary from epitope to epitope. For example, there are 12 analogous peptides for HPV16 E6 52-61 (SEQ ID NO: 16) epitope. They are from HPV 18, 31, 33, 35, 39, 45, 51, 58, 59, 68 and 73. Similarly, there are 7 analogous peptides [from HPV33 (aa22-aa30, TIHNIELQC; SEQ ID NO: 180), 35 (aa22-aa30, SIHEICLNC; SEQ ID NO: 181), 73 (23-31, SIHDINLDC; SEQ ID NO: 182) and HPV16 variants (n=4)] for HPV16 E6 29-37 (SEQ ID NO: 15) epitope and 2 analogous peptides from HPV68 (aa84-aa92, RENLRNVEL; SEQ ID NO: 183) and 73(IEELLMGTL; SEQ ID NO: 184) for the HPV16 E7 79-87 (SEQ ID NO: 19) epitope.

The cross presentation of the analogous peptide are examined by ELISPOT and chromium release assays. The ELISPOT assay will be performed using multiple dilutions of the peptide (10 μM, 1 μM, 0.1 μM, 0.01 μM and 0.001 μM) as described earlier. The chromium release assay are performed as described earlier using different effector to target ratios such as 40:1, 20:1, 10:1 and 5:1 and different dilutions of the peptide (10 μM, 1 μM, 0.1 μM).

EXAMPLE 18

HLA class I Promiscuity in the HPV16 Protein

The CD8 T cells from subjects who demonstrated the potential presence of dominant epitopes in the HPV16 E6 16-40 region were characterized further with regards to their HLA molecules. HLA class I typing was performed as described supra. Overlapping 9-mer peptides (overlapping by 8 amino acids), 15-mer peptides (overlapping by 10 amino acids), 7-mers, 8-mers, 10-mers and 11-mers of the HPV protein were synthesized to define the minimal and optimal amino acid sequences of the CD8 T cell epitopes. The amino acid sequences of all the peptides were derived from the HPV16 German prototype. Magnetic selection of IFN-gamma secreting T cells and the ELISPOT assay to screen for T cell clones were performed as described supra.

In order to assess whether the T cell clones recognized endogenously proceesed peptide antigen, autologous LCL infected with recombinant vaccinia virus expressing HPV16 E6 (E6-vac) at MOI of 10 or 5 were used as antigen presenting cells (APC) in ELISPOT assays. The wild type virus, Western Reserve and recombinant vaccinia virus expressing HPV16 E7 were used as negative controls. Autologous LCL was washed twice using RPMI with 1% pooled human serum and appropriate amounts of virus were added to respective tubes. They were incubated at 37° C. for 1 h with mixing every 20 mins. One thousand T cell clones were plated per well along with $1 \times 10^5$ infected autologous LCL cells in duplicates or triplicates and ELISPOT assays carried out as described supra.

The standard approach to define the minimal and optimal peptide antigen epitope was to determine which of the three 15-mer was positive in each peptide pool followed by testing of overlapping 9-mer peptides within the positive 15-mer peptide. All peptides were used at a concentration of 10 μm and $1 \times 10^3$ T cell clones along with $1 \times 10^5$ autologous LCL cells were plated to each well. The minimal and optimal peptide was defined as the shortest peptide which was able to elicit the highest number of spot forming units. When there was an uncertainty as to which peptide may be minimal and optimal, the candidate peptides were serially diluted ($10^{-5}$ M to $10^{-10}$ M) and the shortest peptide with more spot forming units at the lower concentrations of the peptide was determined to be minimal and optimal.

The putative restricting HLA class I molecule was identified using allogeneic LCL sharing one or a few class I molecules using an ELISPOT assay in such a manner that all of subjects' HLA class I molecules (A, B, and C) were examined. Autologous LCL was used as a positive control. One thousand T cell clone cells, $1 \times 10^5$ allogeneic LCL, and the antigenic peptide were plated in triplicates, and the assay was performed as described supra. The chromium release assays were performed as described supra to confirm the ELISPOT results using multiple allogeneic LCL expressing the putative restricting HLA class I molecule. Additionally, FACS analysis was carried out as described supra using FACS Calibur (Beckton Dickinson Immunocytometry systems, San Jose, Calif.) or Coulter EPICS XL-MLC flow cytometer (Beckman Coulter, Fullerton, Calif.).

Results:

The frequencies of T cells specific for the potential dominant epitopes were 0.05%, 0.02%, 0.04%, and 0.05% of CD8 T cells for subjects 5, 7, 15, and 20, respectively (Table 3). Two to $7.1 \times 10^6$ cells of the CD8 T cell lines were used per subject for magnetic selection, and the yields of IFN-g positive cells were 0.21%, 2.7%, 0.46%, and 0.52%, respectively. Half or all of IFN-gamma positive cells were used for limiting dilution, and 95 to 400 T cell clones per subject that grew well were expanded in 24 well plates two weeks after limiting dilution. Ninety-four to 188 T cell clones were screened using IFN-gamma ELISPOT assay, and most or all of T cell clones that demonstrated higher number of spot forming units with a peptide or a peptide pool compared with the no peptide control were retested with individual 15-mer peptides and with E6-vac infected autologous LCL (FIG. 14).

Figure 14A:
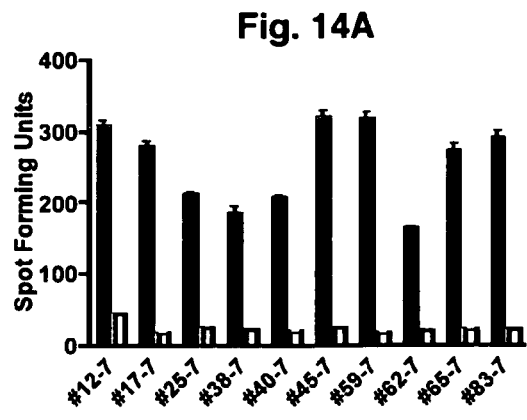
FIGS. 14A-E show that the T-cell clones from subject 7, 15, and 20 recognized naturally processed E6 epitopes using an ELISPOT assay. The number after the dash indicates subject of origin.
Figure 14D:
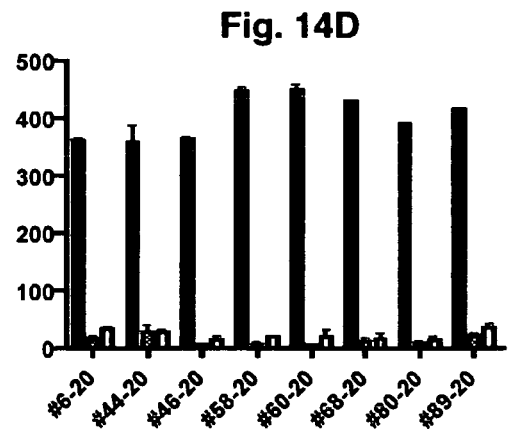
Figure 14B:
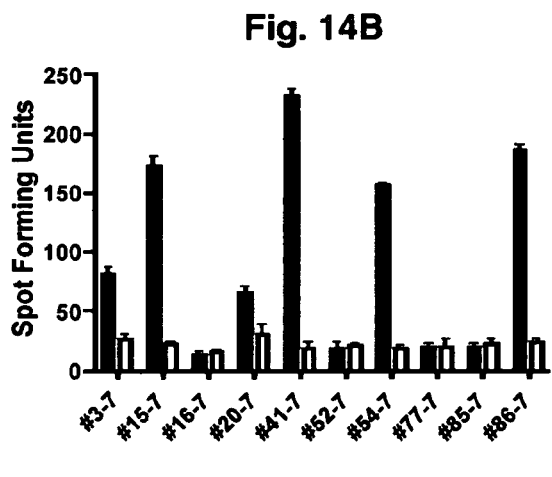
Figure 14E:
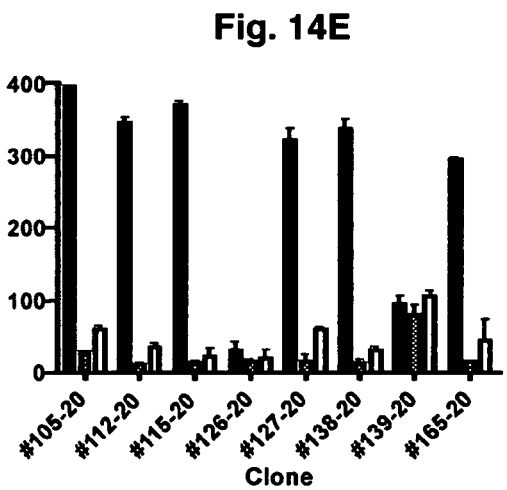
Figure 14C:
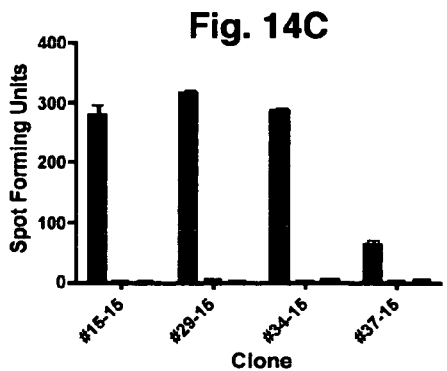

For subject 7, 10 (#12-7, #17-7, #25-7, #38-7, #40-7, #45-7, #59-7, #62-7, #65-7, #83-7) of 10 T cell clones positive for E6 16-40 region (SEQ ID NO: 36) In the screening ELISPOT assay were positive for the E6 26-40 (SEQ ID NO: 47) 15-mer peptide, and 20 of 20 T cell clones were positive with E6-vac infected autologous LCL (FIG. 14A). For the E6 46-70 (SEQ ID NO: 38) region, all six (#3-7, #15-7, #20-7, #41-7, #54-7, and #86-7) of T cell clones were positive for the E6 51-65 15-mer peptide, and six of 10 T cell clones were positive for E6-vac infected autologous LCL (FIG. 14B). For subject 15, 10 (#1-15, #15-15, #27-15, #29-15, #34-15, #37-15, #68-15, #77-15, #92-15, #93-15) of 14 CD8 T cell clones positive for the E6 16-40 (SEQ ID NO: 36) region were positive for the E6 26-40 (SEQ ID NO: 47) 15-mer peptide, and 10 of 14 T cell clones were positive with E6-vac infected autologous LCL (FIG. 14C). For subject 20, all eight (#6-20, #44-20, #46-20, #58-20, #60-20, #68-20, #80-20, and #89-20) of CD8 T cell clones positive for the E6 16-40 (SEQ ID NO: 36) region were positive for the E6 26-40 (SEQ ID NO: 47) 15-mer peptide and eight of eight T cell clones were also positive with E6-vac infected autologous LCL (FIG. 14D). For the E6 31-55 (SEQ ID NO: 37) region, all four (#105-20, #115-20, #127-20, #138-20) of positive CD8 T cell clones were positive for the E6 31-45 (SEQ ID NO: 123) 15-mer peptide and six of eight positive clones were positive with E6-vac infected autologous LCL (FIG. 14E). For subject 5, none of 5 T cell clones positive for the E6 28-40 (SEQ ID NO: 47) region was positive upon retesting with the three 15-mer peptides or with E6-vac infected autologous LCL. Two (clones #1-5 and #17-5) of ten T cell clones positive for the E6 121-145 (SEQ ID NO: 43) region were positive with the E6 141-155 (SEQ ID NO: 185; 15-mer) peptide but not with E6-vac infected autologous LCL. Hence, it was concluded that this epitope was not naturally processed.

Figure 15A:
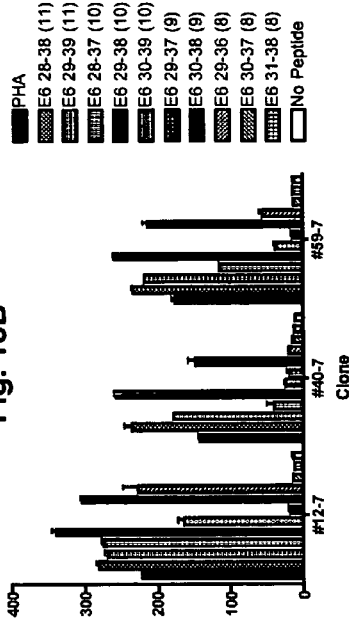
FIGS. 15A-D show results of the ELISPOT assay demonstrating that the shortest and optimal peptide for subject 7's dominant epitope was E6 29-38 (SEQ ID NO: 1), and the subdominant epitope was E6 52-61 (SEQ ID NO: 16). The numbers in parentheses indicate peptide length in amino acids.
Figure 15B:
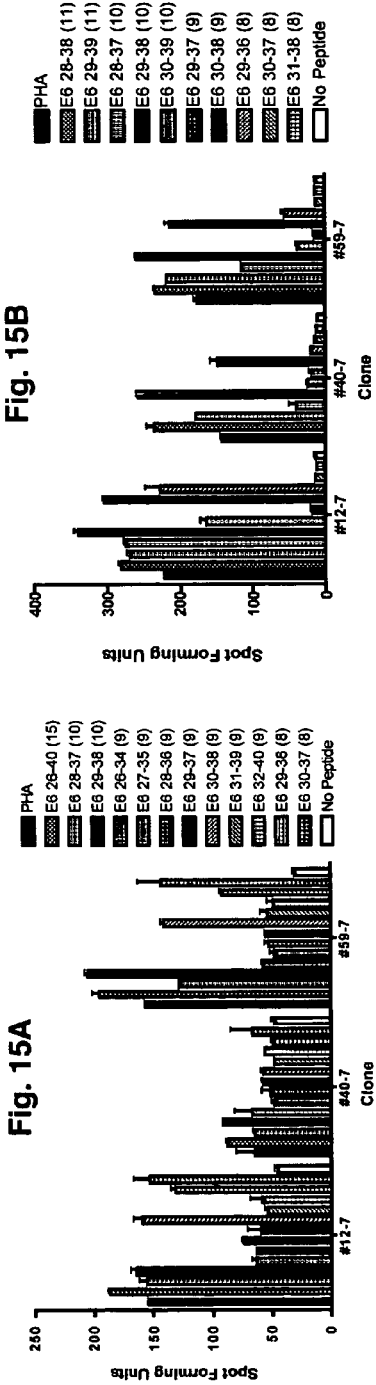
Figure 15D:
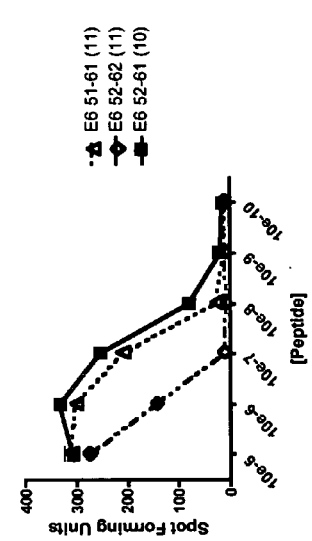
Figure 15C:
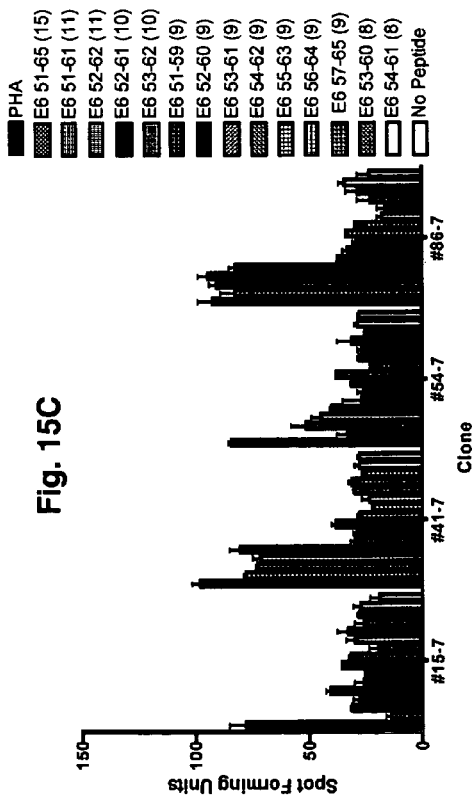

To characterize subject 7's dominant epitope within the E6 26-40 (SEQ ID NO: 47) region, seven 9-mers, two 8-mers, two 10-mers were tested (FIG. 15A). Of the 9-mers, only the E6 30-38 (SEQ ID NO: 51) peptide was positive for clones #12-7 and #59-7. None of the 9-mers were positive for clone #40-7. However, more spot forming units were detected for the E6 29-38 (SEQ ID NO: 1) 10-mer peptide for all three clones. This was demonstrated again in an ELISPOT assay which included two 11-mers (FIG. 14B). Therefore, the minimal and optimal epitope appeared to be the E6 29-38 (SEQ ID NO: 1) 10-mer peptide. The subdominant epitope from subject 7 was also characterized. In addition to seven 9-mers, two 8-mers, two 10-mers, and two 11-mers were examined (FIG. 14C). None of the 9-mers was positive, and E6 52-61 (SEQ ID NO: 16) had the most number of spot forming units for clones #15-7 and #41-07. For clones #54-07 and #86-07, more number of spot forming units were demonstrated with the E6 51-61 (SEQ ID NO: 104) 11-mer peptide. The dilutional analysis of the peptides had shown that the E6 52-61 (SEQ ID NO: 16) a 10-mer peptide and the E6 51-61 (SEQ ID NO: 104) an 11-mer peptide had similar patterns while the affinity of the E6 52-62 (SEQ ID NO: 103) peptide did not appear to be as high at lower peptide concentrations (#41-7 and #86-7). The representative results for clone #86-7 is shown in FIG. 14D. Therefore, the minimal and optimal peptide for subject 7's subdominant epitope was E6 52-61 (SEQ ID NO: 16), a 10-mer.

For subject 15, seven clones (#15-15, #27-15, #29-15, #34-15, #37-15, #68-15, #77-15) were tested using seven 9-mer peptides (FIG. 16A). AU clones were most strongly positive with E6 29-37 (SEQ ID NO: 15) among the 9-mar peptides. To define the shortest and optimal sequence of this epitope, two 8-mar peptides within E6 29-37 and two 10-mer peptides surrounding E6 29-37 (SEQ ID NO: 15) were tested (#15-15, #29-15, #34-15, #37-15; FIG. 16B). The response to E6 29-37 (SEQ ID NO: 715), a 9-mer was stronger in all clones tested compared to either 8-mer. However, the difference between E6 30-37 (SEQ ID NO: 55) an 8-mer and E6 29-37 (SEQ ID NO: 15) a 9-mer was >100 spot-forming units only for clone #37-15. The responses to E6 26-40 (SEQ ID NO: 47) a 15-mer, E6 29-38 (SEQ ID NO: 1) a10-mer, E6 28-37 (SEC) ID NO: 54) a 10-mer, and E6 29-37 (SEQ ID NO: Ng, 15) a 9-mer were similar. To clarify whether the E6 30-37 (SEQ ID NO: 55) or the E6 29-37 (SEQ ID NO: 15) was the optimal peptide, these two peptides and the E6 29-36 (SEQ ID NO: 56) peptide were serially diluted and retested. The E6 29-37 (SEQ ID NO: 15) was positive over a wider range of dilutions compared to either one of the 8-mers for four clones tested (#15-15, #29-15, #34-15, and #37-15). A representative graph for clone #15-15 is shown in FIG. 16C. These results suggested that the shortest and optimal peptide was E6 29-37 (SEQ ID NO: 15).

Figure 17A:
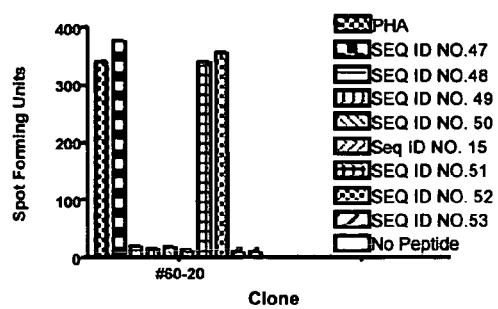
FIGS. 17A-E show ELISPOT assays demonstrating that the shortest and optimal peptide for subject 20's dominant epitope present within the overlapping amino acids in the E6 26-40 (SEQ ID NO: 47) and E6 31-45 (SEQ ID NO: 123) regions was E6 31-38 (SEQ ID NO: 17).
Figure 17B:
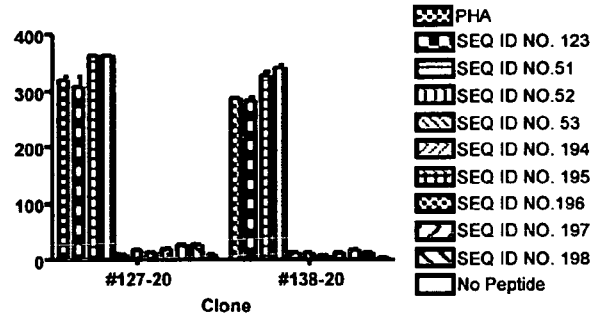
Figure 17C:
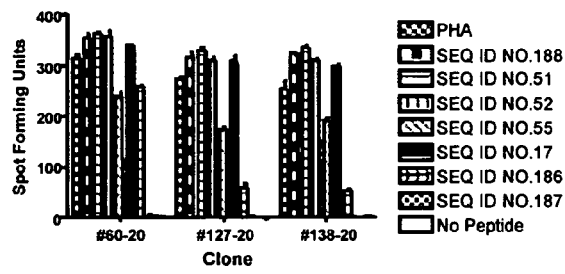
Figure 17D:
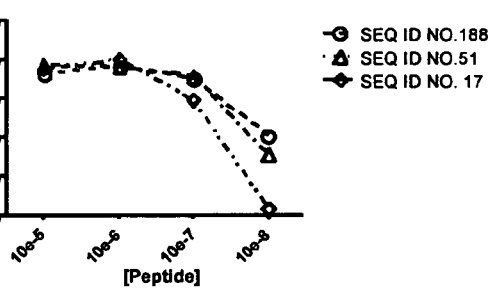
Figure 17E:
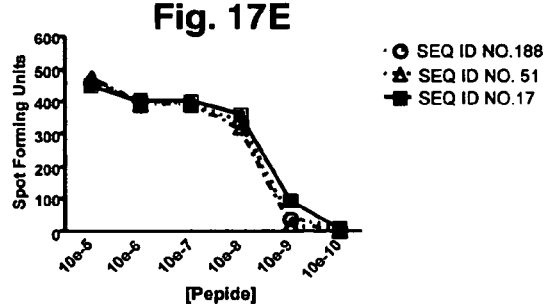

For subject 20, one clone (#60-20) positive for the E6 26-40 (SEQ ID NO: 47) region and two clones (#127-20 and #138-20) positive for the E6 31-45 (SEQ ID NO: 123) region were tested with separate sets of 9-mer peptides. All three clones (#60-20, #127-20 and #138-20) were positive for the E6 30-38 (SEQ ID NO: 51) and E6 31-39 (SEQ ID NO: 52) peptides (FIG. 17A, 17B). Therefore, a single epitope appeared to be present in an area of overlap of the E6 26-40 (SEQ ID NO: 47) and E6 31-45 (SEQ ID NO: 123) regions. The three clones were also tested with two 7-mers, two 8-mers, two 9-mers, and one 10-mer (FIG. 17C). Less number of spot forming units were seen with E6 31-37 (SEQ ID NO: 186) 7-mer, E6 32-38 (SEC) ID NO: 187) 7-mer, and E6 30-37 (SEQ ID NO: 55) 8-mer, but those with E6 31-38 (SEQ ID NO: 17) 8-mer, E6 30-38 (SEQ ID NO: 51) 9-mer, E6 31-39 (SEQ ID NO: 52) 9-mer, and E6 30-39 (SEQ ID NO: 188) 10-mer were similar. Serial dilutions of the peptides were performed to compare E6 30-39 (SEQ ID NO: 188) 10-mer, E6 30-38 (SEQ ID NO: 9-mer, and E6 31-39 (SEQ ID NO: 52) 9-mer for clone #138-20 (FIG. 17D), and to compare E6 30-39 (SEQ ID NO: 188) 10-mer, E6 30-38 (SEQ ID NO. 51) 9-mer, and E6 31-38 (SEQ ID NO. 17) 8-mer for clones #60-20 and #138-20 (FIG. 17E). The E6 30-38 (SEQ ID NO. 51) 9-mer peptide had better affinity compared to E6 31-39 (SEQ ID NO: 52) 9-mer (FIG. 17D). The affinity of E6 31-38 (SEQ ID NO: 17; 8-mer), E6 30-38 (SEQ ID NO: 51; 9-mer), and E6 30-39 (SEQ ID NO: 188; 10-mer) appeared to be similar (FIG. 17E). Therefore, the minimal and optimal amino acid sequence was the E6 31-38 (SEC) ID NO: 17) 8-mer peptide for subject 20's dominant epitope.

The two T cell clones (#1-5 and #17-5) from subject 5, which were positive with the E6 141-155 (SEQ ID NO: 185) 15-mer peptide were tested with seven overlapping 9-mers within this peptide along with three 11-mers (E6 142-152 (SEQ ID NO: 189), E6 143-153 (SEQ ID NO: 190), and E6 144-154 (SEQ ID NO: 191). None of the 9-mers and the 11-mers was positive by ELISPOT assay although the positivity to the E6 141-155 (SEQ ID NO: 185) peptide was confirmed by ELISPOT assay with both clones. This epitope was not characterized any further since it did not appear to be naturally processed.

Further, allogeneic LCLs sharing one or a few HLA class I molecules with each subject were used to determine the restriction element using ELISPOT assays. None of the allogeneic LCLs were positive for the E6 29-38 (SEQ ID NO: 1) epitope (#12-7, #40-7, #45-7, and #59-7); an HLA-B35 matched allogeneic LCL was positive for the E6 52-61 (SEQ ID NO: 16) epitope (#15-7, #41-7, #54-7, and #86-7); an HLA-B48 matched allogeneic LCL was positive for the E6 29-37 (SEQ ID NO: 15) epitope (#15-15, #27-15, #29-15, #34-15, and #37-15); and an HLA-B4002 matched allogeneic LCL was positive for the E6 31-38 (SEQ ID NO: 17) epitope (#60-20 and #138-20).

Figure 18A:
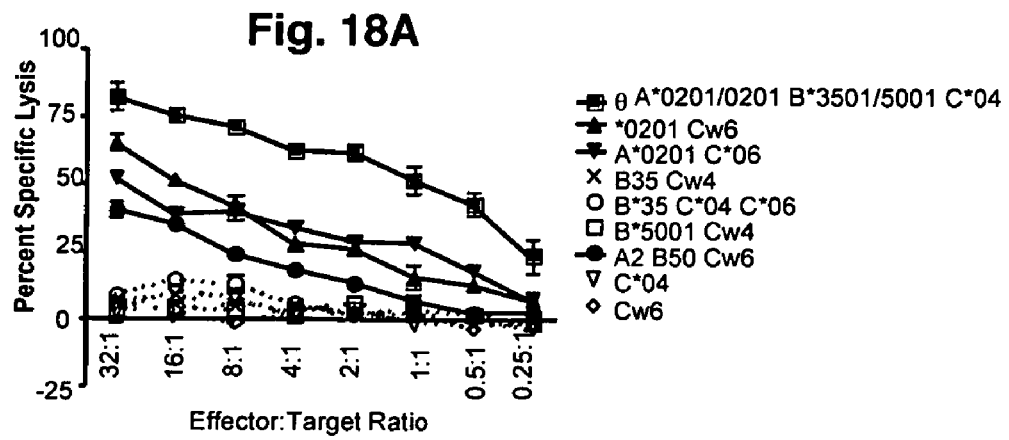
Figure 18B:
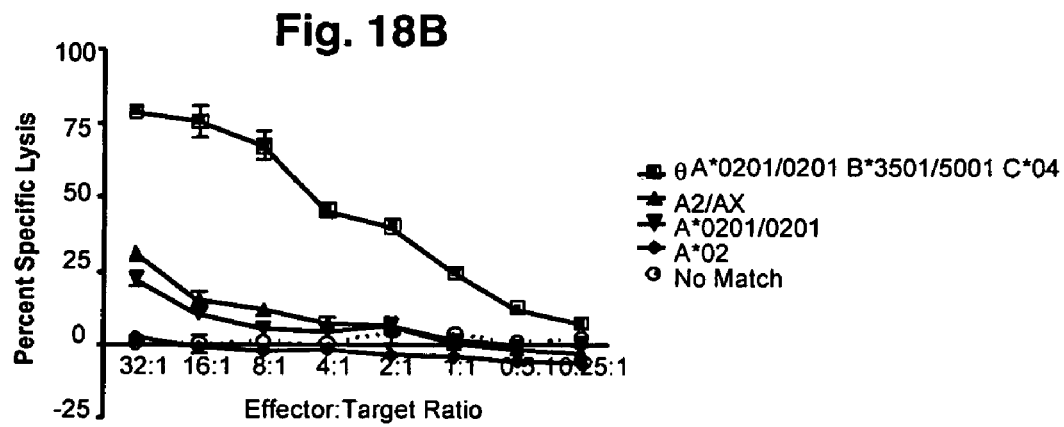
Figure 18C:
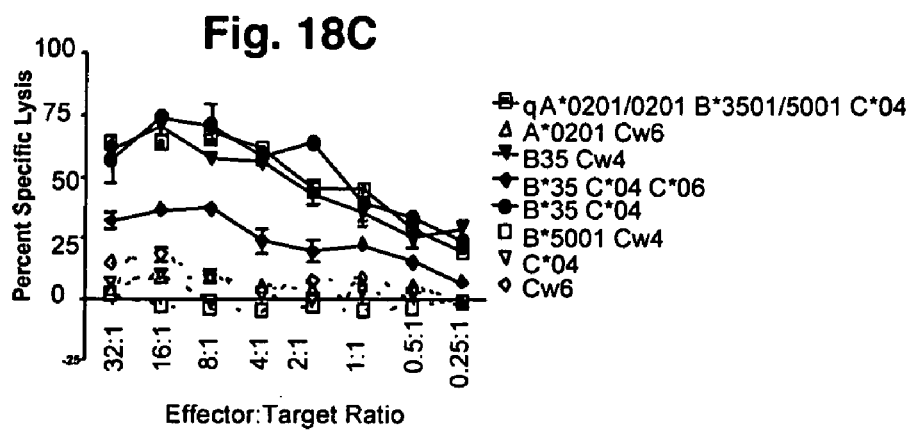

For subject 7's E6 29-38 (SEQ ID NO: 1) epitope, HLA-A0201 matched heterozygous LCLs demonstrated cytotoxicity but less than that the A0201 homozygous autologous LCL (clones #40-7 and #59-7; FIG. 18A). The different levels of cytotoxicity appeared to be related only partially to zygosity of the restriction element since allogeneic LCLs homozygous for HLA-A0201 were lysed at lesser levels compared to the autologous LCL (clones #40-7 and #59-7; FIG. 18B). For subject 7's E6 52-61 (SEQ ID NO: 16) epitope, the chromium release showed cytotoxicity with three HLA-B35 matched allogeneic LCLs (clones #41-7 and #86-7), but the level of lysis was lower for one of the allogeneic LCL compared to other LCLs and the autologous LCL (FIG. 18C). It was possible that this allogeneic LCL expressed a different allele of B35 compared to autologous LCL. Similarly, chromium release assay confirmed that HLA-048 was the restriction molecule for the E6 29-37 (SEQ ID NO: 15) epitope (#34-15 and #37-15; FIG. 18D), and that HLA-B4002 was the restriction molecule for the E6 31-38 (SEQ ID NO: 17) epitope (#60-20, #127-20, and #138-20; FIG. 18E). The clones #34-15 and #37-15 specific for the E6 29-37 (SEQ ID NO: 15) epitope were also tested with another B48-restricted HPV epitope (E7 7-15; SEQ ID NO: 18) using autologous LCL and two allogeneic LCL expressing B48. No cytotoxicity was observed underscoring the specificity of the T-cell clones. The CD8 T cell epitopes described herein are summarized in Table 8.

TABLE 8

Summary of the HPV 16 E6 CD8 T cell epitopes described on the basis of strong T cell response.

| Epitope | # of amino acids | SEQ ID No. | Naturally processed | Kills target | Binding motif | HLA molecule |
|---------|------------------|------------|---------------------|--------------|---------------|--------------|
| E6 29-37 | 9  | 15 | Yes | Yes | No  | B48   |
| E6 29-38 | 10 | 1  | Yes | Yes | No  | A0201 |
| E6 31-38 | 8  | 17 | Yes | Yes | No  | B4002 |
| E6 52-61 | 10 | 16 | Yes | Yes | Yes | B57   |
| E6 52-61 | 10 | 16 | Yes | Yes | Yes | B35   |

Furthermore, the surface phenotypes of all but one T cell clones were CD3+CD4−CD8+CD16− (#12-7, #17-7, #25-7, #38-7, #40-7, #45-7, #59-7, #62-7, #65-7, #83-7, #3-7, #15-7, #20-7, #41-7, #54-7, #86-7, #15-15, #29-15, #34-15, #37-15, #6-20, #60-20, #89-20, #105-20, #115-20, #127-20, #138-20, and #165-20). Clone #27-15 consisted of a mixed population of T cells with CD4+ subset and CD8+ subset.

The following references were cited herein:

Alexander, M. et al. (1996) *Am J Obstet Gynecol* 175: 1586-1593.
Beaudenon, S. et al. (1986) *Nature* 321(6067); 246-249.
Bontkes, H. J. et al. (1997) *Br J Cancer* 76(10): 1353-1360.
Bourgault Villada I et al. (2000) *Eur J Immunol* 30 (8): 2281-2282.
Campion, M. J. et al. (1986) *Lancet* 2: 236-240.
Chen, L. P. et al (1991) *Proc Natl Acad Sci USA* 88(1): 110-114.
Chen, L. P. et al (1992) *J immunol* 148(8): 2617-2621.
Crook, T. et al. (1991) *Cell* 67(3): 547-556.
Crum, C. P. et al. (1985) *J Virol* 54(3); 675-681.
Evans, E. M. et al. (1997) *Cancer Res* 57: 2943-2950.
Evans, C. et al. (1996) *Cancer Immunol Immunother* 42(3): 151-160.
Ferrara, A. et al (2003) *J Cancer Res Clin Oncol* 129(9); 521-530.
Feltkamp, M. C. et al. (1993) *Eur J Immunol* 23: 2242-9.
Feltkamp, M. C. et al. (1995) *Eur J Immunol* 25: 2638-2642.
Fong, L. et al. (2001) *Proc Natl Acad Sci USA* 98(15):8809-8814.
Fuchs, P. G. et al. (1988) *Int J Cancer* 41(1) 41-45.
Gao, Q et al. (1999) *Mol Cell Biol* 19: 733-744.
Garcia, A. M. et al (1999) *Immunol Lett* 67(3): 167-177.
Greenberg, P. D. et al. (1991) *Adv Immunol* 49: 281-355.
Heck, D. V. et al (1992) *Proc Natl Acad Sci USA* 89(10): 4442-4446.
Hohn, H. et al. (1999) *J Immunol* 163(10): 5715-5722.
Kast, W. M. et al. (1999) *J Immunol* 152: 3904-3912.
Kast, W. M. et al. (1993) *J Immunother* 14 (2): 115-120.
Kast, W. M. et al. (1994) *J Immunol* 152: 3904-3912.
Kaul, R. et al. (2001) *J Clin Invest* 107: 1303-1310.
Kaul, R. and Rowland-Jones, S. L. (2000) Methods of Detection of HPV-specific CTL and their role in protecting against HIV infection, p35-44. In B. Korber, et al. (ed), *HIV molecular immunology* 2000. Los Alamos National Laboratory, Los Alamos, N. M.
Klingelhutz, A. J. et al. (1996) *Nature* 380: 79-82.
Koutsky, L. A. et al. (1992) *N Engl J Med* 327(18): 1272-1278.
Kuhne, C. et al. (1998) *J Biol Chem* 273: 34301-34309.
Kukimoto et al. (1998) *Biochem Biophys Res Comm* 249: 258-262.
Larsson, M. et al. (2002) *AIDS* 16: 171-180.
Lehtinen et al. (1995) *Biochem Biophys Res Comm* 209(2): 541-546.
Lorincz, A. T. et al. (1986) *J Virol* 58:225-229.
Lorincz, A. T. et al. (1987) *Virol* 159:187-190.
Marsh et al. (2000) The HLA Facts book, San Diego, San Francisco, New York, Boston, London, Sydney, Tokyo: Academic Press.
Munoz, N. et al. (2003) *N Engl J Med* 348(6); 518-527.
Moscicki A. B. et al. (1998) *J Pediatr* 132: 277-284.
Nakagawa, M. et al. (1999) *Clin Diag Lab Immunol* 6(4): 494-498.
Nakagawa, M. et al. (2002) *Clin Diag Lab Immunol* 9(4): 877-882.
Nakagawa, M. et al. (1997) *J Infect Dis* 175:927-931.
Nakagawa, M. et al. (2000) *J Infect Dis* 182: 595-598.
Nakagawa, M. et al. (2004) *Clin Diag Lab Immunol* 11: 889-896.
Nash, J. D. et al. (1987) *Obstet Gynecol* 69: 160-162.
Oerke, S. et al. (2005) *Int J Cancer* 114: 766-778
Parkin, D. et al. (1999) *Intl J Cancer* 80: 827-841.
Patel, D. et al. (1999) *EMBO J* 18: 5061-5072.
Pim, D. et al. (1997) *Oncogene* 15: 257-264.
Pirisi, L. et al. (1987) *J Virol* 61: 1061-1066.
Reid, R. et al. (1987) *Obstet Gynecol Clin North Am* 14(2): 407-429.
Ressing, M. E. et al. (1995) *J Immunol* 154: 5934-5943.
Richart, R. M. et al. (1969) *Am J Obstet Gynecol* 105: 383-393.
Rickinson and Moss (1997) *Ann Rev Immunol* 15: 405-431.
Ridgway, D. et al. (2003) *Cancer Invest* 21(6): 873-886.
Ronco, L. V. et al. (1998) *Genes Dev* 12: 2061-2072.
Sadovnikova, E. et al. (1994) *Int Immunol* 6: 289-296.
Santin, A. D. et al. (1999) *J Virol* 73(7): 5402-5410.
Santin, A. D. et al. (2002) *N Engl J Med* 346(22): 1752-1753.
Sarkar, A. K. et al. (1995) *Viral Immunol* 8: 165-74.
Scheffner, M. et al. (1990) *Cell* 63(6): 1129-1136.
Schlegel, R. et al (1988) *EMBO J* 7(10): 3181-3187.
Seedorf K. et al. (1985) *Virology* 145:181-185.
Silverberg and Lubera (1988) *Cancer Journal for Clinicians* 38; 5-22.
Storey, A. et al. (1988) *EMBO J* 7(6): 1815-1820.
Strang, G. et al. (1990) *J Gen Virol* 71(PT 2): 423-431.
Tarpey, I et al. (1994) *Immunology* 81(2):222-227.
Ting Y. et al., (1990) Detection and typing of genital human papillomaviruses. San Diego: Academic Press, 1990 (Innis M. A. et al. ed. PCR Protocols and Applications).
Werness, B. A. et al. (1990) *Science* 248: 76-79.
Wheeler, C. M. et al. (1997) *J Clin Microbiol* 35(1): 11-19.
World Health Organization (1990) Global Estimates for Health Situation Assessment and Projections 29-30.
Yoon, H et al. (1988) *Virus Res* 54(1): 23-29.
Youde, S. J. et al. (2000) *Cancer Res* 60 (2): 365-371.
Youde, S. J. et al. (2005) *Int J Cancer* 114: 606-612.
Zimmermann, H. et al. (1999) *J Virol* 73:6209-6219.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A set of isolated peptides derived from E6 and E7 proteins of HPV type 16 comprising overlapping E6 peptides consisting of the sequences shown in SEQ ID NO: 45 (E6 16-30), SEQ ID NO: 46 (E6 21-35), SEQ ID NO: 48 (E6 26-34), SEQ ID NO: 47 (E6 26-40), SEQ ID NO: 49 (E6 27-35), SEQ ID NO: 50 (E6 28-36), SEQ ID NO: 15 (E6 29-37), SEQ ID NO: 1 (E6 29-38), SEQ ID NO: (E6 29-61), SEQ ID NO: 51 (E6 30-38), SEQ ID NO: 17 (E6 31-38), SEQ ID NO: 52 (E6 31-39), SEQ ID NO: 53 (E6 32-40), SEQ ID NO: 104 (E6 51-61), SEQ ID NO: 90 (E6 51-65), SEQ ID NO: 98 (E6 53-61), SEQ ID NO: 105 (E6 53-62), and SEQ ID NO: 107 (E6 54-61) and overlapping E7 peptides consisting of the sequences shown in SEQ ID NO: 18 (E7 7-15), SEQ ID NO: 21 (E7 7-20), SEQ ID NO: 57 (E7 11-19), SEQ ID NO: 3 (E7 11-20), SEQ ID NO: 58 (E7 12-20), SEQ ID NO: 83 (E7 76-84), SEQ ID NO: 84 (E7 77-85), SEQ ID NO: 85 (E7 78-86), SEQ ID NO: 80 (E7 76-90), SEQ ID NO: 19 (E7 79-87), SEQ ID NO: 86 (E7 80-88), SEQ ID NO: 87 (E7 81-89), SEQ ID NO: 5 (E7 82-90), and SEQ ID NO: 6 (E7 86-93).

2. An isolated peptide selected from the group consisting of SEQ ID NO: 20 (E6 29-61), SEQ ID NO: 17 (E6 31-38), and SEQ ID NO: 21 (E7 7-20).

3. An immunogenic composition comprising a peptide identified in claim 2 and an adjuvant.

4. The composition of claim 3, wherein said peptide is expressed from a recombinant viral vector or a plasmid.

* * * * *

SEQUENCE LISTING

<160> NUMBER OF SEQ ID NOS: 198

<210> SEQ ID NO 1
<211> LENGTH: 10
<212> TYPE: PRT
<213> ORGANISM: Human Papilloma Virus 16
<220> FEATURE:
<221> NAME/KEY: CHAIN
<223> OTHER INFORMATION: residues 29-38 of the E6 protein

<400> SEQUENCE: 1

Thr Ile His Asp Ile Ile Leu Glu Cys Val
                5                   10

<210> SEQ ID NO 2
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 80-88 of the E6 protein

<400> SEQUENCE: 2

Ile Ser Glu Tyr Arg His Tyr Cys Tyr
                5

<210> SEQ ID NO 3
<211> LENGTH: 10
<212> TYPE: PRT
<213> ORGANISM: Human Papilloma Virus 16
<220> FEATURE:
<221> NAME/KEY: CHAIN
<223> OTHER INFORMATION: residues 11-20 of the E7 protein

<400> SEQUENCE: 3

Tyr Met Leu Asp Leu Gln Pro Glu Thr Thr
                5                   10

<210> SEQ ID NO 4
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 44-52 of the E7 protein

<400> SEQUENCE: 4

Gln Ala Glu Pro Asp Arg Ala His Tyr
                5

<210> SEQ ID NO 5
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 82-90 of the E7 protein

<400> SEQUENCE: 5

Leu Leu Met Gly Thr Leu Gly Ile Val
                5

<210> SEQ ID NO 6
<211> LENGTH: 8
<212> TYPE: PRT
<213> ORGANISM: Human Papilloma Virus 16
<220> FEATURE:

```
<221> NAME/KEY: CHAIN
<223> OTHER INFORMATION: residues 86-93 of the E7 protein

<400> SEQUENCE: 6

Thr Leu Gly Ile Val Cys Pro Ile
                5

<210> SEQ ID NO 7
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 323-331 of the L1 protein

<400> SEQUENCE: 7

Ile Cys Trp Gly Asn Gln Leu Phe Val
                5

<210> SEQ ID NO 8
<211> LENGTH: 10
<212> TYPE: PRT
<213> ORGANISM: Human Papilloma Virus 18
<220> FEATURE:
<221> NAME/KEY: CHAIN
<223> OTHER INFORMATION: residues 24-33 of the E6 protein

<400> SEQUENCE: 8

Ser Leu Gln Asp Ile Glu Ile Thr Cys Val
                5                   10

<210> SEQ ID NO 9
<211> LENGTH: 9
<212> TYPE: PRT
<213> ORGANISM: Human Papilloma Virus 18
<220> FEATURE:
<221> NAME/KEY: CHAIN
<223> OTHER INFORMATION: residues 25-33 of the E6 protein

<400> SEQUENCE: 9

Leu Gln Asp Ile Glu Ile Thr Cys Val
                5

<210> SEQ ID NO 10
<211> LENGTH: 9
<212> TYPE: PRT
<213> ORGANISM: Human Papilloma Virus 18
<220> FEATURE:
<221> NAME/KEY: CHAIN
<223> OTHER INFORMATION: residues 40-48 of the E6 protein

<400> SEQUENCE: 10

Glu Leu Thr Glu Val Phe Glu Phe Ala
                5

<210> SEQ ID NO 11
<211> LENGTH: 9
<212> TYPE: PRT
<213> ORGANISM: Human Papilloma Virus 18
<220> FEATURE:
<221> NAME/KEY: CHAIN
<223> OTHER INFORMATION: residues 47-55 of the E6 protein

<400> SEQUENCE: 11

Phe Ala Phe Lys Asp Leu Phe Val Val
                5

<210> SEQ ID NO 12
```

```
<211> LENGTH: 10
<212> TYPE: PRT
<213> ORGANISM: Human Papilloma Virus 18
<220> FEATURE:
<221> NAME/KEY: CHAIN
<223> OTHER INFORMATION: residues 92-101 of the E6 protein

<400> SEQUENCE: 12

Lys Leu Thr Asn Thr Gly Leu Tyr Asn Leu
                5                   10

<210> SEQ ID NO 13
<211> LENGTH: 9
<212> TYPE: PRT
<213> ORGANISM: Human Papilloma Virus 18
<220> FEATURE:
<221> NAME/KEY: CHAIN
<223> OTHER INFORMATION: residues 13-21 of the E6 protein

<400> SEQUENCE: 13

Lys Leu Pro Asp Leu Cys Thr Glu Leu
                5

<210> SEQ ID NO 14
<211> LENGTH: 9
<212> TYPE: PRT
<213> ORGANISM: Human Papilloma Virus 18
<220> FEATURE:
<221> NAME/KEY: CHAIN
<223> OTHER INFORMATION: residues 54-62 of the L1 protein

<400> SEQUENCE: 14

Asn Val Phe Pro Ile Phe Leu Gln Met
                5

<210> SEQ ID NO 15
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 29-37 of the E6 protein

<400> SEQUENCE: 15

Thr Ile His Asp Ile Ile Leu Glu Cys
                5

<210> SEQ ID NO 16
<211> LENGTH: 10
<212> TYPE: PRT
<213> ORGANISM: Human Papilloma Virus 16
<220> FEATURE:
<221> NAME/KEY: CHAIN
<223> OTHER INFORMATION: residues 52-61 of the E6 protein

<400> SEQUENCE: 16

Phe Ala Phe Arg Asp Leu Cys Ile Val Tyr
                5                   10

<210> SEQ ID NO 17
<211> LENGTH: 8
<212> TYPE: PRT
<213> ORGANISM: Human Papilloma Virus 16
<220> FEATURE:
<221> NAME/KEY: CHAIN
<223> OTHER INFORMATION: residues 31-38 of the E6 protein

<400> SEQUENCE: 17

His Asp Ile Ile Leu Glu Cys Val
```

```
                              5

<210> SEQ ID NO 18
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 7-15 of the E7 protein

<400> SEQUENCE: 18

Thr Leu His Glu Tyr Met Leu Asp Leu
                  5

<210> SEQ ID NO 19
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 79-87 of the E7 protein

<400> SEQUENCE: 19

Leu Glu Asp Leu Leu Met Gly Thr Leu
                  5

<210> SEQ ID NO 20
<211> LENGTH: 33
<212> TYPE: PRT
<213> ORGANISM: Human Papilloma Virus 16
<220> FEATURE:
<221> NAME/KEY: CHAIN
<223> OTHER INFORMATION: residues 29-61 of the E6 protein

<400> SEQUENCE: 20

Thr Ile His Asp Ile Ile Leu Glu Cys Val Tyr Cys Lys Gln Gln
                  5                  10                  15

Leu Leu Arg Arg Glu Val Tyr Asp Phe Ala Phe Arg Asp Leu Cys
              20                  25                  30

Ile Val Tyr

<210> SEQ ID NO 21
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 7-20 of the E7 protein

<400> SEQUENCE: 21

Thr Leu His Glu Tyr Met Leu Asp Leu Gln Pro Glu Thr Thr
                  5                  10

<210> SEQ ID NO 22
<211> LENGTH: 10
<212> TYPE: PRT
<213> ORGANISM: Human Papilloma Virus 18
<220> FEATURE:
<221> NAME/KEY: CHAIN
<223> OTHER INFORMATION: residues 47-56

<400> SEQUENCE: 22

Phe Ala Phe Lys Asp Leu Phe Val Val Tyr
                  5                  10

<210> SEQ ID NO 23
<211> LENGTH: 10
```

```
<212> TYPE: PRT
<213> ORGANISM: Human Papilloma Virus 31
<220> FEATURE:
<221> NAME/KEY: CHAIN
<223> OTHER INFORMATION: residues 45-54

<400> SEQUENCE: 23

Phe Ala Phe Thr Asp Leu Thr Ile Val Tyr
                5                   10

<210> SEQ ID NO 24
<211> LENGTH: 10
<212> TYPE: PRT
<213> ORGANISM: Human Papilloma Virus 33
<220> FEATURE:
<221> NAME/KEY: CHAIN
<223> OTHER INFORMATION: residues 45-54

<400> SEQUENCE: 24

Phe Ala Phe Ala Asp Leu Thr Val Val Tyr
                5                   10

<210> SEQ ID NO 25
<211> LENGTH: 10
<212> TYPE: PRT
<213> ORGANISM: Human Papilloma Virus 35
<220> FEATURE:
<221> NAME/KEY: CHAIN
<223> OTHER INFORMATION: residues 45-54

<400> SEQUENCE: 25

Phe Ala Cys Tyr Asp Leu Cys Ile Val Tyr
                5                   10

<210> SEQ ID NO 26
<211> LENGTH: 10
<212> TYPE: PRT
<213> ORGANISM: Human Papilloma Virus 39
<220> FEATURE:
<221> NAME/KEY: CHAIN
<223> OTHER INFORMATION: residues 47-56

<400> SEQUENCE: 26

Phe Ala Phe Ser Asp Leu Tyr Val Val Tyr
                5                   10

<210> SEQ ID NO 27
<211> LENGTH: 10
<212> TYPE: PRT
<213> ORGANISM: Human Papilloma Virus 45
<220> FEATURE:
<221> NAME/KEY: CHAIN
<223> OTHER INFORMATION: residues 47-56

<400> SEQUENCE: 27

Phe Ala Phe Ser Asp Leu Tyr Val Val Tyr
                5                   10

<210> SEQ ID NO 28
<211> LENGTH: 10
<212> TYPE: PRT
<213> ORGANISM: Human Papilloma Virus 51
<220> FEATURE:
<221> NAME/KEY: CHAIN
<223> OTHER INFORMATION: residues 45-54

<400> SEQUENCE: 28

Val Ala Phe Thr Glu Ile Lys Ile Val Tyr
                5                   10
```

<210> SEQ ID NO 29
<211> LENGTH: 10
<212> TYPE: PRT
<213> ORGANISM: Human Papilloma Virus 52
<220> FEATURE:
<221> NAME/KEY: CHAIN
<223> OTHER INFORMATION: residues 45-54

<400> SEQUENCE: 29

Phe Leu Phe Thr Asp Leu Arg Ile Val Tyr
                5                   10

<210> SEQ ID NO 30
<211> LENGTH: 10
<212> TYPE: PRT
<213> ORGANISM: Human Papilloma Virus 56
<220> FEATURE:
<221> NAME/KEY: CHAIN
<223> OTHER INFORMATION: residues 48-57

<400> SEQUENCE: 30

Phe Ala Cys Thr Glu Leu Lys Leu Val Tyr
                5                   10

<210> SEQ ID NO 31
<211> LENGTH: 10
<212> TYPE: PRT
<213> ORGANISM: Human Papilloma Virus 58
<220> FEATURE:
<221> NAME/KEY: CHAIN
<223> OTHER INFORMATION: residues 45-54

<400> SEQUENCE: 31

Phe Val Phe Ala Asp Leu Arg Ile Val Tyr
                5                   10

<210> SEQ ID NO 32
<211> LENGTH: 10
<212> TYPE: PRT
<213> ORGANISM: Human Papilloma Virus 59
<220> FEATURE:
<221> NAME/KEY: CHAIN
<223> OTHER INFORMATION: residues 47-56

<400> SEQUENCE: 32

Phe Ala Phe Gln Asp Leu Phe Ile Val Tyr
                5                   10

<210> SEQ ID NO 33
<211> LENGTH: 10
<212> TYPE: PRT
<213> ORGANISM: Human Papilloma Virus 68
<220> FEATURE:
<221> NAME/KEY: CHAIN
<223> OTHER INFORMATION: residues 47-56

<400> SEQUENCE: 33

Phe Ala Phe Gly Asp Leu Gln Val Val Tyr
                5                   10

<210> SEQ ID NO 34
<211> LENGTH: 10
<212> TYPE: PRT
<213> ORGANISM: Human Papilloma Virus 73
<220> FEATURE:
<221> NAME/KEY: CHAIN
<223> OTHER INFORMATION: residues 45-54

```
<400> SEQUENCE: 34

Phe Ala Phe Ser Asp Leu Cys Ile Val Tyr
                 5                  10

<210> SEQ ID NO 35
<211> LENGTH: 25
<212> TYPE: PRT
<213> ORGANISM: Human Papilloma Virus 16
<220> FEATURE:
<221> NAME/KEY: CHAIN
<223> OTHER INFORMATION: residues 1-25 of the E6 protein

<400> SEQUENCE: 35

Met His Gln Lys Arg Thr Ala Met Phe Gln Asp Pro Gln Glu Arg
                 5                  10                  15

Pro Arg Lys Leu Pro Gln Leu Cys Thr Glu
             20                  25

<210> SEQ ID NO 36
<211> LENGTH: 25
<212> TYPE: PRT
<213> ORGANISM: Human Papilloma Virus 16
<220> FEATURE:
<221> NAME/KEY: CHAIN
<223> OTHER INFORMATION: residues 16-40 of the E6 protein

<400> SEQUENCE: 36

Pro Arg Lys Leu Pro Gln Leu Cys Thr Glu Leu Gln Thr Thr Ile
                 5                  10                  15

His Asp Ile Ile Leu Glu Cys Val Tyr Cys
             20                  25

<210> SEQ ID NO 37
<211> LENGTH: 25
<212> TYPE: PRT
<213> ORGANISM: Human Papilloma Virus 16
<220> FEATURE:
<221> NAME/KEY: CHAIN
<223> OTHER INFORMATION: residues 31-55 of the E6 protein

<400> SEQUENCE: 37

His Asp Ile Ile Leu Glu Cys Val Tyr Cys Lys Gln Gln Leu Leu
                 5                  10                  15

Arg Arg Glu Val Tyr Asp Phe Ala Phe Arg
             20                  25

<210> SEQ ID NO 38
<211> LENGTH: 25
<212> TYPE: PRT
<213> ORGANISM: Human Papilloma Virus 16
<220> FEATURE:
<221> NAME/KEY: CHAIN
<223> OTHER INFORMATION: residues 46-70 of the E6 protein

<400> SEQUENCE: 38

Arg Arg Glu Val Tyr Asp Phe Ala Phe Arg Asp Leu Cys Ile Val
                 5                  10                  15

Tyr Arg Asp Gly Asn Pro Tyr Ala Val Cys
             20                  25

<210> SEQ ID NO 39
<211> LENGTH: 25
<212> TYPE: PRT
<213> ORGANISM: Human Papilloma Virus 16
<220> FEATURE:
<221> NAME/KEY: CHAIN
```

-continued

```
<223> OTHER INFORMATION: residues 61-85 of the E6 protein

<400> SEQUENCE: 39

Tyr Arg Asp Gly Asn Pro Tyr Ala Val Cys Asp Lys Cys Leu Lys
 1               5                  10                  15

Phe Tyr Ser Lys Ile Ser Glu Tyr Arg His
             20                  25

<210> SEQ ID NO 40
<211> LENGTH: 25
<212> TYPE: PRT
<213> ORGANISM: Human Papilloma Virus 16
<220> FEATURE:
<221> NAME/KEY: CHAIN
<223> OTHER INFORMATION: residues 76-100 of the E6 protein

<400> SEQUENCE: 40

Phe Tyr Ser Lys Ile Ser Glu Tyr Arg His Tyr Cys Tyr Ser Leu
 1               5                  10                  15

Tyr Gly Thr Thr Leu Glu Gln Gln Tyr Asn
             20                  25

<210> SEQ ID NO 41
<211> LENGTH: 25
<212> TYPE: PRT
<213> ORGANISM: Human Papilloma Virus 16
<220> FEATURE:
<221> NAME/KEY: CHAIN
<223> OTHER INFORMATION: residues 91-115 of the E6 protein

<400> SEQUENCE: 41

Tyr Gly Thr Thr Leu Glu Gln Gln Tyr Asn Lys Pro Leu Cys Asp
 1               5                  10                  15

Leu Leu Ile Arg Cys Ile Asn Cys Gln Lys
             20                  25

<210> SEQ ID NO 42
<211> LENGTH: 25
<212> TYPE: PRT
<213> ORGANISM: Human Papilloma Virus 16
<220> FEATURE:
<221> NAME/KEY: CHAIN
<223> OTHER INFORMATION: residues 106-130 of the E6 protein

<400> SEQUENCE: 42

Leu Leu Ile Arg Cys Ile Asn Cys Gln Lys Pro Leu Cys Pro Glu
 1               5                  10                  15

Glu Lys Gln Arg His Leu Asp Lys Lys Glu
             20                  25

<210> SEQ ID NO 43
<211> LENGTH: 25
<212> TYPE: PRT
<213> ORGANISM: Human Papilloma Virus 16
<220> FEATURE:
<221> NAME/KEY: CHAIN
<223> OTHER INFORMATION: residues 121-145 of the E6 protein

<400> SEQUENCE: 43

Glu Lys Gln Arg His Leu Asp Lys Lys Glu Arg Phe His Asn Ile
 1               5                  10                  15

Arg Gly Arg Trp Thr Gly Arg Cys Met Ser
             20                  25

<210> SEQ ID NO 44
```

```
<211> LENGTH: 23
<212> TYPE: PRT
<213> ORGANISM: Human Papilloma Virus 16
<220> FEATURE:
<221> NAME/KEY: CHAIN
<223> OTHER INFORMATION: residues 136-158 of the E6 protein

<400> SEQUENCE: 44

Arg Gly Arg Trp Thr Gly Arg Cys Met Ser Cys Cys Arg Ser Ser
                 5                  10                  15

Arg Tyr Arg Arg Glu Thr Gln Lys
                20

<210> SEQ ID NO 45
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 16-30 of the E6 protein

<400> SEQUENCE: 45

Pro Arg Lys Leu Pro Gln Leu Cys Thr Glu Leu Gln Thr Thr Ile
                 5                  10                  15

<210> SEQ ID NO 46
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 21-35 of the E6 protein

<400> SEQUENCE: 46

Gln Leu Cys Thr Glu Leu Glu Thr Thr Ile His Asp Ile Ile Leu
                 5                  10                  15

<210> SEQ ID NO 47
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 26-40 of the E6 protein

<400> SEQUENCE: 47

Leu Gln Thr Thr Ile His Asp Ile Ile Leu Glu Cys Val Tyr Cys
                 5                  10                  15

<210> SEQ ID NO 48
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 26-34 of the E6 protein

<400> SEQUENCE: 48

Leu Gln Thr Thr Ile His Asp Ile Ile
                 5

<210> SEQ ID NO 49
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 27-35 of the E6 protein
```

```
<400> SEQUENCE: 49

Gln Thr Thr Ile His Asp Ile Ile Leu
                5

<210> SEQ ID NO 50
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 28-36 of the E6 protein

<400> SEQUENCE: 50

Thr Thr Ile His Asp Ile Ile Leu Glu
                5

<210> SEQ ID NO 51
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 30-38 of the E6 protein

<400> SEQUENCE: 51

Ile His Asp Ile Ile Leu Glu Cys Val
                5

<210> SEQ ID NO 52
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 31-39 of the E6 protein

<400> SEQUENCE: 52

His Asp Ile Ile Leu Glu Cys Val Tyr
                5

<210> SEQ ID NO 53
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 32-40 of the E6 protein

<400> SEQUENCE: 53

Asp Ile Ile Leu Glu Cys Val Tyr Cys
                5

<210> SEQ ID NO 54
<211> LENGTH: 10
<212> TYPE: PRT
<213> ORGANISM: Human Papilloma Virus 16
<220> FEATURE:
<221> NAME/KEY: CHAIN
<223> OTHER INFORMATION: residues 28-37 of the E6 protein

<400> SEQUENCE: 54

Thr Thr Ile His Asp Ile Ile Leu Glu Cys
                5                   10

<210> SEQ ID NO 55
<211> LENGTH: 8
<212> TYPE: PRT
<213> ORGANISM: Human Papilloma Virus 16
```

```
<220> FEATURE:
<221> NAME/KEY: CHAIN
<223> OTHER INFORMATION: residues 30-37 of the E6 protein

<400> SEQUENCE: 55

Ile His Asp Ile Ile Leu Glu Cys
                5

<210> SEQ ID NO 56
<211> LENGTH: 8
<212> TYPE: PRT
<213> ORGANISM: Human Papilloma Virus 16
<220> FEATURE:
<221> NAME/KEY: CHAIN
<223> OTHER INFORMATION: residues 29-36 of the E6 protein

<400> SEQUENCE: 56

Thr Ile His Asp Ile Ile Leu Glu
                5

<210> SEQ ID NO 57
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 11-19 of the E7 protein

<400> SEQUENCE: 57

Tyr Met Leu Asp Leu Gln Pro Glu Thr
                5

<210> SEQ ID NO 58
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 12-20 of the E7 protein

<400> SEQUENCE: 58

Met Leu Asp Leu Gln Pro Glu Thr Thr
                5

<210> SEQ ID NO 59
<211> LENGTH: 25
<212> TYPE: PRT
<213> ORGANISM: Human Papilloma Virus 16
<220> FEATURE:
<221> NAME/KEY: CHAIN
<223> OTHER INFORMATION: residues 1-25 of the E7 protein

<400> SEQUENCE: 59

Met His Gly Asp Thr Pro Thr Leu His Glu Tyr Met Leu Asp Leu
                5                   10                  15
Gln Pro Glu Thr Thr Asp Leu Tyr Cys Tyr
                20                  25

<210> SEQ ID NO 60
<211> LENGTH: 25
<212> TYPE: PRT
<213> ORGANISM: Human Papilloma Virus 16
<220> FEATURE:
<221> NAME/KEY: CHAIN
<223> OTHER INFORMATION: residues 16-40 of the E7 protein

<400> SEQUENCE: 60

Gln Pro Glu Thr Thr Asp Leu Tyr Cys Tyr Glu Gln Leu Asn Asp
```

-continued

```
                5                   10                  15
Ser Ser Glu Glu Glu Asp Glu Ile Asp Gly
                20                  25

<210> SEQ ID NO 61
<211> LENGTH: 25
<212> TYPE: PRT
<213> ORGANISM: Human Papilloma Virus 16
<220> FEATURE:
<221> NAME/KEY: CHAIN
<223> OTHER INFORMATION: residues 31-55 of the E7 protein

<400> SEQUENCE: 61

Ser Ser Glu Glu Glu Asp Glu Ile Asp Gly Pro Ala Gly Gln Ala
                5                   10                  15

Glu Pro Asp Arg Ala His Tyr Asn Ile Val
                20                  25

<210> SEQ ID NO 62
<211> LENGTH: 25
<212> TYPE: PRT
<213> ORGANISM: Human Papilloma Virus 16
<220> FEATURE:
<221> NAME/KEY: CHAIN
<223> OTHER INFORMATION: residues 46-70 of the E7 protein

<400> SEQUENCE: 62

Glu Pro Asp Arg Ala His Tyr Asn Ile Val Thr Phe Cys Cys Lys
                5                   10                  15

Cys Asp Ser Thr Leu Arg Leu Cys Val Gln
                20                  25

<210> SEQ ID NO 63
<211> LENGTH: 25
<212> TYPE: PRT
<213> ORGANISM: Human Papilloma Virus 16
<220> FEATURE:
<221> NAME/KEY: CHAIN
<223> OTHER INFORMATION: residues 61-85 of the E7 protein

<400> SEQUENCE: 63

Cys Asp Ser Thr Leu Arg Leu Cys Val Gln Ser Thr His Val Asp
                5                   10                  15

Ile Arg Thr Leu Glu Asp Leu Leu Met Gly
                20                  25

<210> SEQ ID NO 64
<211> LENGTH: 23
<212> TYPE: PRT
<213> ORGANISM: Human Papilloma Virus 16
<220> FEATURE:
<221> NAME/KEY: CHAIN
<223> OTHER INFORMATION: residues 76-98 of the E7 protein

<400> SEQUENCE: 64

Ile Arg Thr Leu Glu Asp Leu Leu Met Gly Thr Leu Gly Ile Val
                5                   10                  15

Cys Pro Ile Cys Ser Gln Lys Pro
                20

<210> SEQ ID NO 65
<211> LENGTH: 15
<212> TYPE: PRT
<213> ORGANISM: Human Papilloma Virus 16
<220> FEATURE:
<221> NAME/KEY: CHAIN
```

```
<223> OTHER INFORMATION: residues 1-15 of the E7 protein

<400> SEQUENCE: 65

Met His Gly Asp Thr Pro Thr Leu His Glu Tyr Met Leu Asp Leu
                5                   10                  15

<210> SEQ ID NO 66
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 6-20 of the E7 protein

<400> SEQUENCE: 66

Pro Thr Leu His Glu Tyr Met Leu Asp Leu Gln Pro Glu Thr Thr
                5                   10                  15

<210> SEQ ID NO 67
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 11-25 of the E7 protein

<400> SEQUENCE: 67

Tyr Met Leu Asp Leu Gln Pro Glu Thr Thr Asp Leu Tyr Cys Tyr
                5                   10                  15

<210> SEQ ID NO 68
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 16-30 of the E7 protein

<400> SEQUENCE: 68

Gln Pro Glu Thr Thr Asp Leu Tyr Cys Tyr Glu Gln Leu Asn Asp
                5                   10                  15

<210> SEQ ID NO 69
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 21-35 of the E7 protein

<400> SEQUENCE: 69

Asp Leu Tyr Cys Tyr Glu Gln Leu Asn Asp Ser Ser Glu Glu Glu
                5                   10                  15

<210> SEQ ID NO 70
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 26-40 of the E7 protein

<400> SEQUENCE: 70

Glu Gln Leu Asn Asp Ser Ser Glu Glu Glu Asp Glu Ile Asp Gly
                5                   10                  15

<210> SEQ ID NO 71
<211> LENGTH: 15
```

```
<212> TYPE: PRT
<213> ORGANISM: Human Papilloma Virus 16
<220> FEATURE:
<221> NAME/KEY: CHAIN
<223> OTHER INFORMATION: residues 31-45 of the E7 protein

<400> SEQUENCE: 71

Ser Ser Glu Glu Glu Asp Glu Ile Asp Gly Pro Ala Gly Gln Ala
                 5                  10                  15

<210> SEQ ID NO 72
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 36-50 of the E7 protein

<400> SEQUENCE: 72

Asp Glu Ile Asp Gly Pro Ala Gly Gln Ala Glu Pro Asp Arg Ala
                 5                  10                  15

<210> SEQ ID NO 73
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 41-55 of the E7 protein

<400> SEQUENCE: 73

Pro Ala Gly Gln Ala Glu Pro Asp Arg Ala His Tyr Asn Ile Val
                 5                  10                  15

<210> SEQ ID NO 74
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 46-60 of the E7 protein

<400> SEQUENCE: 74

Glu Pro Asp Arg Ala His Tyr Asn Ile Val Thr Phe Cys Cys Lys
                 5                  10                  15

<210> SEQ ID NO 75
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 51-65 of the E7 protein

<400> SEQUENCE: 75

His Tyr Asn Ile Val Thr Phe Cys Cys Lys Cys Asp Ser Thr Leu
                 5                  10                  15

<210> SEQ ID NO 76
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 56-70 of the E7 protein

<400> SEQUENCE: 76

Thr Phe Cys Cys Lys Cys Asp Ser Thr Leu Arg Leu Cys Val Gln
                 5                  10                  15
```

```
<210> SEQ ID NO 77
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 61-75 of the E7 protein

<400> SEQUENCE: 77

Cys Asp Ser Thr Leu Arg Leu Cys Val Gln Ser Thr His Val Asp
                 5                  10                  15

<210> SEQ ID NO 78
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 66-80 of the E7 protein

<400> SEQUENCE: 78

Arg Leu Cys Val Gln Ser Thr His Val Asp Ile Arg Thr Leu Glu
                 5                  10                  15

<210> SEQ ID NO 79
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 71-85 of the E7 protein

<400> SEQUENCE: 79

Ser Thr His Val Asp Ile Arg Thr Leu Glu Asp Leu Leu Met Gly
                 5                  10                  15

<210> SEQ ID NO 80
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 76-90 of the E7 protein

<400> SEQUENCE: 80

Ile Arg Thr Leu Glu Asp Leu Leu Met Gly Thr Leu Gly Ile Val
                 5                  10                  15

<210> SEQ ID NO 81
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 81-95 of the E7 protein

<400> SEQUENCE: 81

Asp Leu Leu Met Gly Thr Leu Gly Ile Val Cys Pro Ile Cys Ser
                 5                  10                  15

<210> SEQ ID NO 82
<211> LENGTH: 13
<212> TYPE: PRT
<213> ORGANISM: Human Papilloma Virus 16
<220> FEATURE:
<221> NAME/KEY: CHAIN
<223> OTHER INFORMATION: residues 86-98 of the E7 protein
```

```
<400> SEQUENCE: 82

Thr Leu Gly Ile Val Cys Pro Ile Cys Ser Gln Lys Pro
                5                   10

<210> SEQ ID NO 83
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 76-84 of the E7 protein

<400> SEQUENCE: 83

Ile Arg Thr Leu Glu Asp Leu Leu Met
                5

<210> SEQ ID NO 84
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 77-85 of the E7 protein

<400> SEQUENCE: 84

Arg Thr Leu Glu Asp Leu Leu Met Gly
                5

<210> SEQ ID NO 85
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 78-86 of the E7 protein

<400> SEQUENCE: 85

Thr Leu Glu Asp Leu Leu Met Gly Thr
                5

<210> SEQ ID NO 86
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 80-88 of the E7 protein

<400> SEQUENCE: 86

Glu Asp Leu Leu Met Gly Thr Leu Gly
                5

<210> SEQ ID NO 87
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 81-89 of the E7 protein

<400> SEQUENCE: 87

Asp Leu Leu Met Gly Thr Leu Gly Ile
                5

<210> SEQ ID NO 88
<211> LENGTH: 8
<212> TYPE: PRT
<213> ORGANISM: Human Papilloma Virus 16
```

```
<220> FEATURE:
<221> NAME/KEY: CHAIN
<223> OTHER INFORMATION: residues 79-86 of the E7 protein

<400> SEQUENCE: 88

Leu Glu Asp Leu Leu Met Gly Thr
                5

<210> SEQ ID NO 89
<211> LENGTH: 8
<212> TYPE: PRT
<213> ORGANISM: Human Papilloma Virus 16
<220> FEATURE:
<221> NAME/KEY: CHAIN
<223> OTHER INFORMATION: residues 80-87 of the E7 protein

<400> SEQUENCE: 89

Glu Asp Leu Leu Met Gly Thr Leu
                5

<210> SEQ ID NO 90
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 51-65 of the E6 protein

<400> SEQUENCE: 90

Asp Phe Ala Phe Arg Asp Leu Cys Ile Val Tyr Arg Asp Gly Asn
                5                   10                  15

<210> SEQ ID NO 91
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 46-54 of the E6 protein

<400> SEQUENCE: 91

Arg Arg Glu Val Tyr Asp Phe Ala Phe
                5

<210> SEQ ID NO 92
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 47-55 of the E6 protein

<400> SEQUENCE: 92

Arg Glu Val Tyr Asp Phe Ala Phe Arg
                5

<210> SEQ ID NO 93
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 48-56 of the E6 protein

<400> SEQUENCE: 93

Glu Val Tyr Asp Phe Ala Phe Arg Asp
                5
```

```
<210> SEQ ID NO 94
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 49-57 of the E6 protein

<400> SEQUENCE: 94

Val Tyr Asp Phe Ala Phe Arg Asp Leu
                5

<210> SEQ ID NO 95
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 50-58 of the E6 protein

<400> SEQUENCE: 95

Tyr Asp Phe Ala Phe Arg Asp Leu Cys
                5

<210> SEQ ID NO 96
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 51-59 of the E6 protein

<400> SEQUENCE: 96

Asp Phe Ala Phe Arg Asp Leu Cys Ile
                5

<210> SEQ ID NO 97
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 52-60 of the E6 protein

<400> SEQUENCE: 97

Phe Ala Phe Arg Asp Leu Cys Ile Val
                5

<210> SEQ ID NO 98
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 53-61 of the E6 protein

<400> SEQUENCE: 98

Ala Phe Arg Asp Leu Cys Ile Val Tyr
                5

<210> SEQ ID NO 99
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 54-62 of the E6 protein

<400> SEQUENCE: 99
```

Phe Arg Asp Leu Cys Ile Val Tyr Arg
                5

<210> SEQ ID NO 100
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 55-63 of the E6 protein

<400> SEQUENCE: 100

Arg Asp Leu Cys Ile Val Tyr Arg Asp
                5

<210> SEQ ID NO 101
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 56-64 of the E6 protein

<400> SEQUENCE: 101

Asp Leu Cys Ile Val Tyr Arg Asp Gly
                5

<210> SEQ ID NO 102
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 57-65 of the E6 protein

<400> SEQUENCE: 102

Leu Cys Ile Val Tyr Arg Asp Gly Asn
                5

<210> SEQ ID NO 103
<211> LENGTH: 11
<212> TYPE: PRT
<213> ORGANISM: Human Papilloma Virus 16
<220> FEATURE:
<221> NAME/KEY: CHAIN
<223> OTHER INFORMATION: residues 52-62 of the E6 protein

<400> SEQUENCE: 103

Phe Ala Phe Arg Asp Leu Cys Ile Val Tyr Arg
                5                   10

<210> SEQ ID NO 104
<211> LENGTH: 11
<212> TYPE: PRT
<213> ORGANISM: Human Papilloma Virus 16
<220> FEATURE:
<221> NAME/KEY: CHAIN
<223> OTHER INFORMATION: residues 51-61 of the E6 protein

<400> SEQUENCE: 104

Asp Phe Ala Phe Arg Asp Leu Cys Ile Val Tyr
                5                   10

<210> SEQ ID NO 105
<211> LENGTH: 10
<212> TYPE: PRT
<213> ORGANISM: Human Papilloma Virus 16
<220> FEATURE:
<221> NAME/KEY: CHAIN
<223> OTHER INFORMATION: residues 53-62 of the E6 protein

<400> SEQUENCE: 105

Ala Phe Arg Asp Leu Cys Ile Val Tyr Arg
                5                   10

<210> SEQ ID NO 106
<211> LENGTH: 8
<212> TYPE: PRT
<213> ORGANISM: Human Papilloma Virus 16
<220> FEATURE:
<221> NAME/KEY: CHAIN
<223> OTHER INFORMATION: residues 53-60 of the E6 protein

<400> SEQUENCE: 106

Ala Phe Arg Asp Leu Cys Ile Val
                5

<210> SEQ ID NO 107
<211> LENGTH: 8
<212> TYPE: PRT
<213> ORGANISM: Human Papilloma Virus 16
<220> FEATURE:
<221> NAME/KEY: CHAIN
<223> OTHER INFORMATION: residues 54-61 of the E6 protein

<400> SEQUENCE: 107

Phe Arg Asp Leu Cys Ile Val Tyr
                5

<210> SEQ ID NO 108
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 1-15 of the E6 protein

<400> SEQUENCE: 108

Met His Gln Lys Arg Thr Ala Met Phe Gln Asp Pro Gln Glu Arg
                5                   10                  15

<210> SEQ ID NO 109
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 6-20 of the E6 protein

<400> SEQUENCE: 109

Thr Ala Met Phe Gln Asp Pro Gln Glu Arg Pro Arg Lys Leu Pro
                5                   10                  15

<210> SEQ ID NO 110
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 11-25 of the E6 protein

<400> SEQUENCE: 110

Asp Pro Gln Glu Arg Pro Arg Lys Leu Pro Gln Leu Cys Thr Glu
                5                   10                  15

<210> SEQ ID NO 111
<211> LENGTH: 15

```
<212> TYPE: PRT
<213> ORGANISM: Human Papilloma Virus 16
<220> FEATURE:
<221> NAME/KEY: CHAIN
<223> OTHER INFORMATION: residues 46-60 of the E6 protein

<400> SEQUENCE: 111

Arg Arg Glu Val Tyr Asp Phe Ala Phe Arg Asp Leu Cys Ile Val
                5                   10                  15

<210> SEQ ID NO 112
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 56-70 of the E6 protein

<400> SEQUENCE: 112

Asp Leu Cys Ile Val Tyr Arg Asp Gly Asn Pro Tyr Ala Val Cys
                5                   10                  15

<210> SEQ ID NO 113
<211> LENGTH: 21
<212> TYPE: DNA
<213> ORGANISM: Artificial sequence
<220> FEATURE:
<221> NAME/KEY: primer_bind
<223> OTHER INFORMATION: sense oligonucleotide primer for amplifying
      HPV16

<400> SEQUENCE: 113
atggagatac acctacattg c                                                   21

<210> SEQ ID NO 114
<211> LENGTH: 22
<212> TYPE: DNA
<213> ORGANISM: Artificial sequence
<220> FEATURE:
<221> NAME/KEY: primer_bind
<223> OTHER INFORMATION: antisense oligonucleotide primer for
      amplifying HPV16

<400> SEQUENCE: 114
ggtttctgag aacagatggg gc                                                  22

<210> SEQ ID NO 115
<211> LENGTH: 20
<212> TYPE: DNA
<213> ORGANISM: Artificial sequence
<220> FEATURE:
<221> NAME/KEY: primer_bind
<223> OTHER INFORMATION: sense oligonucleotide primer for amplyfying
      beta-tubulin

<400> SEQUENCE: 115
cgcatcaacg tgtactacaa                                                     20

<210> SEQ ID NO 116
<211> LENGTH: 20
<212> TYPE: DNA
<213> ORGANISM: Artificial Sequence
<220> FEATURE:
<221> NAME/KEY: primer_bind
<223> OTHER INFORMATION: antisense oligonucleotide primer for
      amplifying beta-tubulin

<400> SEQUENCE: 116
tacgagctgg tggactgaga                                                     20
```

```
<210> SEQ ID NO 117
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 5-19 of the E6 protein

<400> SEQUENCE: 117

Arg Thr Ala Met Phe Gln Asp Pro Gln Glu Arg Pro Arg Lys Leu
                 5                  10                  15

<210> SEQ ID NO 118
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 9-22 of the E6 protein

<400> SEQUENCE: 118

Phe Gln Asp Pro Gln Glu Arg Pro Arg Lys Leu Pro Gln Leu
                 5                  10

<210> SEQ ID NO 119
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 12-26 of the E6 protein

<400> SEQUENCE: 119

Pro Gln Glu Arg Pro Arg Lys Leu Pro Gln Leu Cys Thr Glu Leu
                 5                  10                  15

<210> SEQ ID NO 120
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 20-34 of the E6 protein

<400> SEQUENCE: 120

Pro Gln Leu Cys Thr Glu Leu Gln Thr Thr Ile His Asp Ile Ile
                 5                  10                  15

<210> SEQ ID NO 121
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 24-38 of the E6 protein

<400> SEQUENCE: 121

Thr Glu Leu Gln Thr Thr Ile His Asp Ile Ile Leu Glu Cys Val
                 5                  10                  15

<210> SEQ ID NO 122
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 28-41 of the E6 protein
```

```
<400> SEQUENCE: 122

Thr Thr Ile His Asp Ile Ile Leu Glu Cys Val Tyr Cys Lys
                5                   10

<210> SEQ ID NO 123
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 31-45 of the E6 protein

<400> SEQUENCE: 123

His Asp Ile Ile Leu Glu Cys Val Tyr Cys Lys Gln Gln Leu Leu
                5                   10                  15

<210> SEQ ID NO 124
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 35-49 of the E6 protein

<400> SEQUENCE: 124

Leu Glu Cys Val Tyr Cys Lys Gln Gln Leu Leu Arg Arg Glu Val
                5                   10                  15

<210> SEQ ID NO 125
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 39-53 of the E6 protein

<400> SEQUENCE: 125

Tyr Cys Lys Gln Gln Leu Leu Arg Arg Glu Val Tyr Asp Phe Ala
                5                   10                  15

<210> SEQ ID NO 126
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 41-55 of the E6 protein

<400> SEQUENCE: 126

Lys Gln Gln Leu Leu Arg Arg Glu Val Tyr Asp Phe Ala Phe Arg
                5                   10                  15

<210> SEQ ID NO 127
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 45-59 of the E6 protein

<400> SEQUENCE: 127

Leu Arg Arg Glu Val Tyr Asp Phe Ala Phe Arg Asp Leu Cys Ile
                5                   10                  15

<210> SEQ ID NO 128
<211> LENGTH: 14
<212> TYPE: PRT
<213> ORGANISM: Human Papilloma Virus 16
```

```
<220> FEATURE:
<221> NAME/KEY: CHAIN
<223> OTHER INFORMATION: residues 49-62 of the E6 protein

<400> SEQUENCE: 128

Val Tyr Asp Phe Ala Phe Arg Asp Leu Cys Ile Val Tyr Arg
                5                   10

<210> SEQ ID NO 129
<211> LENGTH: 16
<212> TYPE: PRT
<213> ORGANISM: Human Papilloma Virus 16
<220> FEATURE:
<221> NAME/KEY: CHAIN
<223> OTHER INFORMATION: residues 52-67 of the E6 protein

<400> SEQUENCE: 129

Phe Ala Phe Arg Asp Leu Cys Ile Val Tyr Arg Asp Gly Asn Pro
                5                   10                  15
Tyr

<210> SEQ ID NO 130
<211> LENGTH: 13
<212> TYPE: PRT
<213> ORGANISM: Human Papilloma Virus 16
<220> FEATURE:
<221> NAME/KEY: CHAIN
<223> OTHER INFORMATION: residues 57-69 of the E6 protein

<400> SEQUENCE: 130

Leu Cys Ile Val Tyr Arg Asp Gly Asn Pro Tyr Ala Val
                5                   10

<210> SEQ ID NO 131
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 59-72 of the E6 protein

<400> SEQUENCE: 131

Ile Val Tyr Arg Asp Gly Asn Pro Tyr Ala Val Cys Asp Lys
                5                   10

<210> SEQ ID NO 132
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 62-76 of the E6 protein

<400> SEQUENCE: 132

Arg Asp Gly Asn Pro Tyr Ala Val Cys Asp Lys Cys Leu Lys Phe
                5                   10                  15

<210> SEQ ID NO 133
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 66-80 of the E6 protein

<400> SEQUENCE: 133

Pro Tyr Ala Val Cys Asp Lys Cys Leu Lys Phe Tyr Ser Lys Ile
                5                   10                  15
```

<210> SEQ ID NO 134
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 70-84 of the E6 protein

<400> SEQUENCE: 134

Cys Asp Lys Cys Leu Lys Phe Tyr Ser Lys Ile Ser Glu Tyr Arg
                5                   10                  15

<210> SEQ ID NO 135
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 74-88 of the E6 protein

<400> SEQUENCE: 135

Leu Lys Phe Tyr Ser Lys Ile Ser Glu Tyr Arg His Tyr Cys Tyr
                5                   10                  15

<210> SEQ ID NO 136
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 78-91 of the E6 protein

<400> SEQUENCE: 136

Ser Lys Ile Ser Glu Tyr Arg His Tyr Cys Tyr Ser Leu Tyr
                5                   10

<210> SEQ ID NO 137
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 81-95 of the E6 protein

<400> SEQUENCE: 137

Ser Glu Tyr Arg His Tyr Cys Tyr Ser Leu Tyr Gly Thr Thr Leu
                5                   10                  15

<210> SEQ ID NO 138
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 85-99 of the E6 protein

<400> SEQUENCE: 138

His Tyr Cys Tyr Ser Leu Tyr Gly Thr Thr Leu Glu Gln Gln Tyr
                5                   10                  15

<210> SEQ ID NO 139
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 89-103 of the E6 protein

<400> SEQUENCE: 139

Ser Leu Tyr Gly Thr Thr Leu Glu Gln Gln Tyr Asn Lys Pro Leu
                5                   10                  15

<210> SEQ ID NO 140
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 93-107 of the E6 protein

<400> SEQUENCE: 140

Thr Thr Leu Glu Gln Gln Tyr Asn Lys Pro Leu Cys Asp Leu Leu
                5                   10                  15

<210> SEQ ID NO 141
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 96-109 of the E6 protein

<400> SEQUENCE: 141

Glu Gln Gln Tyr Asn Lys Pro Leu Cys Asp Leu Leu Ile Arg
                5                   10

<210> SEQ ID NO 142
<211> LENGTH: 13
<212> TYPE: PRT
<213> ORGANISM: Human Papilloma Virus 16
<220> FEATURE:
<221> NAME/KEY: CHAIN
<223> OTHER INFORMATION: residues 99-111 of the E6 protein

<400> SEQUENCE: 142

Tyr Asn Lys Pro Leu Cys Asp Leu Leu Ile Arg Cys Ile
                5                   10

<210> SEQ ID NO 143
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 101-115 of the E6 protein

<400> SEQUENCE: 143

Lys Pro Leu Cys Asp Leu Leu Ile Arg Cys Ile Asn Cys Gln Lys
                5                   10                  15

<210> SEQ ID NO 144
<211> LENGTH: 13
<212> TYPE: PRT
<213> ORGANISM: Human Papilloma Virus 16
<220> FEATURE:
<221> NAME/KEY: CHAIN
<223> OTHER INFORMATION: residues 105-117 of the E6 protein

<400> SEQUENCE: 144

Asp Leu Leu Ile Arg Cys Ile Asn Cys Gln Lys Pro Leu
                5                   10

<210> SEQ ID NO 145
<211> LENGTH: 16
<212> TYPE: PRT
<213> ORGANISM: Human Papilloma Virus 16

```
<220> FEATURE:
<221> NAME/KEY: CHAIN
<223> OTHER INFORMATION: residues 107-122 of the E6 protein

<400> SEQUENCE: 145

Leu Ile Arg Cys Ile Asn Cys Gln Lys Pro Leu Cys Pro Glu Glu
                5                   10                  15
Lys

<210> SEQ ID NO 146
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 112-126 of the E6 protein

<400> SEQUENCE: 146

Asn Cys Gln Lys Pro Leu Cys Pro Glu Glu Lys Gln Arg His Leu
                5                   10                  15

<210> SEQ ID NO 147
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 116-129 of the E6 protein

<400> SEQUENCE: 147

Pro Leu Cys Pro Glu Glu Lys Gln Arg His Leu Asp Lys Lys
                5                   10

<210> SEQ ID NO 148
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 119-133 of the E6 protein

<400> SEQUENCE: 148

Pro Glu Glu Lys Gln Arg His Leu Asp Lys Lys Gln Arg Phe His
                5                   10                  15

<210> SEQ ID NO 149
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 122-136 of the E6 protein

<400> SEQUENCE: 149

Lys Gln Arg His Leu Asp Lys Lys Gln Arg Phe His Asn Ile Arg
                5                   10                  15

<210> SEQ ID NO 150
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 126-139 of the E6 protein

<400> SEQUENCE: 150

Leu Asp Lys Lys Gln Arg Phe His Asn Ile Arg Gly Arg Trp
                5                   10
```

```
<210> SEQ ID NO 151
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 129-142 of the E6 protein

<400> SEQUENCE: 151

Lys Gln Arg Phe His Asn Ile Arg Gly Arg Trp Thr Gly Arg
                5                   10

<210> SEQ ID NO 152
<211> LENGTH: 13
<212> TYPE: PRT
<213> ORGANISM: Human Papilloma Virus 16
<220> FEATURE:
<221> NAME/KEY: CHAIN
<223> OTHER INFORMATION: residues 132-144 of the E6 protein

<400> SEQUENCE: 152

Phe His Asn Ile Arg Gly Arg Trp Thr Gly Arg Cys Met
                5                   10

<210> SEQ ID NO 153
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 134-148 of the E6 protein

<400> SEQUENCE: 153

Asn Ile Arg Gly Arg Trp Thr Gly Arg Cys Met Ser Cys Cys Arg
                5                   10                  15

<210> SEQ ID NO 154
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 138-151 of the E6 protein

<400> SEQUENCE: 154

Arg Trp Thr Gly Arg Cys Met Ser Cys Cys Arg Ser Ser Arg
                5                   10

<210> SEQ ID NO 155
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 141-154 of the E6 protein

<400> SEQUENCE: 155

Gly Arg Cys Met Ser Cys Cys Arg Ser Ser Arg Thr Arg Arg
                5                   10

<210> SEQ ID NO 156
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 144-158 of the E6 protein
```

```
<400> SEQUENCE: 156

Met Ser Cys Cys Arg Ser Ser Arg Thr Arg Arg Glu Thr Gln Leu
                5                   10                  15

<210> SEQ ID NO 157
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 5-19 of the E7 protein

<400> SEQUENCE: 157

Thr Pro Thr Leu His Glu Tyr Met Leu Asp Leu Gln Pro Glu Thr
                5                   10                  15

<210> SEQ ID NO 158
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 9-23 of the E7 protein

<400> SEQUENCE: 158

His Glu Tyr Met Leu Asp Leu Gln Pro Glu Thr Thr Asp Leu Tyr
                5                   10                  15

<210> SEQ ID NO 159
<211> LENGTH: 13
<212> TYPE: PRT
<213> ORGANISM: Human Papilloma Virus 16
<220> FEATURE:
<221> NAME/KEY: CHAIN
<223> OTHER INFORMATION: residues 13-25 of the E7 protein

<400> SEQUENCE: 159

Leu Asp Leu Gln Pro Glu Thr Thr Asp Leu Tyr Cys Tyr
                5                   10

<210> SEQ ID NO 160
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 15-28 of the E7 protein

<400> SEQUENCE: 160

Leu Gln Pro Glu Thr Thr Asp Leu Tyr Cys Tyr Glu Gln Leu
                5                   10

<210> SEQ ID NO 161
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 18-32 of the E7 protein

<400> SEQUENCE: 161

Glu Thr Thr Asp Leu Tyr Cys Tyr Glu Gln Leu Asn Asp Ser Ser
                5                   10                  15

<210> SEQ ID NO 162
<211> LENGTH: 17
<212> TYPE: PRT
<213> ORGANISM: Human Papilloma Virus 16
```

-continued

```
<220> FEATURE:
<221> NAME/KEY: CHAIN
<223> OTHER INFORMATION: residues 22-38 of the E7 protein

<400> SEQUENCE: 162

Leu Tyr Cys Tyr Glu Gln Leu Asn Asp Ser Ser Glu Glu Glu Asp
                5                   10                  15
Glu Ile

<210> SEQ ID NO 163
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 28-42 of the E7 protein

<400> SEQUENCE: 163

Leu Asn Asp Ser Ser Glu Glu Glu Asp Glu Ile Asp Gly Pro Ala
                5                   10                  15

<210> SEQ ID NO 164
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 32-45 of the E7 protein

<400> SEQUENCE: 164

Ser Glu Glu Glu Asp Glu Ile Asp Gly Pro Ala Gly Gln Ala
                5                   10

<210> SEQ ID NO 165
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 35-49 of the E7 protein

<400> SEQUENCE: 165

Glu Asp Glu Ile Asp Gly Pro Ala Gly Gln Ala Glu Pro Asp Arg
                5                   10                  15

<210> SEQ ID NO 166
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 39-52 of the E7 protein

<400> SEQUENCE: 166

Asp Gly Pro Ala Gly Gln Ala Glu Pro Asp Arg Ala His Tyr
                5                   10

<210> SEQ ID NO 167
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 42-55 of the E7 protein

<400> SEQUENCE: 167

Ala Gly Gln Ala Glu Pro Asp Arg Ala His Tyr Asn Ile Val
                5                   10
```

<210> SEQ ID NO 168
<211> LENGTH: 13
<212> TYPE: PRT
<213> ORGANISM: Human Papilloma Virus 16
<220> FEATURE:
<221> NAME/KEY: CHAIN
<223> OTHER INFORMATION: residues 45-57 of the E7 protein

<400> SEQUENCE: 168

Ala Glu Pro Asp Arg Ala His Tyr Asn Ile Val Thr Phe
                5                   10

<210> SEQ ID NO 169
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 47-60 of the E7 protein

<400> SEQUENCE: 169

Pro Asp Arg Ala His Tyr Asn Ile Val Thr Phe Cys Cys Lys
                5                   10

<210> SEQ ID NO 170
<211> LENGTH: 16
<212> TYPE: PRT
<213> ORGANISM: Human Papilloma Virus 16
<220> FEATURE:
<221> NAME/KEY: CHAIN
<223> OTHER INFORMATION: residues 50-65 of the E7 protein

<400> SEQUENCE: 170

Ala His Tyr Asn Ile Val Thr Phe Cys Cys Lys Cys Asp Ser Thr
                5                   10                  15
Leu

<210> SEQ ID NO 171
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 55-69 of the E7 protein

<400> SEQUENCE: 171

Val Thr Phe Cys Cys Lys Cys Asp Ser Thr Leu Arg Leu Cys Val
                5                   10                  15

<210> SEQ ID NO 172
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 59-73 of the E7 protein

<400> SEQUENCE: 172

Cys Lys Cys Asp Ser Thr Leu Arg Leu Cys Val Gln Ser Thr His
                5                   10                  15

<210> SEQ ID NO 173
<211> LENGTH: 15
<212> TYPE: PRT
<213> ORGANISM: Human Papilloma Virus 16
<220> FEATURE:
<221> NAME/KEY: CHAIN -continued
<223> OTHER INFORMATION: residues 63-77 of the E7 protein

<400> SEQUENCE: 173

Ser Thr Leu Arg Leu Cys Val Gln Ser Thr His Val Asp Ile Arg
                5                   10                  15

<210> SEQ ID NO 174
<211> LENGTH: 13
<212> TYPE: PRT
<213> ORGANISM: Human Papilloma Virus 16
<220> FEATURE:
<221> NAME/KEY: CHAIN
<223> OTHER INFORMATION: residues 67-79 of the E7 protein

<400> SEQUENCE: 174

Leu Cys Val Gln Ser Thr His Val Asp Ile Arg Thr Leu
                5                   10

<210> SEQ ID NO 175
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 69-83 of the E7 protein

<400> SEQUENCE: 175

Val Gln Ser Thr His Val Asp Ile Arg Thr Leu Glu Asp Leu Leu
                5                   10                  15

<210> SEQ ID NO 176
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 73-87 of the E7 protein

<400> SEQUENCE: 176

His Val Asp Ile Arg Thr Leu Glu Asp Leu Leu Met Gly Thr Leu
                5                   10                  15

<210> SEQ ID NO 177
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 77-90 of the E7 protein

<400> SEQUENCE: 177

Arg Thr Leu Glu Asp Leu Leu Met Gly Thr Leu Gly Ile Val
                5                   10

<210> SEQ ID NO 178
<211> LENGTH: 14
<212> TYPE: PRT
<213> ORGANISM: Human Papilloma Virus 16
<220> FEATURE:
<221> NAME/KEY: CHAIN
<223> OTHER INFORMATION: residues 80-93 of the E7 protein

<400> SEQUENCE: 178

Glu Asp Leu Leu Met Gly Thr Leu Gly Ile Val Cys Pro Ile
                5                   10

<210> SEQ ID NO 179
<211> LENGTH: 16

```
<212> TYPE: PRT
<213> ORGANISM: Human Papilloma Virus 16
<220> FEATURE:
<221> NAME/KEY: CHAIN
<223> OTHER INFORMATION: residues 83-98 of the E7 protein

<400> SEQUENCE: 179

Leu Met Gly Thr Leu Gly Ile Val Cys Pro Ile Cys Ser Gln Lys
                 5                  10                  15
Pro

<210> SEQ ID NO 180
<211> LENGTH: 9
<212> TYPE: PRT
<213> ORGANISM: Human Papilloma Virus 33
<220> FEATURE:
<221> NAME/KEY: CHAIN
<223> OTHER INFORMATION: residues 22-30 of HPV 33

<400> SEQUENCE: 180

Thr Ile His Asn Ile Glu Leu Gln Cys
                 5

<210> SEQ ID NO 181
<211> LENGTH: 9
<212> TYPE: PRT
<213> ORGANISM: Human Papilloma Virus 35
<220> FEATURE:
<221> NAME/KEY: CHAIN
<223> OTHER INFORMATION: residues 22-30 of HPV 35

<400> SEQUENCE: 181

Ser Ile His Glu Ile Cys Leu Asn Cys
                 5

<210> SEQ ID NO 182
<211> LENGTH: 9
<212> TYPE: PRT
<213> ORGANISM: Human Papilloma Virus 73
<220> FEATURE:
<221> NAME/KEY: CHAIN
<223> OTHER INFORMATION: residues 23-31 of HPV 73

<400> SEQUENCE: 182

Ser Ile His Asp Ile Asn Leu Asp Cys
                 5

<210> SEQ ID NO 183
<211> LENGTH: 9
<212> TYPE: PRT
<213> ORGANISM: Human Papilloma Virus 68
<220> FEATURE:
<221> NAME/KEY: CHAIN
<223> OTHER INFORMATION: residues 84-92 of HPV 68

<400> SEQUENCE: 183

Arg Glu Asn Leu Arg Asn Val Glu Leu
                 5

<210> SEQ ID NO 184
<211> LENGTH: 9
<212> TYPE: PRT
<213> ORGANISM: Human Papilloma Virus 73
<220> FEATURE:
<221> NAME/KEY: CHAIN
<223> OTHER INFORMATION: amino acid residues of HPV 73 analogous to
      HPV16 E7 79-87

<400> SEQUENCE: 184
```

```
Ile Glu Glu Leu Leu Met Gly Thr Leu
              5

<210> SEQ ID NO 185
<211> LENGTH: 15
<212> TYPE: PRT
<213> ORGANISM: Human Papilloma Virus 16
<220> FEATURE:
<221> NAME/KEY: CHAIN
<223> OTHER INFORMATION: residues 141-155 of the E6 protein

<400> SEQUENCE: 185

Gly Arg Cys Met Ser Cys Cys Arg Ser Ser Arg Thr Arg Arg Glu
              5                  10                  15

<210> SEQ ID NO 186
<211> LENGTH: 7
<212> TYPE: PRT
<213> ORGANISM: Human Papilloma Virus 16
<220> FEATURE:
<221> NAME/KEY: CHAIN
<223> OTHER INFORMATION: residues 31-37 of the E6 protein

<400> SEQUENCE: 186

His Asp Ile Ile Leu Glu Cys
              5

<210> SEQ ID NO 187
<211> LENGTH: 7
<212> TYPE: PRT
<213> ORGANISM: Human Papilloma Virus 16
<220> FEATURE:
<221> NAME/KEY: CHAIN
<223> OTHER INFORMATION: residues 32-38 of the E6 protein

<400> SEQUENCE: 187

Asp Ile Ile Leu Glu Cys Val
              5

<210> SEQ ID NO 188
<211> LENGTH: 10
<212> TYPE: PRT
<213> ORGANISM: Human Papilloma Virus 16
<220> FEATURE:
<221> NAME/KEY: CHAIN
<223> OTHER INFORMATION: residues 30-39 of the E6 protein

<400> SEQUENCE: 188

Ile His Asp Ile Ile Leu Glu Cys Val Tyr
              5                  10

<210> SEQ ID NO 189
<211> LENGTH: 11
<212> TYPE: PRT
<213> ORGANISM: Human Papilloma Virus 16
<220> FEATURE:
<221> NAME/KEY: CHAIN
<223> OTHER INFORMATION: residues 142-152 of the E6 protein

<400> SEQUENCE: 189

Arg Cys Met Ser Cys Cys Arg Ser Ser Arg Thr
              5                  10

<210> SEQ ID NO 190
<211> LENGTH: 11
<212> TYPE: PRT
<213> ORGANISM: Human Papilloma Virus 16
<220> FEATURE:
```

-continued

```
<221> NAME/KEY: CHAIN
<223> OTHER INFORMATION: residues 143-153 of the E6 protein

<400> SEQUENCE: 190

Cys Met Ser Cys Cys Arg Ser Ser Arg Thr Arg
                5                   10

<210> SEQ ID NO 191
<211> LENGTH: 11
<212> TYPE: PRT
<213> ORGANISM: Human Papilloma Virus 16
<220> FEATURE:
<221> NAME/KEY: CHAIN
<223> OTHER INFORMATION: residues 144-154 of the E6 protein

<400> SEQUENCE: 191

Met Ser Cys Cys Arg Ser Ser Arg Thr Arg Arg
                5                   10

<210> SEQ ID NO 192
<211> LENGTH: 11
<212> TYPE: PRT
<213> ORGANISM: Human Papilloma Virus 16
<220> FEATURE:
<221> NAME/KEY: CHAIN
<223> OTHER INFORMATION: residues 28-38 of the E6 protein

<400> SEQUENCE: 192

Thr Thr Ile His Asp Ile Ile Leu Glu Cys Val
                5                   10

<210> SEQ ID NO 193
<211> LENGTH: 11
<212> TYPE: PRT
<213> ORGANISM: Human Papilloma Virus 16
<220> FEATURE:
<221> NAME/KEY: CHAIN
<223> OTHER INFORMATION: residues 29-39 of the E6 protein

<400> SEQUENCE: 193

Thr Ile His Asp Ile Ile Leu Glu Cys Val Tyr
                5                   10

<210> SEQ ID NO 194
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 33-41 of the E6 protein

<400> SEQUENCE: 194

Ile Ile Leu Glu Cys Val Tyr Cys Lys
                5

<210> SEQ ID NO 195
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 34-42 of the E6 protein

<400> SEQUENCE: 195

Ile Leu Glu Cys Val Tyr Cys Lys Gln
                5

<210> SEQ ID NO 196
```

```
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 35-43 of the E6 protein

<400> SEQUENCE: 196

Leu Glu Cys Val Tyr Cys Lys Gln Gln
                5

<210> SEQ ID NO 197
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 36-44 of the E6 protein

<400> SEQUENCE: 197

Glu Cys Val Tyr Cys Lys Gln Gln Leu
                5

<210> SEQ ID NO 198
<211> LENGTH: 9
<212> TYPE: PRT
<213> ORGANISM: Human Papilloma Virus 16
<220> FEATURE:
<221> NAME/KEY: CHAIN
<223> OTHER INFORMATION: residues 37-45 of the E6 protein

<400> SEQUENCE: 198

Cys Val Tyr Cys Lys Gln Gln Leu Leu
                5
```